(12) United States Patent
Huang et al.

(10) Patent No.: US 11,629,124 B2
(45) Date of Patent: Apr. 18, 2023

(54) SOLID FORMS COMPRISING AN OXIME ETHER COMPOUND, COMPOSITIONS AND METHODS OF USE THEREOF

(71) Applicant: Novartis AG, Basel (CH)

(72) Inventors: Lianfeng Huang, Basking Ridge, NJ (US); Daozhong Zou, Raritan, NJ (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/752,041

(22) Filed: Jan. 24, 2020

(65) Prior Publication Data

US 2020/0399213 A1    Dec. 24, 2020

Related U.S. Application Data

(63) Continuation of application No. 15/916,015, filed on Mar. 8, 2018, now abandoned.

(60) Provisional application No. 62/591,880, filed on Nov. 29, 2017, provisional application No. 62/469,150, filed on Mar. 9, 2017.

(51) Int. Cl.
   C07D 205/04      (2006.01)
   A61K 9/20        (2006.01)
   A61K 9/48        (2006.01)

(52) U.S. Cl.
   CPC .............. *C07D 205/04* (2013.01); *A61K 9/20* (2013.01); *A61K 9/48* (2013.01); *C07B 2200/13* (2013.01)

(58) Field of Classification Search
   CPC .................................................. C07D 205/04
   USPC ......................................................... 548/950
   See application file for complete search history.

(56) References Cited

U.S. PATENT DOCUMENTS

| | | | |
|---|---|---|---|
| 4,158,015 A | 6/1979 | Paul | |
| 7,750,021 B2 | 7/2010 | Mi et al. | |
| 7,939,519 B2 | 5/2011 | Pan et al. | |
| 8,173,634 B2 * | 5/2012 | Liu | C07D 205/04 514/210.17 |
| 8,486,930 B2 * | 7/2013 | De La Cruz | A61K 31/397 514/210.17 |
| 8,492,441 B2 * | 7/2013 | Legangneux | A61K 31/445 514/640 |
| 8,673,918 B2 | 3/2014 | Ruegger et al. | |
| 8,697,682 B2 | 4/2014 | De La Cruz et al. | |
| 8,741,963 B2 | 6/2014 | Hiestand et al. | |
| 9,149,459 B2 | 10/2015 | Aluned et al. | |
| 2009/0036423 A1 | 2/2009 | Pan et al. | |
| 2012/0115840 A1 | 5/2012 | Ciszewski et al. | |
| 2012/0122836 A1 | 5/2012 | Liu et al. | |
| 2013/0273161 A1 | 10/2013 | Bouillot et al. | |
| 2014/0179636 A1 | 6/2014 | Georgousis et al. | |
| 2014/0228446 A1 | 8/2014 | Hiestand | |
| 2015/0018577 A1 | 1/2015 | Gallou et al. | |
| 2015/0087720 A1 | 3/2015 | Kovarik et al. | |
| 2015/0175536 A1 | 6/2015 | Ciszewski et al. | |
| 2015/0218090 A1 | 8/2015 | Wallstroem | |

FOREIGN PATENT DOCUMENTS

| | | | |
|---|---|---|---|
| CN | 104337808 | 2/2015 | |
| EP | 0009865 | 4/1980 | |
| EP | WO2012069202 | * 5/2012 | .............. A61P 37/06 |
| EP | WO2015091531 | * 6/2015 | .............. A61P 37/00 |
| ES | 2397482 | * 6/2010 | ........... A61K 31/522 |
| ES | 2463289 | * 11/2010 | ......... A61K 31/5025 |
| WO | WO 2004/103306 | 12/2004 | |
| WO | WO 2006/058316 | 6/2006 | |
| WO | WO 2006/072562 | 7/2006 | |
| WO | WO 2007/021666 | 2/2007 | |
| WO | WO 2009/048993 | 4/2009 | |
| WO | WO 2010/010127 | 1/2010 | |
| WO | WO 2010/020610 | 2/2010 | |
| WO | WO 2010/071794 | 6/2010 | |
| WO | WO 2010/072703 | 7/2010 | |
| WO | WO 2010/080409 | 7/2010 | |
| WO | WO 2010/080455 | 7/2010 | |
| WO | WO 2011/116091 | 9/2011 | |
| WO | WO 2012/093161 | 7/2012 | |
| WO | WO 2012/095853 | 7/2012 | |
| WO | WO 2013/057212 | 4/2013 | |
| WO | WO 2013/113915 | 8/2013 | |
| WO | WO 2014/161606 | 10/2014 | |
| WO | WO 2015/155709 | 10/2015 | |
| WO | WO 2015/155711 | 10/2015 | |

OTHER PUBLICATIONS

Bauer, Journal of Validation Technology, 2008, 15-23.*
Caira, Topics in Current Chemistry, Springer, Berlin, DE, vol. 198, Jan. 1, 1998, pp. 163-208.*
Marriott, Pharmaceutical Compound and Dispensing, Second Edition, 2010, 1-288.*
Ansel, Pharmaceutical Dosage Forms and Drug Delivery Systems, 1999.*
"A multicenter, randomized, doubleblind, parallel-group, placebo-controlled variable treatment duration study evaluating the efficacy and safety of Siponimod (BAF312) in patients with secondary progressive multiple sclerosis followed by extended treatment with openlabel BAF312," EU Clinical Trials Register, accessed at https://www.clinicaltrialsregister.eu/ctr-search/trial/2012-003056-36/DE, accessed on Nov. 30, 2017; 8 pages.
"A phase II, double-blind, randomized, multicenter, adaptive dose-ranging, placebo-controlled, parallel group study evaluating safety, tolerability and efficacy on MRI lesion parameters and determining the dose response curve of BAF312 given orally once daily in patients with relapsing-remitting multiple sclerosis," EU Clinical Trials Register, accessed at https://www.clinicaltrialsregister.eu/ctrsearch/trial/2008-008719-25/DE, accessed on Nov. 30, 2017; 8 pages.

(Continued)

*Primary Examiner* — Nizal S Chandrakumar
(74) *Attorney, Agent, or Firm* — Finnegan, Henderson, Farabow, Garrett & Dunner, LLP

(57) ABSTRACT

Provided herein are formulations, processes, solid forms and methods of use relating to (E)-1-(4-(1-(((4-cyclohexyl-3-(trifluoromethyl)benzyl)oxy)imino)ethyl)-2-ethylbenzyl)azetidine-3-carboxylic acid.

10 Claims, 44 Drawing Sheets

(56) References Cited

OTHER PUBLICATIONS

"Exploring the Efficacy and Safety of Siponimod in Patients With Secondary Progressive Multiple Sclerosis" Clinical Trials.gov, accessed at https://clinicaltrials.gov/ct2/show/NCT01665144?term=NCT01665144&rank=1, accessed on Nov. 30, 2017; 6 pages.

"Mechanistic Studies of Phase III Trial With BAF312 in Secondary Progressive Multiple Sclerosis," Clinical Trials.gov, accessed at https://clinicaltrials.gov/ct2/show/NCT02330965?term=NCT02330965&rank=1, accessed on Nov. 30, 2017; 8 pages.

"Safety, Tolerability, Efficacy and Optimal Dose Finding Study of BAF312 in Patients With Relapsing remitting Multiple Sclerosis," Clinical Trials.gov, accessed at https://clinicaltrials.gov/ct2/show/NCT00879658?term=NCT00879658&rank=1, accessed on Nov. 30, 2017; 6 pages.

Banker et al., 1996, "Modern Pharmaceutics, 3ed", Marcel Dekker, New York:451 and 596.

Bernstein, 2004, "Crystal Structure Prediction and Polymorphism," ACA Transactions 39:14-23.

Braga and Grepioni, 2005, "Making crystals from crystals: a green route to crystal engineering and polymorphism", Chem. Commun.:3635-3645.

Briard et al., Jun. 2015, "MS565: Aspect Tracer for Evaluating the Brain Penetration of BAF312 (Siponimod)", ChemMedChem, 10(6): 1008-18.

Buzard et al., 2014, "7-Benzyloxy-2,3-dihydro-1H-pyrrolo[1,2-a]indol-1-yl)acetic Acids as $S1P_1$ Fucntional Antagonists", ACS Med Chem Lett., 5(12):1334-1339.

CAS Registry No. 1230487-00-9; retrieved via SciFinder search on Sep. 9, 2015; 2 pages.

Colandrea, 2006, "2,5-Disubstituted pyrrolidine carboxylates as potent, orally active sphingosine-1-phosphate (S1P) receptor agonists", Biorg. Med. Chem. Lett., 16(11):2905-2908.

Dorwald, Zaragoza, 2005, Side Reactions in Organic Synthesis: A Guide to Successful Design, Weinheim: WILEY-VCR, Verlag GmbH & Co. KGaA, preface; 4 pages.

Gergely et al., Nov. 2012, "The selective sphingosine 1-phosphate receptor modulator BAF312 redirects lymphocyte distribution and has species-specific effects on heart rate", Br. J. Pharmacol., 167(5): 1035-1047.

Gritter et al., 1964, "Oxidation of benzyl alcohols with manganese dioxide", Nature, 202: 179-181.

Jones et al., 2006, "Pharmaceutical Cocrystals: An Emerging Approach to Physical Property Enhancement", MRS Bulletin 31:875-879.

Kim et al., 2013, "A development of rapid, practical and selective process for preparation of Z-Oximes", Journal of the Korean Chemical Society, 57(2):295-299.

Legangneux et al., 2013, "Dose titration of BAF312 attenuates the initial heart rate reducing effect in healthy subjects", Mar, Br. J. Clin. Pharmacol., 75(3):831-841.

Pan et al., 2013, "Discovery of BAF312 (Siponimod), a Potent and Selective S1P Receptor Modulator", ACS Med Chem Lett., 4(3):333-337.

Pan et al., 2013, "Supporting Information: Discovery of BAF312 (Siponimod), a Potent and Selective S1P Receptor Modulator", ACS Med Chem Lett., 4(3):16 pages.

Price, 2004, "The computational prediction of pharmaceutical crystal structures and polymorphism", Advanced Drug Delivery Reviews, 56:301-319.

PubChem Substance Database, SID=240115276, https://pubchem.ncbi.nlm.nih.gov/substance/240115276; 7 pages (accessed Sep. 5, 2018).

PubChem Compound Database, CID=I 1432307, https://pubchem.ncbi.nlm.nih.gov/compound/11432307; 15 pages (accessed Sep. 1, 2018).

Selmaj et al., Aug. 2013, "Siponimod for patients with relapsing-remitting multiple sclerosis (BOLD): an adaptive, dose-ranging, randomised, phase 2 study", Lancet. Neurol., 12(8):756-67.

Shakeri-Nejad et al., 2014, "Effects of Therapeutic and Supratherapeutic Doses of Siponimod (BAF312), A Selective S1P 1,5 Receptor Modulator, on Cardiac Repolarization: Results of a Thorough QT/QTc (TQT) Study", American Academy of Neurology (AAN), Philadelphia, Pennsylvania, Apr. 26-May 3, 2014 (Novartis), Poster Presentation; 5 pages.

Shakeri-Nejad et al., 2015, "Pharmacokinetics, Safety and Tolerability of Siponimod (BAF312) in Subjects with Different Levels of Hepatic Impairment Compared to Demographically Matched Healthy Subjects (PI .135)", Neurology, Apr. 6, 2015, 84(14), Poster Presentation; 5 pages.

U.S. Pharmacopeia, 1995, 23rd ed.: p. 1843-1844.

U.S. Pharmacopeia, 2003, p. 2228.

Vippagunta et al., 2001, "Crystalline solids", Adv. Drug. Deliv. Rev., 48:3-26.

Wolff, Manfred E., 1995, "Burger's Medicinal Chemistry, ted, Part 1", John Wiley & Sons: p. 975-977.

Yu, L., 2001, "Amoiphous pharmaceutical solids: preparation, characterization and stabilization", Adv. Drug. Deliv. Rev., 48(1): p. 27-42.

\* cited by examiner

SOLID FORMS COMPRISING AN OXIME ETHER COMPOUND, COMPOSITIONS AND METHODS OF USE THEREOF

This application is a continuation of U.S. patent application Ser. No. 15/916,015, filed on Mar. 8, 2018, which claims the benefit of U.S. Provisional Application No. 62/591,880, filed Nov. 29, 2017, and U.S. Provisional Application No. 62/469,150, filed on Mar. 9, 2017, each of which is incorporated herein by reference in its entirety.

1. FIELD

Provided herein are solid forms comprising (E)-1-(4-(1-(((4-cyclohexyl-3-(trifluoromethyl)benzyl)oxy)imino) ethyl)-2-ethylbenzyl)azetidine-3-carboxylic acid, or a tautomer thereof. Pharmaceutical compositions comprising such solid forms and methods of use of such solid forms for treating, preventing, and managing various disorders are also provided herein.

2. BACKGROUND

When the immune system functions normally, it produces a response intended to protect against harmful or foreign substances such as bacteria, parasites, and cancerous cells. Autoimmune diseases arise when the immune system attacks one or more of the body's normal constituents as if they were a foreign substance. These attacks cause inflammation and tissue damage that may lead to autoimmune disorders. There are more than 80 diseases that occur as a result of the body's autoimmune response to various harmful or foreign substances, affecting more than 23.5 million people in the United States. Some of the most common types of autoimmune or chronic inflammatory diseases include Graves' disease, Type 1 diabetes, multiple sclerosis, inflammatory bowel disease, systemic lupus, polymyositis, dermatomyositis, lupus nephritis, rheumatoid arthritis, and psoriasis.

Multiple Sclerosis ("MS") is an autoimmune disease of the central nervous system, characterized by degeneration of the protective sheath ("myelin") that covers nerve fibers in the brain and spinal cord. More than 2.5 million people in the world suffer from MS, and it is the most common neurologic, disabling disease in young adults. Diagnosis is generally made between 15 and 50 years of age, with symptoms either occurring in recurring, isolated attacks (i.e., relapsing forms) or symptoms increasing over time (i.e., progressive forms). Permanent neurological dysfunction can result from incomplete recovery from acute relapses or as a consequence of slow progression of disability.

There is a need in the art for novel drug products for the treatment of MS and other autoimmune diseases of the central nervous systems. Alternative solid forms of pharmaceutical compounds have emerged as a possible approach to modulate or enhance the physical and chemical properties of drug products. The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solid forms include crystalline solids and amorphous solids, depending on the product and its mode of administration.

Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (at present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable and marketable pharmaceutical product.

3. SUMMARY

Provided herein are solid forms comprising Compound 1 (e.g., crystalline forms, amorphous forms, polymorphs or mixtures thereof):

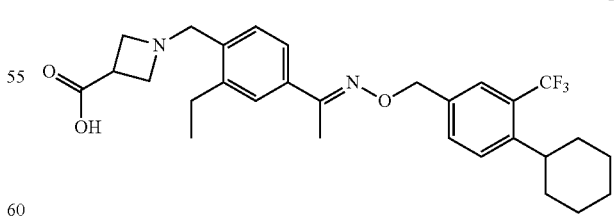

1 having the name (E)-1-(4-(1-(((4-cyclohexyl-3-(trifluoromethyl)benzyl)oxy)imino)ethyl)-2-ethylbenzyl)azetidine-3-carboxylic acid, including tautomers thereof. Also provided herein are methods of preparing, isolating, and characterizing the solid forms.

In one embodiment, described herein is a solid form comprising Compound 1, or a tautomer thereof:

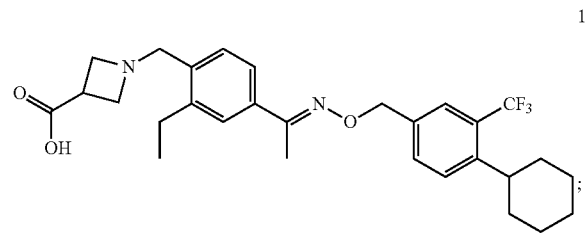 [SMILES: CCc1cc(/C(C)=N/OCc2ccc(C3CCCCC3)c(C(F)(F)F)c2)ccc1CN1CC(C(=O)O)C1]

which has an X-ray powder diffraction pattern comprising three or more characteristic peaks at approximately 2.3, 3.9, 7.7, 11.5, or 20.9° 2θ. In a certain embodiment, the solid form has an X-ray powder diffraction pattern comprising four or more characteristic peaks at approximately 2.3, 3.9, 7.7, 11.5, or 20.9° 2θ. In a certain embodiment, the solid form has an X-ray powder diffraction pattern comprising five or more characteristic peaks at approximately 2.3, 3.9, 7.7, 11.5, or 20.9° 2θ. In a certain embodiment, the solid form has an X-ray powder diffraction pattern substantially as shown in FIG. 1. In a certain embodiment, the solid form has a DSC thermogram comprising an endothermic event with a peak maximum temperature of about 54° C. and another endothermic event with an onset temperature of about 102° C. In a certain embodiment, the solid form is solvated by isopropyl ether.

In another embodiment, described herein is a solid form comprising Compound 1, or a tautomer thereof:

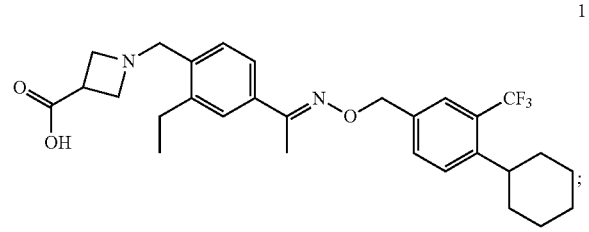 [SMILES: CCc1cc(/C(C)=N/OCc2ccc(C3CCCCC3)c(C(F)(F)F)c2)ccc1CN1CC(C(=O)O)C1]

which has an X-ray powder diffraction pattern comprising three or more characteristic peaks at approximately 2.3, 2.8, 7.7, 8.4, 11.5, or 20.9° 2θ. In a certain embodiment, the solid form has an X-ray powder diffraction pattern comprising four or more characteristic peaks at approximately 2.3, 2.8, 7.7, 8.4, 11.5, or 20.9° 2θ. In a certain embodiment, the solid form has an X-ray powder diffraction pattern comprising five or more characteristic peaks at approximately 2.3, 2.8, 7.7, 8.4, 11.5, or 20.9° 2θ. In a certain embodiment, the solid form has an X-ray powder diffraction pattern comprising six characteristic peaks at approximately 2.3, 2.8, 7.7, 8.4, 11.5, or 20.9° 2θ. In a certain embodiment, the solid form has an X-ray powder diffraction pattern substantially as shown in FIG. 5. In a certain embodiment, the solid form has a DSC thermograph comprising a first endothermic event with an onset temperature of about 40.2° C. and a peak maximum temperature of about 47.7° C. In a certain embodiment, the solid form is solvated by cyclohexane.

In another embodiment, provided herein is a solid form comprising Compound 1, or a tautomer thereof:

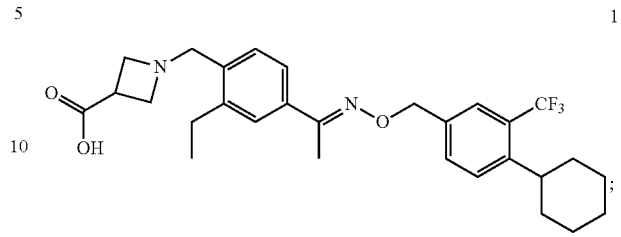

which has an X-ray powder diffraction pattern comprising three or more characteristic peaks at approximately 2.2, 3.9, 6.5, 7.7, 11.5, or 20.9° 2θ. In a certain embodiment, the solid form has an X-ray powder diffraction pattern comprising four or more characteristic peaks at approximately 2.2, 3.9, 6.5, 7.7, 11.5, or 20.9° 2θ. In a certain embodiment, the solid form has an X-ray powder diffraction pattern comprising five or more characteristic peaks at approximately 2.2, 3.9, 6.5, 7.7, 11.5, or 20.9° 2θ. In a certain embodiment, the solid form has an X-ray powder diffraction pattern comprising six characteristic peaks at approximately 2.2, 3.9, 6.5, 7.7, 11.5, or 20.9° 2θ. In a certain embodiment, the solid form has an X-ray powder diffraction pattern substantially as shown in FIG. 9. In a certain embodiment, the solid form has a DSC thermogram comprising an endothermic event with an onset temperature of about 101.7° C. In a certain embodiment, the solid form is solvated by heptane.

In another embodiment, provided herein is a solid form comprising Compound 1, or a tautomer thereof:

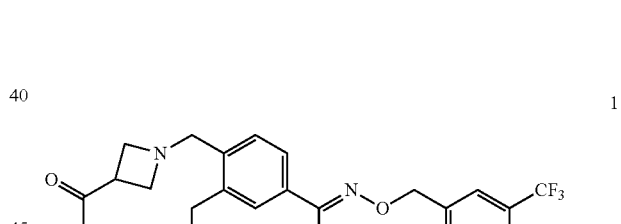

which has an X-ray powder diffraction pattern comprising three or more characteristic peaks at approximately 3.7, 7.3, 11.0, 18.3, or 22.9° 2θ. In a certain embodiment, wherein the solid form has an X-ray powder diffraction pattern comprising four or more characteristic peaks at approximately 3.7, 7.3, 11.0, 18.3, or 22.9° 2θ. In a certain embodiment, the solid form has an X-ray powder diffraction pattern comprising five characteristic peaks at approximately 3.7, 7.3, 11.0, 18.3, or 22.9° 2θ. In a certain embodiment, the solid form has an X-ray powder diffraction pattern substantially as shown in FIG. 13. In a certain embodiment, the solid form has a DSC thermogram comprising an endothermic event with an onset temperature of about 96° C. and a peak maximum temperature of about 111° C. In a certain embodiment, the solid form is non-solvated.

In another embodiment, provided herein is a solid form comprising Compound 1, or a tautomer thereof:

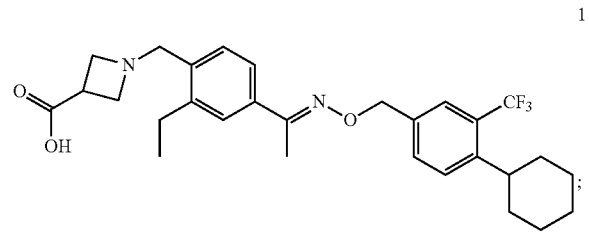 [SMILES: CCc1cc(/C(C)=N/OCc2ccc(C3CCCCC3)c(C(F)(F)F)c2)ccc1CN1CC(C(=O)O)C1]

which has an X-ray powder diffraction pattern comprising three or more characteristic peaks at approximately 3.9, 7.7, 11.6, 14.3, 20.9, or 24.5° 2θ. In a certain embodiment, the solid form has an X-ray powder diffraction pattern comprising four or more characteristic peaks at approximately 3.9, 7.7, 11.6, 14.3, 20.9, or 24.5° 2θ. In a certain embodiment, the solid form has an X-ray powder diffraction pattern comprising five or more characteristic peaks at approximately 3.9, 7.7, 11.6, 14.3, 20.9, or 24.5° 2θ. In a certain embodiment, the solid form has an X-ray powder diffraction pattern comprising six characteristic peaks at approximately 3.9, 7.7, 11.6, 14.3, 20.9, or 24.5° 2θ. In a certain embodiment, the solid form has an X-ray powder diffraction pattern substantially as shown in FIG. 17. In a certain embodiment, the solid form has a DSC thermogram comprising an endothermic event with an onset temperature of about 106° C. In a certain embodiment, the solid form is non-solvated.

In another embodiment, provided herein is a solid form comprising Compound 1, or a tautomer thereof:

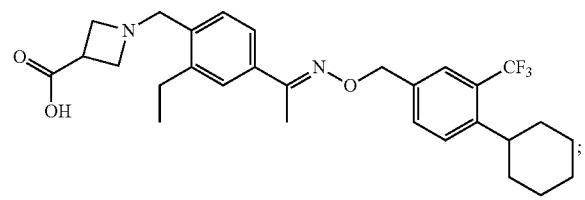

which has an X-ray powder diffraction pattern comprising three or more characteristic peaks at approximately 3.3, 9.9, 14.8, 19.9, 20.4, or 23.5° 2θ. In a certain embodiment, the solid form has an X-ray powder diffraction pattern comprising four or more characteristic peaks at approximately 3.3, 9.9, 14.8, 19.9, 20.4, or 23.5° 2θ. In a certain embodiment, the solid form has an X-ray powder diffraction pattern comprising five or more characteristic peaks at approximately 3.3, 9.9, 14.8, 19.9, 20.4, or 23.5° 2θ. In a certain embodiment, the solid form has an X-ray powder diffraction pattern comprising six characteristic peaks at approximately 3.3, 9.9, 14.8, 19.9, 20.4, or 23.5° 2θ. In a certain embodiment, the solid form has an X-ray powder diffraction pattern substantially as shown in FIG. 21. In a certain embodiment, the solid form has a DSC thermogram comprising an endothermic event with an onset temperature of about 48° C. and a peak maximum temperature of about 63° C. In a certain embodiment, the solid form is solvated by dimethyl carbonate.

In another embodiment, provided herein is a solid form comprising Compound 1, or a tautomer thereof:

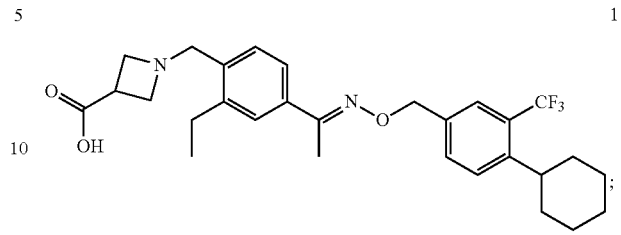

which has an X-ray powder diffraction pattern comprising three or more characteristic peaks at approximately 3.6, 7.2, 10.8, 17.8, 18.0, 18.3, or 21.7° 2θ. In a certain embodiment, the solid form has an X-ray powder diffraction pattern comprising four or more characteristic peaks at approximately 3.6, 7.2, 10.8, 17.8, 18.0, 18.3, or 21.7° 2θ. In a certain embodiment, the solid form has an X-ray powder diffraction pattern comprising five or more characteristic peaks at approximately 3.6, 7.2, 10.8, 17.8, 18.0, 18.3, or 21.7° 2θ. In a certain embodiment, the solid form has an X-ray powder diffraction pattern comprising six or more characteristic peaks at approximately 3.6, 7.2, 10.8, 17.8, 18.0, 18.3, or 21.7° 2θ. In a certain embodiment, the solid form has an X-ray powder diffraction pattern comprising seven characteristic peaks at approximately 3.6, 7.2, 10.8, 17.8, 18.0, 18.3, or 21.7° 2θ. In a certain embodiment, the solid form has an X-ray powder diffraction pattern substantially as shown in FIG. 25. In a certain embodiment, the solid form has a DSC thermogram comprising an endothermic event with a peak maximum temperature of about 56° C. and a second endothermic event with a peak maximum temperature of about 94° C. In a certain embodiment, the solid form is hydrated.

In another embodiment, provided herein is a solid form comprising Compound 1, or a tautomer thereof:

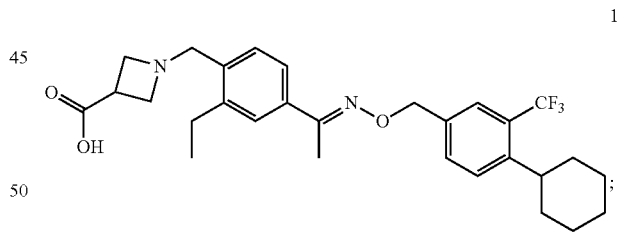

which has an X-ray powder diffraction pattern comprising three or more characteristic peaks at approximately 4.0, 12.0, 17.6, 20.1 or 21.5° 2θ. In a certain embodiment, the solid form has an X-ray powder diffraction pattern comprising four or more characteristic peaks at approximately 4.0, 12.0, 17.6, 20.1 or 21.5° 2θ. In a certain embodiment, the solid form an X-ray powder diffraction pattern comprising five characteristic peaks at approximately 4.0, 12.0, 17.6, 20.1 or 21.5° 2θ. In a certain embodiment, the solid form has an X-ray powder diffraction pattern substantially as shown in FIG. 29. In a certain embodiment, the solid form has a DSC thermogram comprising an endothermic event with a peak maximum temperature of about 54° C. and a second endothermic event with an onset temperature of about 82° C.

and a peak maximum temperature of about 93° C. In a certain embodiment, the solid form is hydrated.

In another embodiment, provided herein are pharmaceutical compositions comprising one or more of the solid forms described herein. In certain embodiments, the solid form is no less than 95% pure. In certain embodiments, the pharmaceutical composition further comprises a second solid form described herein. In certain embodiments, the pharmaceutical composition further comprises an amorphous form of Compound 1. In certain embodiments, the pharmaceutical composition further comprises a pharmaceutically acceptable excipient or carrier. In certain embodiments, the pharmaceutical composition is a single unit dosage form. In certain embodiments, the pharmaceutical composition is a tablet. In certain embodiments, the pharmaceutical composition is a capsule.

In another embodiment, provided herein is a method of treating multiple sclerosis, wherein the method comprises administering to a patient in need thereof a therapeutically effective amount of a solid form described herein. In another embodiment, provided herein is a method of treating multiple sclerosis, wherein the method comprises administering to a patient in need thereof a therapeutically effective amount of a pharmaceutical composition described herein.

In another embodiment, provided herein is a method of treating psoriasis, wherein the method comprises administering to a patient in need thereof a therapeutically effective amount of a solid form described herein. In another embodiment, provided herein is a method of treating psoriasis, wherein the method comprises administering to a patient in need thereof a therapeutically effective amount of a pharmaceutical formulation described herein.

In another embodiment, provided herein is a method of treating polymyositis, wherein the method comprises administering to a patient in need thereof a therapeutically effective amount of a solid form described herein. In another embodiment, provided herein is a method of treating polymyositis, wherein the method comprises administering to a patient in need thereof a therapeutically effective amount of a pharmaceutical formulation described herein.

In another embodiment, provided herein is a method of making a solid form comprising Compound 1, or a tautomer thereof:

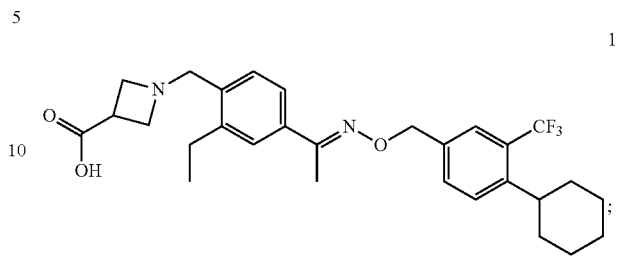

which has an X-ray powder diffraction pattern comprising at least three characteristic peaks at approximately 2.3, 3.9, 7.7, 11.5, or 20.9° 2θ, comprising:
  a) obtaining a slurry of Compound 1 in isopropyl ether;
  b) stirring the slurry for about 72 h while cycling the temperature between about 5° C. and about 40° C.; and
  c) collecting the solids from the slurry by filtration.

In another embodiment, provided herein is a method of making a solid form comprising Compound 1, or a tautomer thereof:

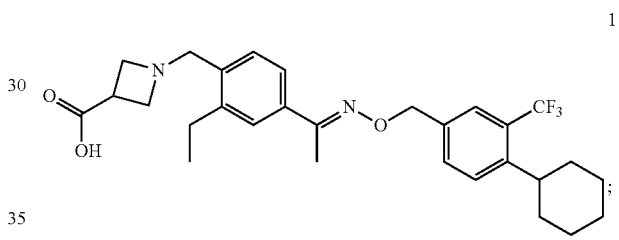

which has an X-ray powder diffraction pattern comprising at least three characteristic peaks at approximately 2.3, 2.8, 7.7, 8.4, 11.5, or 20.9° 2θ, comprising:
  a) obtaining a slurry of Compound 1 in cyclohexane;
  b) stirring the slurry for about 72 h while cycling the temperature between about 5° C. and about 40° C.; and
  c) collecting the solids from the slurry by filtration.

In another embodiment, provided herein is a method of making a solid form comprising Compound 1, or a tautomer thereof:

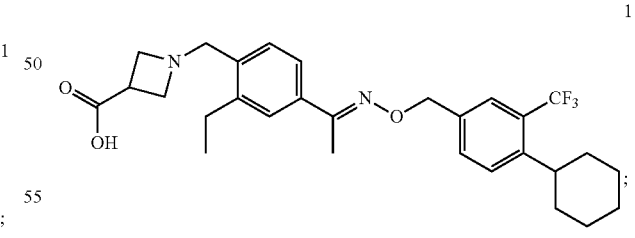

which has an X-ray powder diffraction pattern comprising at least three characteristic peaks at approximately 2.2, 3.9, 6.5, 7.7, 11.5, or 20.9° 2θ, comprising:
  a) obtaining a slurry of Compound 1 in heptane;
  b) stirring the slurry for about 72 h while cycling the temperature between about 5° C. and about 40° C.; and
  c) collecting the solids from the slurry by filtration.

In another embodiment, provided herein is a method of making a solid form comprising Compound 1, or a tautomer thereof:

which has an X-ray powder diffraction pattern comprising at least three characteristic peaks at approximately 3.7, 7.3, 11.0, 18.3, or 22.9° 2θ, comprising:
  a) obtaining a slurry of Compound 1 in dimethyl carbonate; and
  b) stirring the slurry for about 72 h while cycling the temperature between about 5° C. and about 40° C.
  c) collecting the solids from the slurry by filtration; and
  d) drying the solids with a flow of inert gas under vacuum at 65° C.

In another embodiment, provided herein is a method of making a solid form comprising Compound 1, or a tautomer thereof:

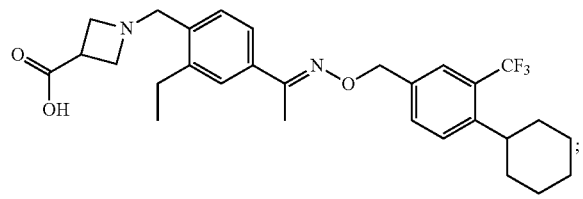

which has an X-ray powder diffraction pattern comprising at least three characteristic peaks at approximately 3.9, 7.7, 11.6, 14.3, 20.9, or 24.5° 2θ, comprising:
a) obtaining a solution of Compound 1 in isopropyl ether;
b) seeding the solution with a small amount of Form E described herein;
c) stirring the solution overnight or about 48 h while cycling the temperature between about 5° C. and about 40° C.; and
d) collecting the solids from the slurry by filtration; and
e) drying the solids with a flow of inert gas under vacuum at 65° C.

In another embodiment, provided herein is a method of making a solid form comprising Compound 1, or a tautomer thereof:

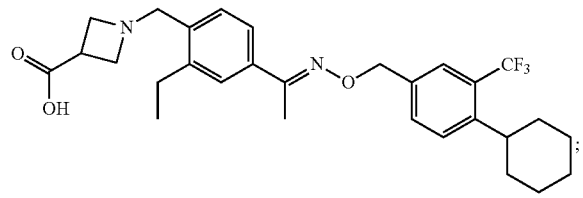

which has an X-ray powder diffraction pattern comprising characteristic peaks at approximately 3.3, 9.9, 14.8, 19.9, 20.4, or 23.5° 2θ, comprising:
a) obtaining a slurry of Compound 1 in dimethyl carbonate;
b) seeding the slurry with a small amount of Form D described herein;
c) stirring the slurry for about 12 h at 20° C.; and
d) collecting the solids from the slurry by centrifugation followed by decanting and drying.

In another embodiment, provided herein is a method of making a solid form comprising Compound 1, or a tautomer thereof:

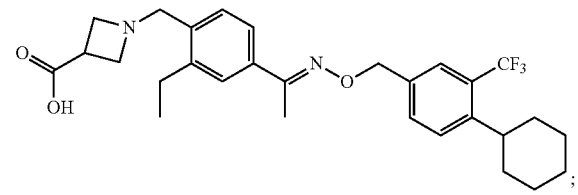

which has an X-ray powder diffraction pattern comprising at least three characteristic peaks at approximately 3.6, 7.2, 10.8, 17.8, 18.0, 18.3, or 21.7° 2θ, comprising:
a) obtaining a slurry of Form E of Compound 1 in dimethyl carbonate;
b) seeding the slurry with a small amount of Form D or Form I described herein;
c) stirring the slurry for about 48 h while cycling the temperature between about 5° C. and about 30° C.; and
d) collecting the solids from the slurry by filtration.

In another embodiment, provided herein is a method of making a solid form comprising Compound 1, or a tautomer thereof:

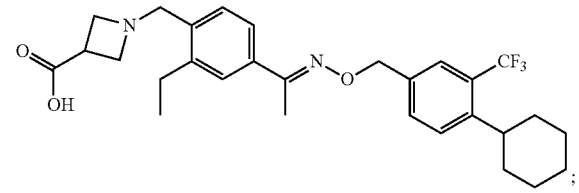

which has an X-ray powder diffraction pattern comprising at least three characteristic peaks at approximately 4.0, 12.0, 17.6, 20.1 or 21.5° 2θ, comprising:
a) obtaining a saturated solution of Compound 1 in dimethylformamide;
b) adding water into the saturated solution at an ambient temperature;
c) stirring the slurry for about 4 days while cycling the temperature between about 20° C. and about 50° C.; and
d) evaporating the mixture under a flow of nitrogen gas at ambient temperature over 14 days.

In another embodiment, provided herein is a solid form comprising Compound 1, or a tautomer thereof:

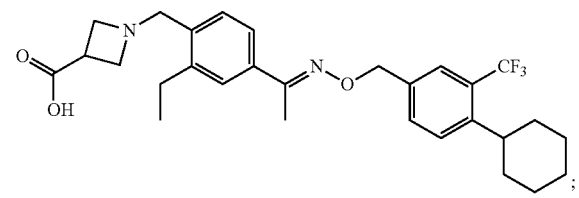

which has an X-ray powder diffraction pattern comprising three or more characteristic peaks at approximately 7.9, 11.9, 13.4, 15.7, 17.4, or 20.0° 2θ. In certain embodiments, the solid form has an X-ray powder diffraction pattern comprising four or more characteristic peaks at approximately 7.9, 11.9, 13.4, 15.7, 17.4, or 20.0° 2θ. In certain embodiments, the solid form has an X-ray powder diffraction pattern comprising five or more characteristic peaks at approximately 7.9, 11.9, 13.4, 15.7, 17.4, or 20.0° 2θ. In certain embodiments, the solid form has an X-ray powder diffraction pattern comprising six or more characteristic peaks at approximately 7.9, 11.9, 13.4, 15.7, 17.4, or 20.0° 2θ. In certain embodiments, the solid form has an X-ray powder diffraction pattern substantially as shown in FIG. 33. In certain embodiments, the solid form has a DSC thermogram comprising an endothermic event with an onset temperature of 143.4° C.

In another embodiment, provided herein is a solid form comprising Compound 1, or a tautomer thereof:

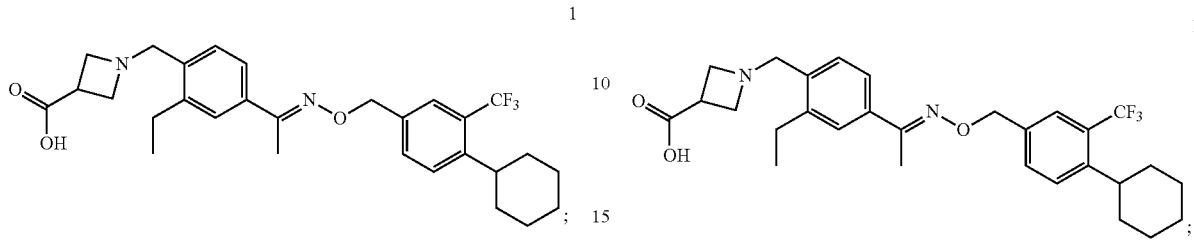

which has an X-ray powder diffraction pattern comprising three or more characteristic peaks at approximately 7.3, 8.0, 10.0, 10.9, 12.0, 17.5, or 20.1° 2θ. In certain embodiments, the solid form has an X-ray powder diffraction pattern comprising four or more characteristic peaks at approximately 7.3, 8.0, 10.0, 10.9, 12.0, 17.5, or 20.1° 2θ. In certain embodiments, the solid form has an X-ray powder diffraction pattern comprising five or more characteristic peaks at approximately 7.3, 8.0, 10.0, 10.9, 12.0, 17.5, or 20.1° 2θ. In certain embodiments, the solid form has an X-ray powder diffraction pattern comprising six or more characteristic peaks at approximately 7.3, 8.0, 10.0, 10.9, 12.0, 17.5, or 20.1° 2θ. In certain embodiments, the solid form has an X-ray powder diffraction pattern substantially as shown in FIG. 36. In certain embodiments, the solid form has a DSC thermogram comprising endothermic events with peak maximum temperatures of approximately 98.9° C. and 113.7° C., respectively.

In another embodiment, provided herein is a solid form comprising Compound 1, or a tautomer thereof:

which has an X-ray powder diffraction pattern comprising three or more characteristic peaks at approximately 11.5, 12.0, 13.4, 17.5, 20.1, or 21.3° 2θ. In certain embodiments, the solid form has an X-ray powder diffraction pattern comprising four or more characteristic peaks at approximately 11.5, 12.0, 13.4, 17.5, 20.1, or 21.3° 2θ. In certain embodiments, the solid form has an X-ray powder diffraction pattern comprising five or more characteristic peaks at approximately 11.5, 12.0, 13.4, 17.5, 20.1, or 21.3° 2θ. In certain embodiments, the solid form has an X-ray powder diffraction pattern comprising six or more characteristic peaks at approximately 11.5, 12.0, 13.4, 17.5, 20.1, or 21.3° 2θ. In certain embodiments, the solid form has an X-ray powder diffraction pattern substantially as shown in FIG. 38.

In another embodiment, provided herein is a solid form comprising Compound 1, or a tautomer thereof:

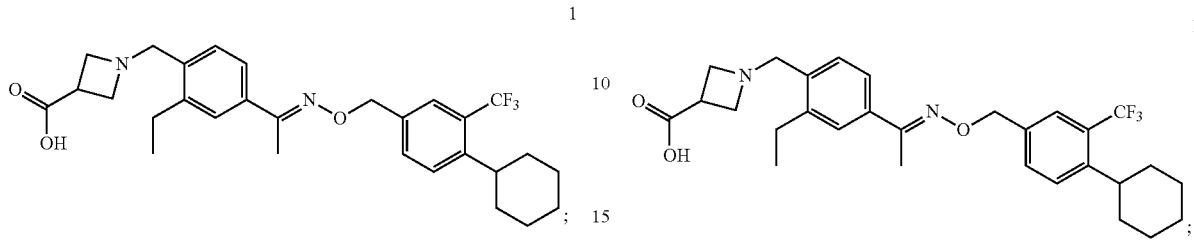

which has an X-ray powder diffraction pattern comprising three or more characteristic peaks at approximately 7.2, 9.5, 12.0, 16.4, 18.2, or 22.8° 2θ. In certain embodiments, the solid form has an X-ray powder diffraction pattern comprising four or more characteristic peaks at approximately 7.2, 9.5, 12.0, 16.4, 18.2, or 22.8° 2θ. In certain embodiments, the solid form has an X-ray powder diffraction pattern comprising five or more characteristic peaks at approximately 7.2, 9.5, 12.0, 16.4, 18.2, or 22.8° 2θ. In certain embodiments, the solid form has an X-ray powder diffraction pattern comprising six or more characteristic peaks at approximately 7.2, 9.5, 12.0, 16.4, 18.2, or 22.8° 2θ. In certain embodiments, the solid form has an X-ray powder diffraction pattern substantially as shown in FIG. 40.

In certain embodiments, provided herein is a solid form comprising Compound 1, or a tautomer thereof:

which has an X-ray powder diffraction pattern comprising three or more characteristic peaks at approximately 12.0, 13.5, 17.7, 20.1, 21.6, or 23.7° 2θ. In certain embodiments, the solid form has an X-ray powder diffraction pattern comprising four or more characteristic peaks at approximately 12.0, 13.5, 17.7, 20.1, 21.6, or 23.7° 2θ. In certain embodiments, the solid form has an X-ray powder diffraction pattern comprising five or more characteristic peaks at approximately 12.0, 13.5, 17.7, 20.1, 21.6, or 23.7° 2θ. In certain embodiments, the solid form has an X-ray powder diffraction pattern comprising six or more characteristic peaks at approximately 12.0, 13.5, 17.7, 20.1, 21.6, or 23.7° 2θ. In certain embodiments, the solid form has an X-ray powder diffraction pattern substantially as shown in FIG. 42. In certain embodiments, the solid form has a DSC thermogram comprising an endothermic event with an onset temperature of approximately 85.7° C.

In another embodiment, provided herein is a method of making a solid form comprising Compound 1, or a tautomer thereof:

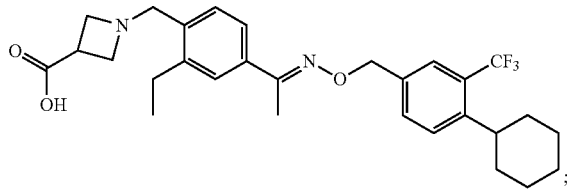

which has an X-ray powder diffraction pattern comprising at least three characteristic peaks at approximately 7.9, 11.9, 13.4, 15.7, 17.4, or 20.0° 2θ, comprising:

a) mixing Compound 1 with ethyl methyl ketone;

b) sonicating for 5 minutes;

c) filtering via 0.2 μm PTFE-membraned syringe filter;

d) evaporating the filtrate to dryness under nitrogen purge;

e) adding ethyl methyl ketone to the sample;

f) capping the sample and stirring at 500 rotations per minute for about a day; and g) collecting solids from the sample by filtration and drying the collected solids in a vacuum oven at 35° C. for about a day.

In another embodiment, provided herein is a method of making a solid form comprising Compound 1, or a tautomer thereof:

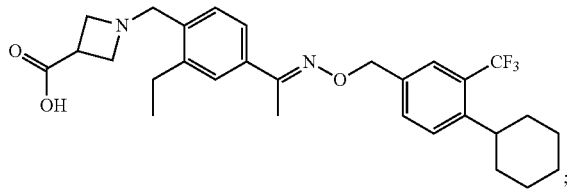

which has an X-ray powder diffraction pattern comprising at least three characteristic peaks at approximately 7.3, 8.0, 10.0, 10.9, 12.0, 17.5, or 20.1° 2θ, comprising:

a) drying Compound 1 in a vacuum oven at 35° C. for 3 hours;

b) adding ethyl methyl ketone to the sample;

c) filtering via 0.2 μm PTFE-membraned syringe filter;

d) evaporating the filtrate under nitrogen purge until precipitates were observed;

e) capping the sample and stirring at 500 rotations per minute for about a day; and f) collecting solids from the sample by filtration and drying the collected solids in a vacuum oven at 35° C. for about a day.

In another embodiment, provided herein is a method of making a solid form comprising Compound 1, or a tautomer thereof:

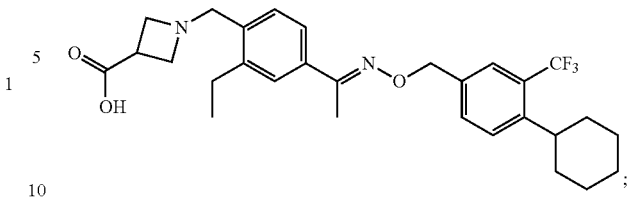

which has an X-ray powder diffraction pattern comprising at least three characteristic peaks at approximately 11.5, 12.0, 13.4, 17.5, 20.1, or 21.3° 2θ, comprising:

a) drying Form K of Compound 1 in a vacuum oven at 35° C. for about two days; and b) heating the sample to 121° C. at 10° C. per minute in a crimped pan with a pin hole on its lid.

In another embodiment, provided herein is a method of making a solid form comprising Compound 1, or a tautomer thereof:

which has an X-ray powder diffraction pattern comprising at least three characteristic peaks at approximately 7.2, 9.5, 12.0, 16.4, 18.2, or 22.8° 2θ, comprising:

a) drying Form K of Compound 1 in a vacuum oven at 35° C. for about two days; and b) heating the sample to 102° C. at 10° C. per minute in a crimped pan with a pin hole on its lid.

In another embodiment, provided herein is a method of making a solid form comprising Compound 1, or a tautomer thereof:

which has an X-ray powder diffraction pattern comprising at least three characteristic peaks at approximately 12.0, 13.5, 17.7, 20.1, 21.6, or 23.7° 2θ, comprising:

a) mixing Form E of Compound 1 with Milli-Q water;

b) capping the sample and stirring at 400 rotations per minute for about 5 days; and c) collecting solids from the sample by filtration and drying the collected solids in a vacuum oven at 35° C. for about a day.

4. BRIEF DESCRIPTION OF THE DRAWINGS

5. DETAILED DESCRIPTION

5.1 Definitions

Figure 1:
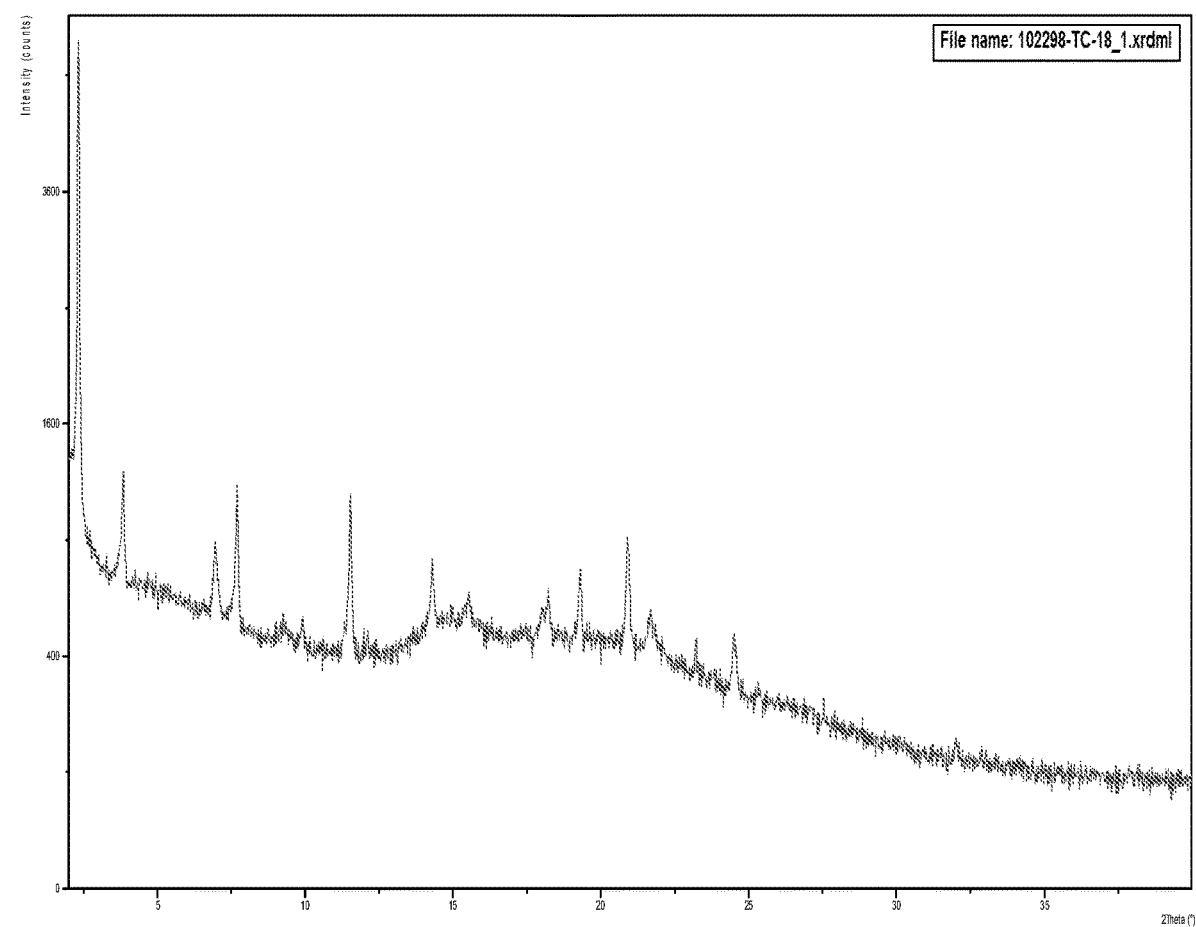
FIG. 1 depicts a PXRD pattern of Form A of Compound 1.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, infrared (IR) or Raman spectroscopy or X-ray powder diffractometry (PXRD); indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), PXRD, single-crystal X-ray diffractometry, vibrational spectroscopy, e.g., IR and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of a PXRD peak position may vary by up to ±0.2 degrees two theta while still describing the particular PXRD peak.

As used herein, and unless otherwise specified, a crystalline that is "pure," i.e., substantially free of other crystalline or amorphous solid forms, contains less than about 10% by weight of one or more other crystalline or amorphous solid forms, less than about 5% by weight of one or more other crystalline or amorphous solid forms, less than about 3% by weight of one or more other crystalline or amorphous solid forms, or less than about 1% by weight of one or more other crystalline or amorphous solid forms.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, $23^{rd}$ ed., 1843-1844 (1995).

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition.

As used herein, and unless otherwise indicated, the term "desolvated solvate" refers to a solid form of a substance which can be made by removing the solvent from a solvate. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

As used herein, and unless otherwise indicated, the term "composition" is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

As used herein, and unless otherwise indicated, the term "solid form" refers to a physical form which is not predominantly in a liquid or a gaseous state. The terms "solid type" and "type" are used interchangeably herein with "solid form". As used herein and unless otherwise specified, the term "solid form," refers to Compound 1, refers to a physical form comprising Compound 1 which is not predominantly in a liquid or a gaseous state. A solid form may be a crystalline form or a mixture thereof. In certain embodiments, a solid form may be a liquid crystal. In certain embodiments, the term "solid forms comprising Compound 1" includes crystal forms comprising Compound 1. In certain embodiments, the solid form of Compound 1 is Form A, Form B, Form C, Form D, Form E, Form F, Form G, Form H, Form I, the amorphous solid, or a mixture thereof. In certain embodiments, the solid form of Compound 1 is Form A, Form B, Form C, Form D, Form E, Form F, Form G, Form H, Form I, Form J, Form K, Form L, Form M, Form N, the amorphous solid, or a mixture thereof.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, $23^{rd}$ ed., 1843-1844 (1995).

As used herein and unless otherwise specified the term "crystal form" or "crystalline form" refers to a solid form that is crystalline. In certain embodiments, a crystal form of a substance may be substantially free of amorphous solids and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous solids and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

As used herein and unless otherwise specified, the term "amorphous" or "amorphous solid form" means that the substance, component, or product in question is not substantially crystalline as determined by X-ray diffraction. In particular, the term "amorphous solid" describes a disordered solid form, i.e., a solid form lacking long range crystalline order. In certain embodiments, an amorphous solid form of a substance may be substantially free of other amorphous solid form and/or crystal forms. In certain embodiments, an amorphous solid form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous solid forms and/or crystal forms on a weight basis. In certain embodiments, an amorphous solid form of a substance may be physically and/or chemically pure. In certain embodiments, an amorphous solid form of a substance be about 99%, about 98%, about 97%, about 96%, about 95%, about 94%, about 93%, about 92%, about 91%, or about 90% physically and/or chemically pure.

As used herein, and unless otherwise indicated, the term "tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

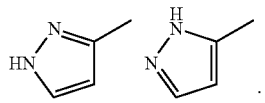

As readily understood by one skilled in the art, a wide variety of functional groups and other structures may exhibit tautomerism and all tautomers of Compound 1 are within the scope of the present invention.

As used herein, and unless otherwise indicated, the term "zwitterion(s)" means compound(s) containing both a basic moiety, including but not limited to, for example, pyridine and imidazole; and an acidic moiety including but not limited to, for example, a carboxylic acid.

As used herein, and unless otherwise indicated, the term "treating" means an alleviation, in whole or in part, of the disease or disorder, or symptoms associated with the disease or disorder, or slowing, or halting of further progression or worsening of the disease or disorder, or symptoms associated with the disease or disorder.

As used herein, and unless otherwise indicated, the term "preventing" means prevention of the onset, recurrence, or spread of the disease or disorder, or symptoms associated with the disorder or disease, in a patient at risk for developing the disease or disorder.

As used herein, and unless otherwise specified, the term "therapeutically effective amount" of a compound refers to an amount sufficient to provide a therapeutic benefit in the treatment or management of the disease or to delay or minimize one or more symptoms associated with the disease. Further, a therapeutically effective amount of a compound means that amount of therapeutic agent alone, or in combination with other therapies, provides a therapeutic benefit in the treatment or management of the disease. The term "therapeutically effective amount" can encompass an amount that improves overall therapy, reduces or avoids symptoms or causes of disease, or enhances the therapeutic efficacy of another therapeutic agent.

As used herein, and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human, in another embodiment a cell from any one of the foregoing animals. In one embodiment, a subject or patient is a non-human animal, in another embodiment a non-human mammal. In another embodiment, a subject or patient is a human having or at risk for having an autoimmune or chronic inflammatory disease. In certain embodiments, the autoimmune or chronic inflammatory disease is polymyositis, dermatomyositis, lupus nephritis, rheumatoid arthritis, inflammatory bowel disease, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease or multiple sclerosis. In certain embodiments, provided herein are methods for treating a subject suffering from or at risk for having relapsing-remitting multiple sclerosis, primary progressive multiple sclerosis, secondary progressive multiple sclerosis, and relapsing secondary progressive multiple sclerosis. In certain embodiments, a subject or patient is a human having or at risk for having a neurological disorder. In certain embodiments, the neurological disorder is Rett Syndrome. In certain embodiments, a subject or patient is a human having or at risk for having renal or hepatic impairment. In certain embodiments, a subject or patient is a human having or at risk for having a disease or disorder associated with sphingosine 1-phosphate, including but not limited to multiple sclerosis, relapse-remitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, and Graves' disease. In certain embodiments, a subject or patient is a human having or at risk for having a disease or disorder associated with the interferon alpha receptor 1, including but not limited to psoriasis, ulcerative colitis, systemic lupus, multiple sclerosis, and rheumatoid arthritis. In certain embodiments, a subject or patient is a human having a disease or disorder mediated by lymphocyte interactions, such as, for example, in transplantation, such as acute or chronic rejection of cell, tissue or organ allo- or xenografts or delayed graft function, graft versus host disease; autoimmune diseases, e.g., rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g., allergic asthma, atopic dermatitis, allergic rhinitis/conjunctivitis, allergic contact dermatitis; inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g., myocardial infarction, stroke, gut ischemia, renal failure or hemorrhage shock, traumatic shock; T cell lymphomas or T cell leukemias; infectious diseases, e.g., toxic shock (e.g., superantigen induced), septic shock, adult respiratory distress syndrome or viral infections, e.g., AIDS, viral hepatitis, chronic bacterial infection; muscle diseases, e.g., polymyositis; or senile dementia. Examples of cell, tissue or solid organ transplants include, e.g., pancreatic islets, stem cells, bone marrow, corneal tissue, neuronal tissue, heart, lung, combined heart-lung, kidney, liver, bowel, pancreas, trachea or oesophagus.

Unless otherwise specified, to the extent that there is a discrepancy between a depicted chemical structure of a compound provided herein and a chemical name of a compound provided herein, the chemical structure shall control.

5.2 Compound 1

The solid forms, formulations and methods of use provided herein relate to solid forms (e.g., crystalline forms, amorphous forms, polymorphs or mixtures thereof)) comprising Compound 1:

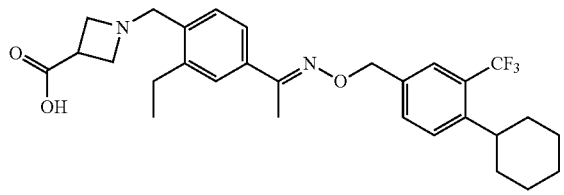

1 having the name (E)-1-(4-(1-(((4-cyclohexyl-3-(trifluoromethyl)benzyl)oxy)imino)ethyl)-2-ethylbenzyl)azetidine-3-carboxylic acid, including tautomers thereof. Compound 1 can be prepared by methods known in the art. See, e.g., International Patent Application Publication No. WO 2013/113915 A1.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Solid Forms of Compound 1

In certain embodiments, provided herein are solid forms comprising Compound 1, or a tautomer thereof. In certain embodiments, the solid form is crystalline. In certain embodiments, the solid form is a single-component solid form. In certain embodiments, the solid form is a hydrate. In certain embodiments, the solid form is an anhydrate. In certain embodiments, the solid form is a solvate. In certain embodiments, the solid form is non-solvated.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The solid forms comprising Compound 1, or a tautomer thereof, provided herein (e.g., Form A, Form B, Form C, Form D, Form E, Form F, Form G, Form H, and Form I) may be characterized using a number of methods known to a person skilled in the art, including, but not limited to, single crystal X-ray diffraction, X-ray powder diffraction (PXRD), microscopy (e.g., optical microscopy, scanning electron microscopy (SEM)), thermal analysis (e.g., differential scanning calorimetry (DSC), thermal gravimetric analysis (TGA), and hot-stage microscopy), dynamic vapor sorption (DVS), spectroscopy (e.g., infrared, Raman, and nuclear magnetic resonance), high performance liquid chromatography (HPLC). The particle size and size distribution of the solid form provided herein may be determined by conventional methods, such as laser light scattering technique.

The solid forms comprising Compound 1, or a tautomer thereof, provided herein (e.g., Form A, Form B, Form C, Form D, Form E, Form F, Form G, Form H, Form I, Form J, Form K, Form L, Form M, and Form N) may be characterized using a number of methods known to a person skilled in the art, including, but not limited to, single crystal X-ray diffraction, X-ray powder diffraction (PXRD), microscopy (e.g., optical microscopy, scanning electron microscopy (SEM)), thermal analysis (e.g., differential scanning calorimetry (DSC), thermal gravimetric analysis (TGA), and hot-stage microscopy), dynamic vapor sorption (DVS), spectroscopy (e.g., infrared, Raman, and nuclear magnetic resonance), high performance liquid chromatography (HPLC). The particle size and size distribution of the solid form provided herein may be determined by conventional methods, such as laser light scattering technique.

The purity of the solid forms provided herein may be determined by standard analytical methods, such as thin layer chromatography (TLC), gel electrophoresis, gas chromatography, high performance liquid chromatography (HPLC), and mass spectrometry.

It should be understood that the numerical values of the peaks of an X-ray powder diffraction pattern may vary slightly from one machine to another or from one sample to another, and so the values quoted are not to be construed as absolute, but with an allowable variability, such as ±0.2° 2θ or ±0.1° 2θ (see, United States Pharmacopoeia, page 2228 (2003)).

(a) Methods of Preparing Solid Forms Comprising Compound 1

In certain embodiments, provided herein are methods for making a solid form comprising Compound 1, or a tautomer thereof, comprising 1) obtaining a slurry of Compound 1 in a solvent or solvent system; 2) stirring the slurry for a period of time (e.g., about 72 h) while cycling the temperature (e.g., between about 5° C. and about 40° C.); and 3) collecting solids from the slurry by filtration and optionally drying the collected solids to yield a solid form comprising Compound 1. In certain embodiments, the methods for making a solid form comprising Compound 1 are equilibration experiments, such as slurry experiments. In certain embodiments, the solvent is isopropyl ether, cyclohexane, heptanes, dimethyl carbonate, or water. In certain embodiments, the collected solids are dried using a flow of an inert gas, such as nitrogen or argon. In certain embodiments, the collected solids are dried under vacuum at a certain temperature (e.g., 65° C.). In a particular embodiment, the collected solids are dried using a combination of a flow of an inert gas, such as nitrogen or argon, under vacuum at a certain temperature (e.g., 65° C.).

In certain embodiments, provided herein are methods for making a solid form comprising Compound 1, or a tautomer thereof, comprising 1) dissolving Compound 1 in a solvent or solvent system to yield a solution; 2) filtering the solution if Compound 1 does not dissolve completely; 3) evaporating the supernatant at a certain temperature (e.g., ambient temperature) over a period of time (e.g., 14 days) to yield a solid form comprising Compound 1. In certain embodiments, the evaporation step further comprises evaporating the solution under an inert gas, such as nitrogen or argon. In certain embodiments, the solvent system is dimethylformamide/water (1:2). In certain embodiments, the methods for making a solid form comprising Compound 1 are evaporation experiments.

In certain embodiments, provided herein are methods for making a solid form comprising Compound 1, or a tautomer thereof, comprising 1) obtaining a solution of Compound 1 in a solvent or solvent system at a first temperature (e.g., about 40° C.); 2) filtering the solution if there is precipitation and isolating the solids; 3) cooling the filtered solution slowly to a second temperature (e.g., about 4° C.) over a period of time (e.g., 7 days); and 5) isolating solids from the solution and optionally drying the isolated solids to yield a solid form comprising Compound 1. In certain embodiments, the solvent system is methyl isobutyl ketone/heptane (1:2). In certain embodiments, the methods for making a solid form comprising Compound 1 are cooling recrystallization experiments.

In certain embodiments, provided herein are methods for making a solid form comprising Compound 1, or a tautomer thereof, comprising 1) obtaining a solution of Compound 1 in a solvent or solvent system at a first temperature (e.g., ambient temperature); 2) adding an anti-solvent into the saturated solution at the first temperature; 3) stirring the solution for a period of time (e.g., overnight); 4) cycling the temperature (e.g., between about 20° C. and about 50° C.) for a period of time (e.g., 4 days); 5) collecting a solid and isolating the solids; 6) evaporating the remaining solution, oil or gum under a flow of nitrogen gas at a certain temperature (e.g., ambient temperature) over a period of time (e.g., 14 days) to yield a solid form comprising Compound 1. In certain embodiments, the solvent is dimethylformamide and the anti-solvent is water. In certain embodiments, the solvent is 2-propanol and the anti-solvent is water.

In certain embodiments, provided herein are methods for making a solid form comprising Compound 1, or a tautomer thereof, comprising 1) obtaining a slurry of Compound 1 in a solvent or solvent system; 2) seeding the slurry with a small amount of a solid form described herein (e.g., Form D or Form I); 3) stirring the slurry for a period of time (e.g., 2 days) while cycling the temperature (e.g., between about 5° C. and 30° C.); and 4) collecting solids from the slurry by centrifugation followed by decanting, washing and drying in a centrifuge evaporator to yield a solid form comprising Compound 1. In certain embodiments, the solvent is water.

In certain embodiments, the solvent is nitromethane, acetonitrile, acetonitrile/water (9:1), octane/ethyl acetate (9:1), acetone/water (4:1), water/1-propanol (9:1), acetonitrile/toluene (9:1), isopropyl ether/acetonitrile (1:2), octane/acetone (9:1), acetonitrile/methyl t-butyl ether (9:1), or acetonitrile/methyl isobutyl ketone (9:1).

In certain embodiments, provided herein are methods for making a solid form comprising Compound 1, or a tautomer thereof, comprising 1) mixing Compound 1 with a solvent or solvent system; 2) sonicating the mixture; 3) filtering the mixture; 4) evaporating the filtrate to dryness; 5) adding solvent to the dried sample to obtain a clear solution; 6) stirring the solution at a certain temperature for a certain time; 7) filtering the mixture; and 8) drying the resulting solid in a vacuum oven to yield a solid form comprising Compound 1. In certain embodiments, the solvent is ethyl methyl ketone. In certain embodiments, the certain temperature is ambient temperature and the certain time is about one day.

In certain embodiments, provided herein are methods for making a solid form comprising Compound 1, or a tautomer thereof, comprising 1) drying Compound 1 in a vacuum oven; 2) mixing the dried Compound 1 with a solvent or solvent system; 3) filtering the mixture; 4) evaporating the filtrate until precipitates are visually observed; 5) stirring the resulting mixture at a certain temperature for a certain time; 6) filtering the mixture; and 7) drying the resulting solid in a vacuum oven to yield a solid form comprising Compound 1. In certain embodiments, the solvent is ethyl methyl ketone. In certain embodiments, the certain temperature is ambient temperature and the certain time is about one day.

In certain embodiments, provided herein are methods for making a solid form comprising Compound 1, or a tautomer thereof, comprising 1) drying a solid form of Compound 1 described herein (e.g., Form K) in a vacuum oven at a certain temperature for a certain time; 2) heating a portion of the dried solid at a certain rate on DSC in a vessel to yield a solid form comprising Compound 1. In certain embodiments, the certain temperature is 35° C. and the certain time is two days. In certain embodiments, the portion of the dried solid is heated to 121° C. at a rate of 10° C./min. In certain embodiments, the portion of the dried solid is heated to 102° C. at a rate of 10° C./min. In certain embodiments, the vessel is a crimped aluminum pan with a pin hole on its lid.

In certain embodiments, provided herein are methods for making a solid form comprising Compound 1, or a tautomer thereof, comprising 1) mixing a solid form of Compound 1 described herein (e.g., Form E) with a solvent or solvent system; 2) stirring the resulting mixture at a certain temperature for a certain time; 3) filtering the mixture; and 4) drying the resulting solid in a vacuum oven to yield a solid form comprising Compound 1. In certain embodiments, the solvent is water. In some embodiments, the water is Milli-Q water. In certain embodiments, the certain temperature is ambient temperature and the certain time is five days.

(b) Form A

In certain embodiments, provided herein is Form A.

In one embodiment, Form A is a solid form of Compound 1. In one embodiment, Form A is solvated by isopropyl ether. In one embodiment, Form A is crystalline. In one embodiment, Form A is moderately crystalline.

In certain embodiments, provided herein are methods for making Form A, comprising: 1) obtaining a slurry of Compound 1 in a solvent or solvent system; 2) stirring the slurry for a period of time (e.g., about 72 h) while cycling the temperature (e.g., between about 5° C. and about 40° C.); and 3) collecting solids from the slurry by filtration and optionally drying the collected solids to yield Form A of Compound 1. In certain embodiments, the solvent is isopropyl ether, cyclohexane, heptanes, dimethyl carbonate, or water. In a particular embodiment, the solvent is isopropyl ether.

Figure 2:
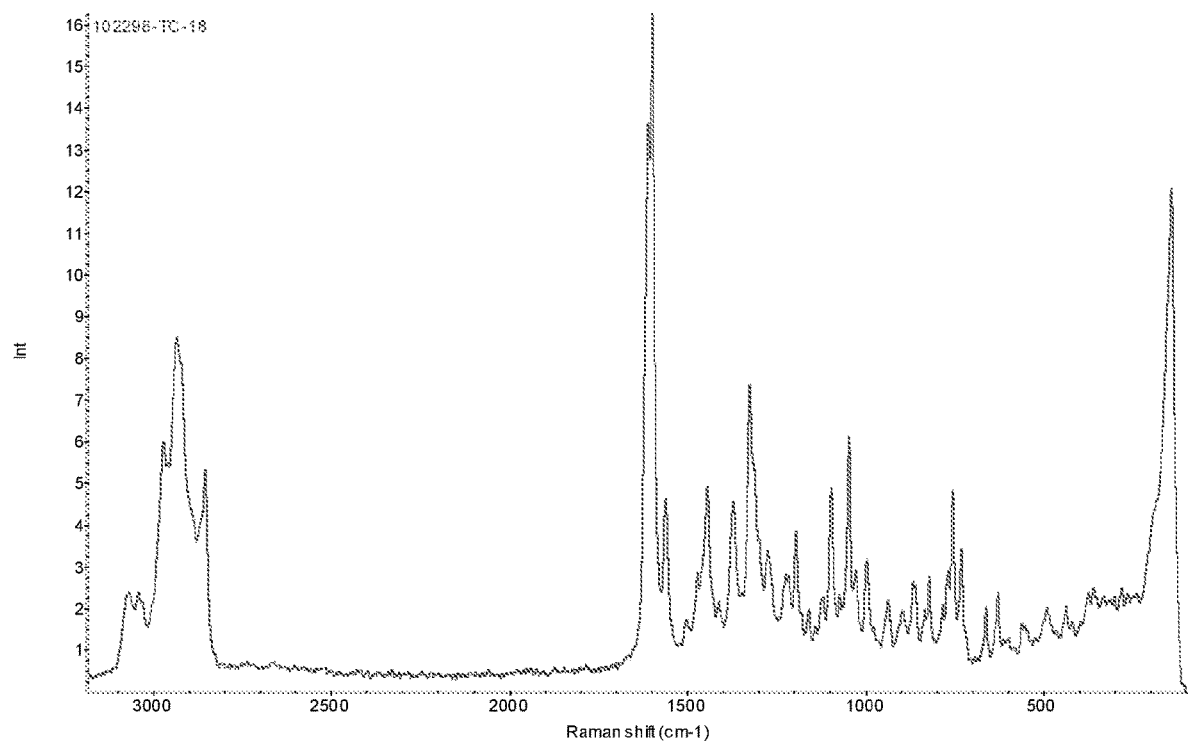
FIG. 2 depicts an FT-Raman spectrum of Form A of Compound 1.

In one embodiment, provided herein is Form A having an FT-Raman Spectrum as depicted in FIG. 2.

Figure 3:
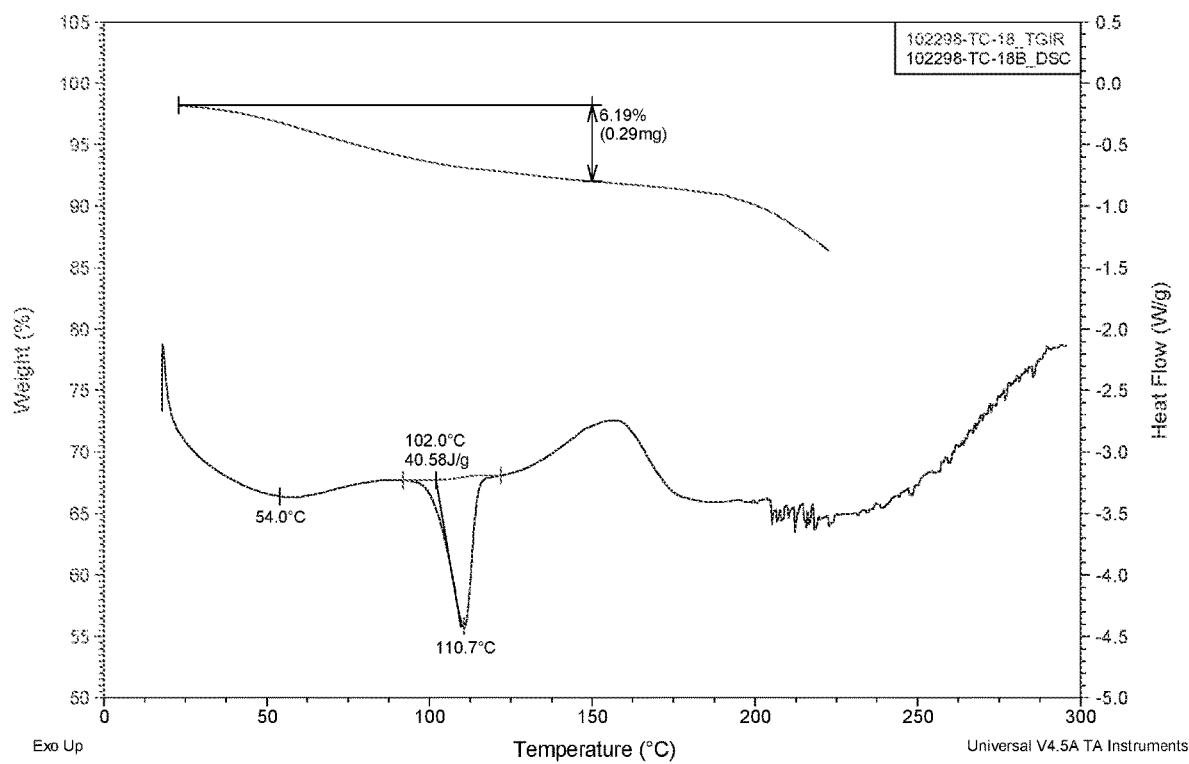
FIG. 3 depicts differential scanning calorimetry/thermal gravimetric analysis of Form A of Compound 1.
Figure 4:
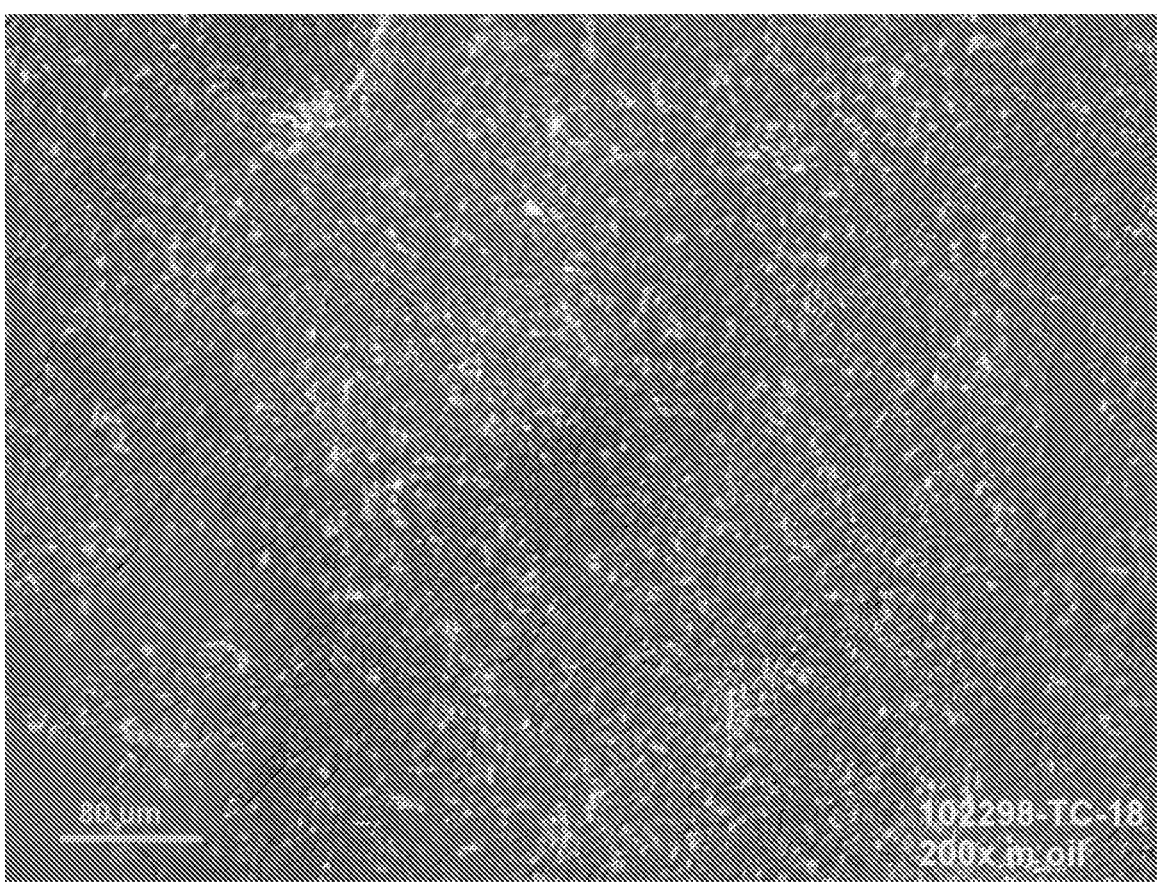
FIG. 4 depicts polarized-light microscopy of Form A of Compound 1.

In one embodiment, provided herein is a solid form, e.g., Form A of Compound 1, having a DSC thermograph substantially as depicted in FIG. 3 comprising an endothermic event with a peak maximum temperature of about 54° C. In one embodiment, provided herein is a solid form, e.g., Form A of Compound 1, having a DSC endothermic event with an onset temperature of about 102° C. when heated to 300° C.

In one embodiment, provided herein is a solid form, e.g., Form A of Compound 1, having a TGA thermogram corresponding substantially to the representative TGA thermogram as depicted in FIG. 3. In certain embodiments, the crystalline form exhibits a TGA thermogram comprising a total mass loss of approximately 6.2% of the total mass of the sample when heated from approximately 25° C. to approximately 150° C. Thus, in certain embodiments, the crystalline form loses about 6.2% its total mass when heated from about ambient temperature to about 150° C.

In certain embodiments, a solid form provided herein, e.g., Form A, is substantially crystalline, as indicated by, e.g., X-ray powder diffraction measurements. In one embodiment, provided herein is a solid form having an X-ray powder diffraction pattern (XRPD) substantially as shown in FIG. 1 (e.g., Form A). In one embodiment, a solid form provided herein, e.g., Form A, has one or more characteristic X-ray powder diffraction peaks at approximately 2.3, 3.9, 6.9, 7.7, 9.2, 9.9, 11.5, 12.1, 14.3, 15.5, 18.2, 19.3, 20.9, 21.7, 23.2, 24.5, or 32.0° 2θ (±0.2° 2θ) or (±0.1° 2θ) as depicted in FIG. 1. In a specific embodiment, a solid form provided herein, e.g., Form A, has one, two, three, four, or five characteristic X-ray powder diffraction peaks at approximately 2.3, 3.9, 7.7, 11.5, or 20.9° 2θ (±0.2° 2θ). In certain embodiments, the solid form is Form A.

In still another embodiment, Form A is substantially pure. In certain embodiments, the substantially pure Form A is substantially free of other solid forms, including but not limited to amorphous solid. In certain embodiments, the substantially pure Form A is substantially free of Form B, Form C, Form D, Form E, Form F, Form G, Form H, or Form I. In certain embodiments, the purity of the substantially pure Form A is no less than about 95%, no less than about 96%, no less than about 97%, no less than about 98%, no less than about 98.5%, no less than about 99%, no less than about 99.5%, or no less than about 99.8%. In certain embodiments, the substantially pure Form A is substantially free of Form J, Form K, Form L, Form M, or Form N.

In certain embodiments, Form A is mixed with other solid forms, including but not limited to the amorphous solid. In certain embodiments, Form A is mixed with at least one of Form B, Form C, Form D, Form E, Form F, Form G, Form H, or Form I. In certain embodiments, Form A is mixed with at least one of Form B, Form C, Form D, Form E, Form F, Form G, Form H, Form I, Form J, Form K, Form L, Form M, or Form N.

In one embodiment, Form A comprises a free base of Compound 1. In one embodiment, Form A comprises a free acid of Compound 1. In one embodiment, Form A comprises a zwitterion of Compound 1.

(c) Form B

In certain embodiments, provided herein is Form B.

In one embodiment, Form B is a solid form comprising Compound 1. In one embodiment, Form B is solvated by cyclohexane. In one embodiment, Form B is crystalline. In one embodiment, Form B is moderately crystalline.

In certain embodiments, provided herein are methods for making Form B, comprising: 1) obtaining a slurry of Compound 1 in a solvent or solvent system; 2) stirring the slurry for a period of time (e.g., about 72 h) while cycling the temperature (e.g., between about 5° C. and about 40° C.); and 3) collecting solids from the slurry by filtration and optionally drying the collected solids to yield Form B of Compound 1. In certain embodiments, the solvent is isopropyl ether, cyclohexane, heptanes, dimethyl carbonate, or water. In a particular embodiment, the solvent is cyclohexane.

Figure 6:
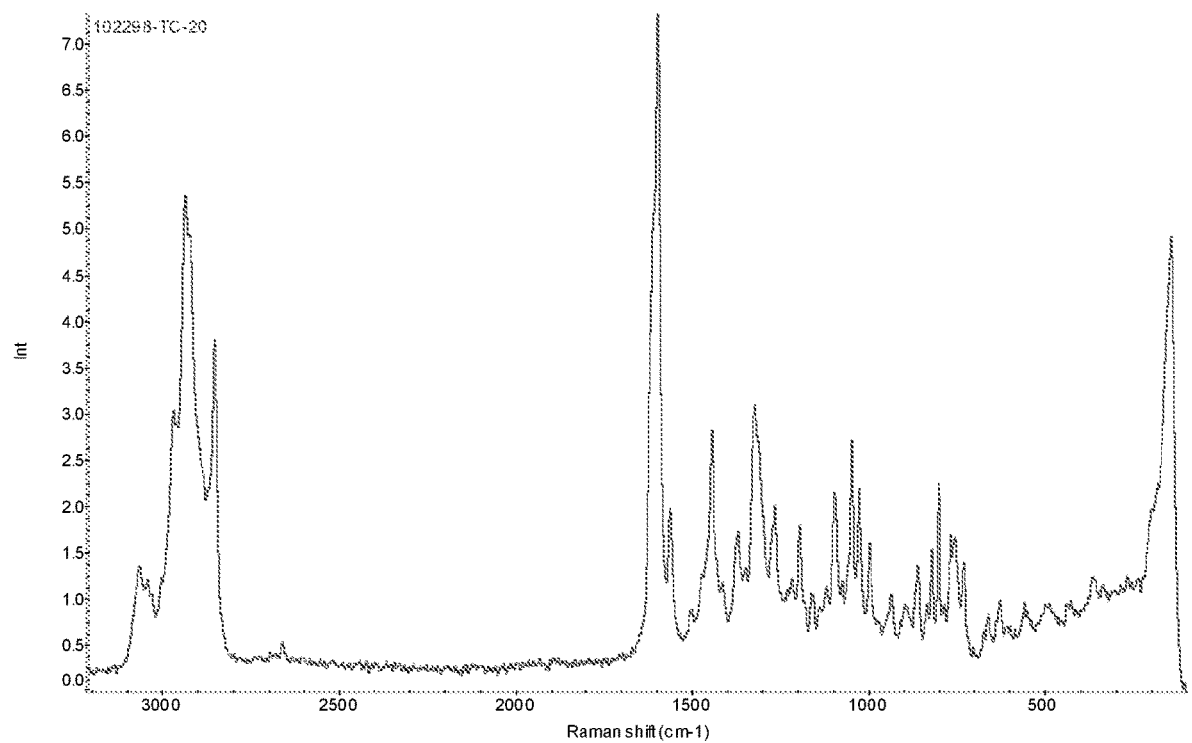
FIG. 6 depicts an FT-Raman spectrum of Form B of Compound 1.

In one embodiment, provided herein is Form B having an FT-Raman Spectrum as depicted in FIG. 6.

Figure 7:
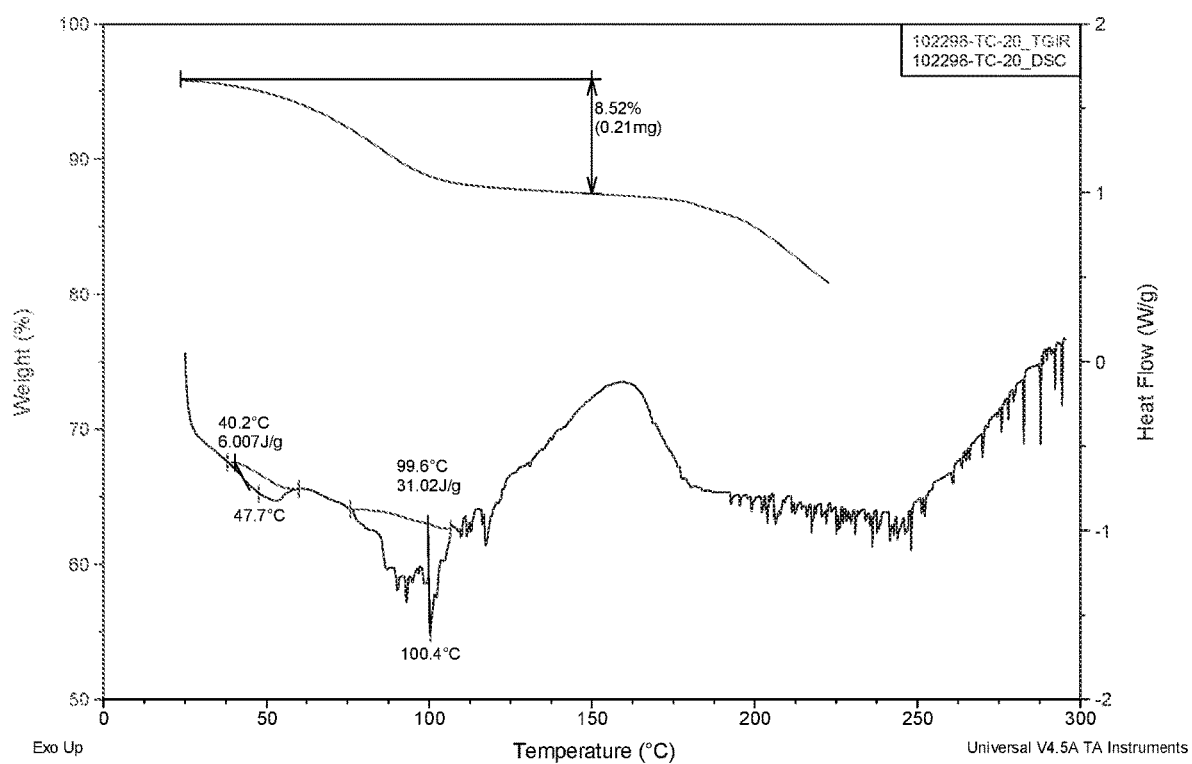
FIG. 7 depicts differential scanning calorimetry/thermal gravimetric analysis of Form B of Compound 1.
Figure 8:
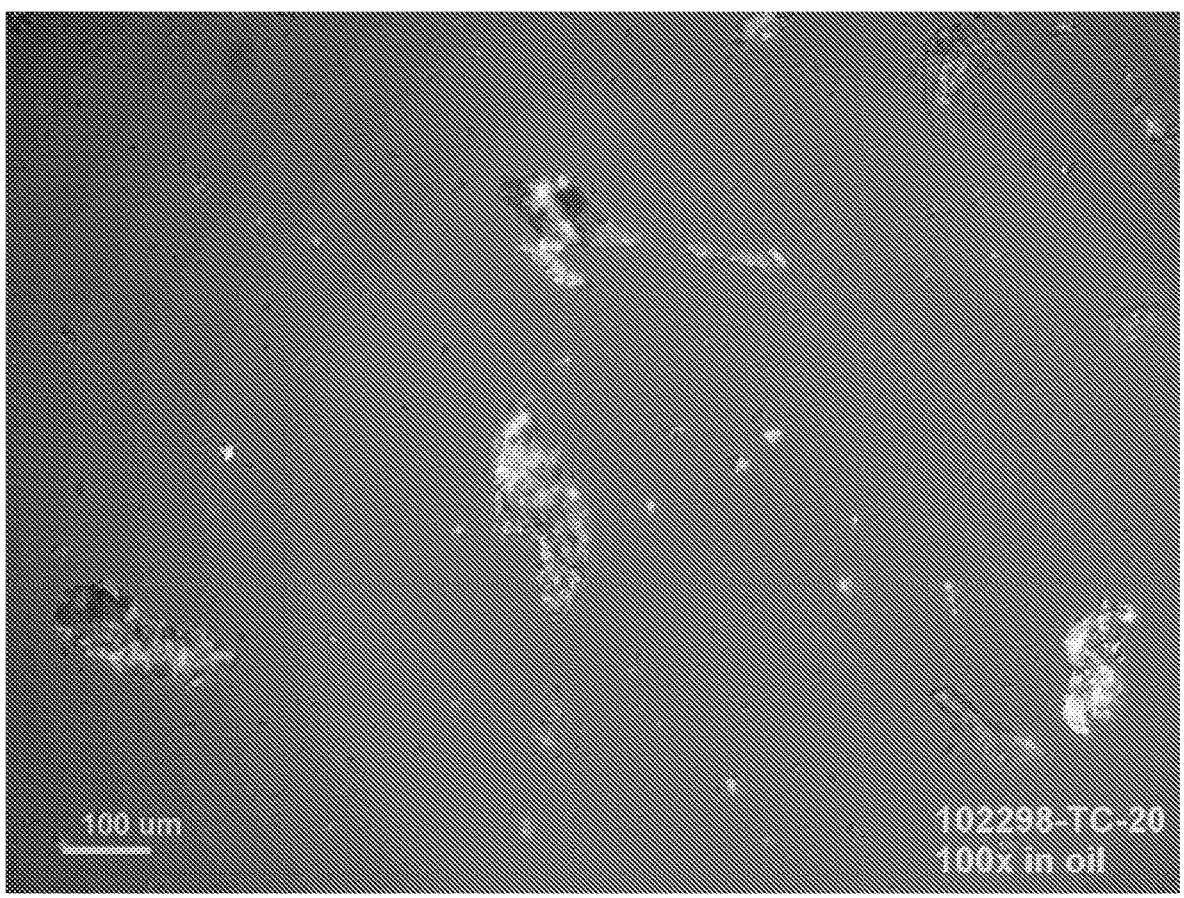
FIG. 8 depicts polarized-light microscopy of Form B of Compound 1.

In one embodiment, provided herein is a solid form, e.g., Form B of Compound 1, having a DSC thermograph substantially as depicted in FIG. 7 comprising a first endothermic event with an onset temperature of about 40.2° C. and a peak maximum temperature of about 47.4° C.

In one embodiment, provided herein is a solid form, e.g., Form B of Compound 1, having a TGA thermogram corresponding substantially to the representative TGA thermogram as depicted in FIG. 7. In certain embodiments, the crystalline form exhibits a TGA thermogram comprising a total mass loss of approximately 8.5% of the total mass of the sample when heated from approximately 25° C. to approximately 150° C. Thus, in certain embodiments, the crystalline form loses about 8.5% its total mass when heated from about ambient temperature to about 150° C.

Figure 5:
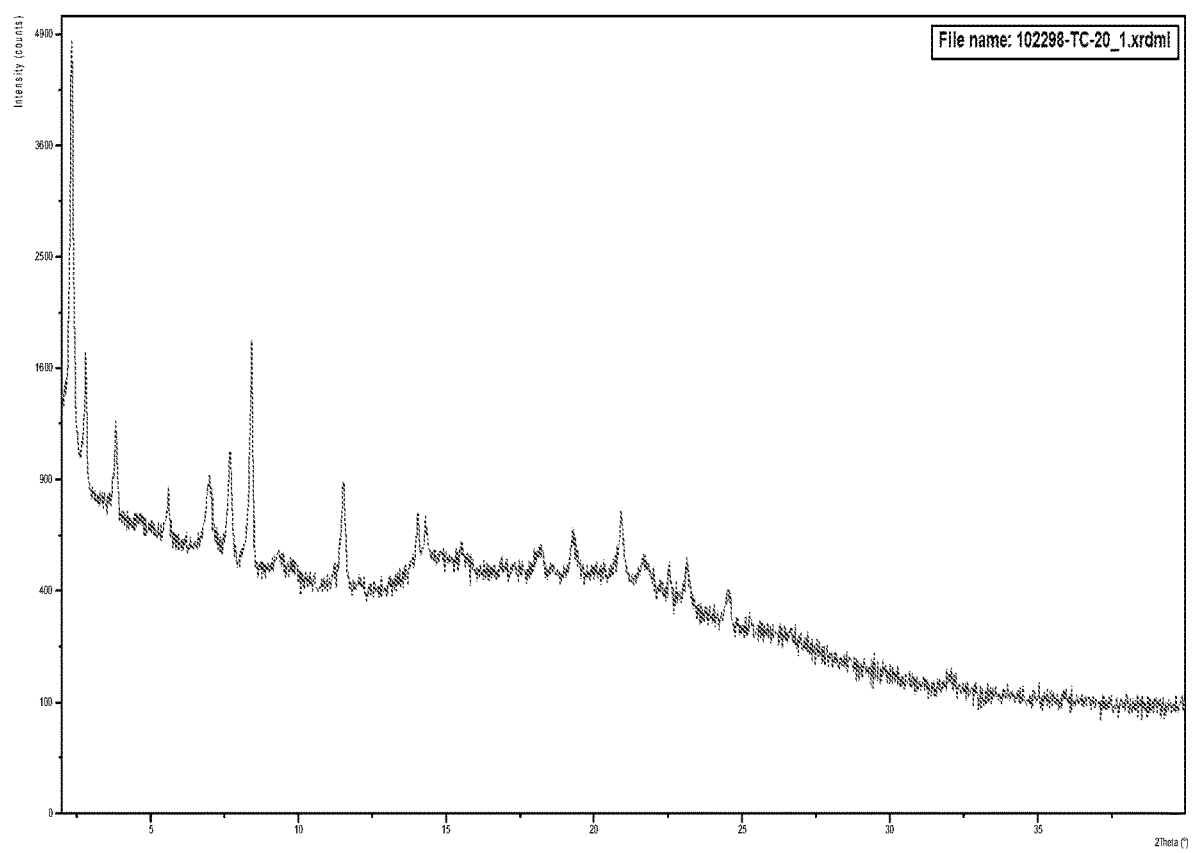
FIG. 5 depicts a PXRD pattern of Form B of Compound 1.

In certain embodiments, a solid form provided herein, e.g., Form B is substantially crystalline, as indicated by, e.g., X-ray powder diffraction measurements. In one embodiment, provided herein is a solid form having an X-ray powder diffraction pattern (XRPD) substantially as shown in FIG. 5 (e.g., Form B). In one embodiment, a solid form provided herein, e.g., Form B, has one or more characteristic X-ray powder diffraction peaks at approximately 2.3, 2.8, 3.8, 5.6, 7.0, 7.7, 8.4, 9.3, 11.5, 14.0, 14.3, 15.5, 18.2, 19.3, 20.9, 21.7, 22.5, 23.2, 24.6, or 32.0° 2θ (±0.2° 2θ) or (±0.1° 2θ) as depicted in FIG. 5. In a specific embodiment, a solid form provided herein has one, two, three, four, five, or six characteristic X-ray powder diffraction peaks at approximately 2.3, 2.8, 7.7, 8.4, 11.5, or 20.9° 2θ (±0.2° 2θ). In certain embodiments, the solid form is Form B.

In still another embodiment, Form B is substantially pure. In certain embodiments, the substantially pure Form B is substantially free of other solid forms, including but not limited to amorphous solid. In certain embodiments, the substantially pure Form B is substantially free of Form A, Form C, Form D, Form E, Form F, Form G, Form H, or Form I. In a particular embodiment, Form B exists in a mixture with Form E. In certain embodiments, the purity of the substantially pure Form B is no less than about 95%, no less than about 96%, no less than about 97%, no less than about 98%, no less than about 98.5%, no less than about 99%, no less than about 99.5%, or no less than about 99.8%. In certain embodiments, the substantially pure Form B is substantially free of Form J, Form K, Form L, Form M, or Form N.

In certain embodiments, Form B is mixed with other solid forms, including but not limited to the amorphous solid. In certain embodiments, Form B is mixed with at least one of Form A, Form C, Form D, Form E, Form F, Form G, Form H, or Form I. In certain embodiments, Form B is mixed with at least one of Form A, Form C, Form D, Form E, Form F, Form G, Form H, Form I, Form J, Form K, Form L, Form M, or Form N.

In one embodiment, Form B comprises a free base of Compound 1. In one embodiment, Form B comprises a free acid of Compound 1. In one embodiment, Form B comprises a zwitterion of Compound 1.

(d) Form C

In certain embodiments, provided herein is Form C.

In one embodiment, Form C is a solid form comprising Compound 1. In one embodiment, Form C is solvated by heptane. In one embodiment, Form C is crystalline. In one embodiment, Form C is moderately crystalline.

In certain embodiments, provided herein are methods for making Form C, comprising: 1) obtaining a slurry of Compound 1 in a solvent or solvent system; 2) stirring the slurry for a period of time (e.g., about 72 h) while cycling the temperature (e.g., between about 5° C. and about 40° C.); and 3) collecting solids from the slurry by filtration and optionally drying the collected solids to yield Form C of Compound 1. In certain embodiments, the solvent is isopropyl ether, cyclohexane, heptane, dimethyl carbonate, or water. In a particular embodiment, the solvent is heptane.

Figure 10:
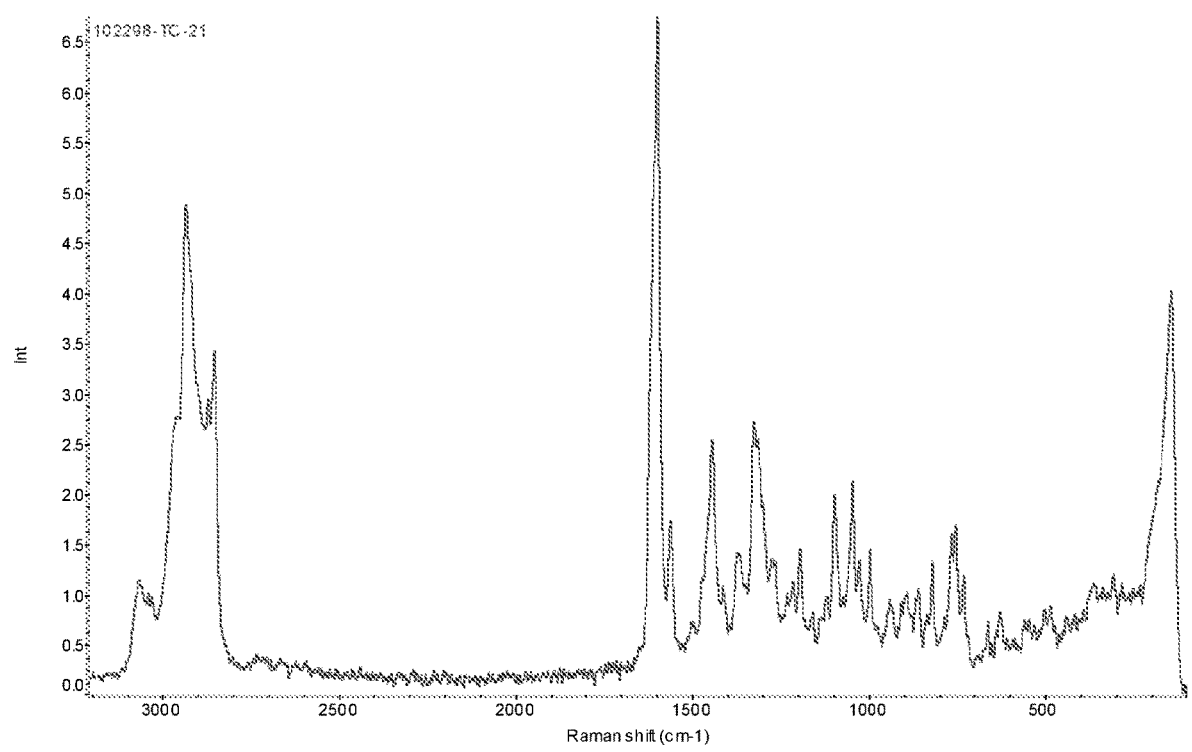
FIG. 10 depicts an FT-Raman spectrum of Form C of Compound 1.

In one embodiment, provided herein is Form C having an FT-Raman Spectrum as depicted in FIG. 10.

Figure 11:
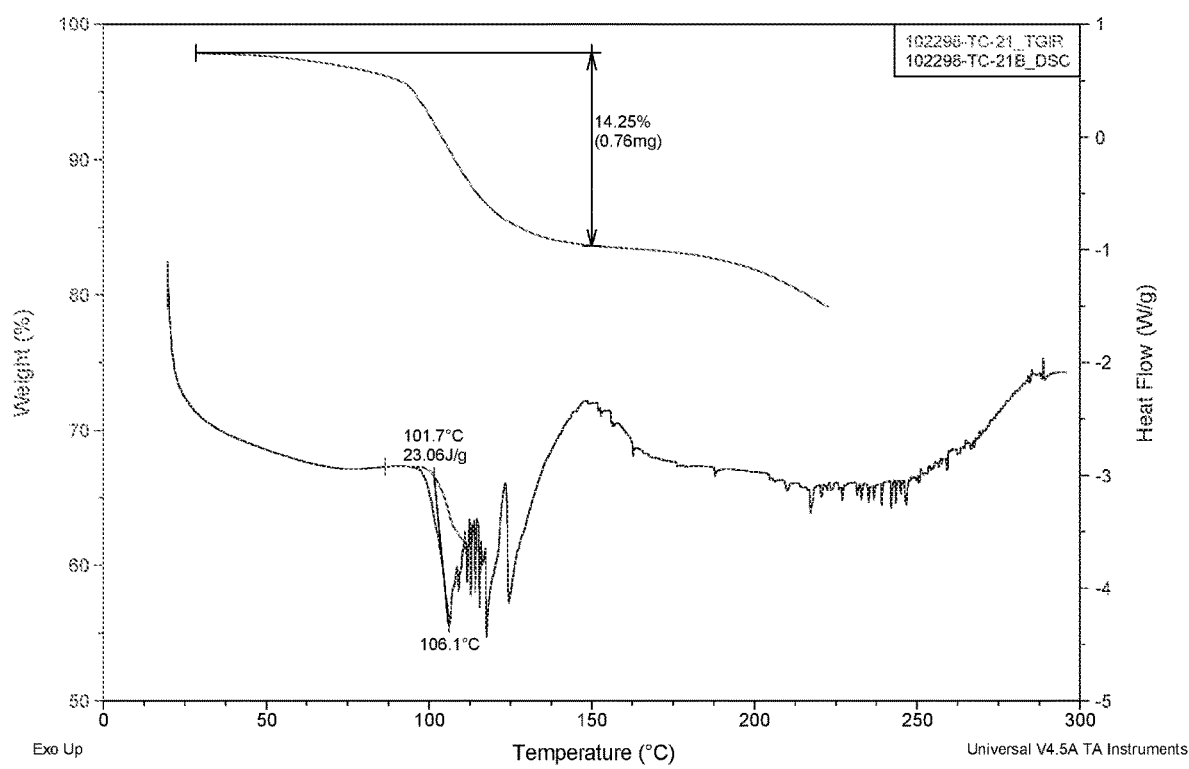
FIG. 11 depicts differential scanning calorimetry/thermal gravimetric analysis of Form C of Compound 1.
Figure 12:
FIG. 12 depicts polarized-light microscopy of Form C of Compound 1.

In one embodiment, provided herein is a solid form, e.g., Form C of Compound 1, having a DSC thermograph substantially as depicted in FIG. 11 comprising an endothermic event with an onset temperature of about 101.7° C.

In one embodiment, provided herein is a solid form, e.g., Form C of Compound 1, having a TGA thermograph corresponding substantially to the representative TGA thermograph as depicted in FIG. 11. In certain embodiments, the crystalline form exhibits a TGA thermogram comprising a total mass loss of approximately 14.3% of the total mass of the sample when heated from approximately 28° C. to approximately 150° C. Thus, in certain embodiments, the crystalline form loses about 14.3% of its total mass when heated from about ambient temperature to about 150° C.

Figure 9:
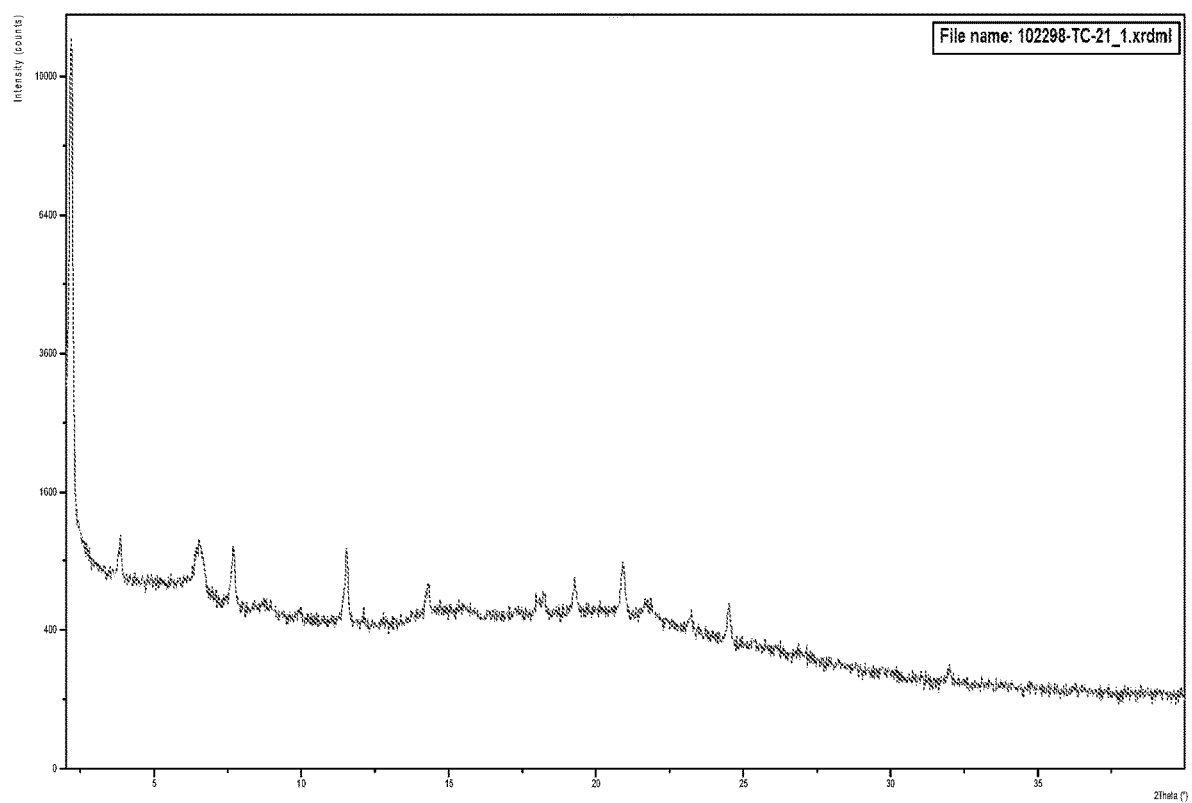
FIG. 9 depicts a PXRD pattern of Form C of Compound 1.

In certain embodiments, a solid form provided herein, e.g., Form C, is substantially crystalline, as indicated by, e.g., X-ray powder diffraction measurements. In one embodiment, provided herein is a solid form having an X-ray powder diffraction pattern (XRPD) substantially as shown in FIG. 9 (e.g., Form C). In one embodiment, a solid form provided herein, e.g., Form C, has one or more characteristic X-ray powder diffraction peaks at approximately 2.2, 3.9, 6.5, 7.7, 8.7, 9.9, 11.5, 14.3, 15.6, 18.3, 19.3, 20.9, 21.8, 23.2, 24.5, and 32.0° 2θ (±0.2° 2θ) or (±0.1° 2θ) as depicted in FIG. 9. In a specific embodiment, a solid form provided herein has one, two, three, four, five, or six characteristic X-ray powder diffraction peaks at approximately 2.2, 3.9, 6.5, 7.7, 11.5, or 20.9° 2θ (±0.2° 2θ). In certain embodiments, the solid form is Form C.

In still another embodiment, Form C is substantially pure. In certain embodiments, the substantially pure Form C is substantially free of other solid forms, including but not limited to amorphous solid. In certain embodiments, the substantially pure Form C is substantially free of Form A, Form B, Form D, Form E, Form F, Form G, Form H, or Form I. In certain embodiments, the purity of the substantially pure Form C is no less than about 95%, no less than about 96%, no less than about 97%, no less than about 98%, no less than about 98.5%, no less than about 99%, no less than about 99.5%, or no less than about 99.8%. In certain embodiments, the substantially pure Form C is substantially free of Form J, Form K, Form L, Form M, or Form N.

In certain embodiments, Form C is mixed with other solid forms, including but not limited to the amorphous solid. In certain embodiments, Form C is mixed with at least one of Form A, Form B, Form D, Form E, Form F, Form G, Form H, or Form I. In certain embodiments, Form C is mixed with at least one of Form A, Form B, Form D, Form E, Form F, Form G, Form H, Form I, Form J, Form K, Form L, Form M, or Form N.

In one embodiment, Form C comprises a free base of Compound 1. In one embodiment, Form C comprises a free acid of Compound 1. In one embodiment, Form C comprises a zwitterion of Compound 1.

(e) Form D

In certain embodiments, provided herein is Form D.

In one embodiment, Form D is a solid form comprising Compound 1. In one embodiment, Form D is non-solvated. In one embodiment, Form D is crystalline. In one embodiment, Form D is moderately crystalline.

In certain embodiments, provided herein are methods for making Form D, comprising: 1) obtaining a slurry of Compound 1 in a solvent or solvent system; 2) stirring the slurry for a period of time (e.g., about 72 h) while cycling the temperature (e.g., between about 5° C. and about 40° C.); and 3) collecting solids from the slurry by filtration and drying the collected solids to yield Form D of Compound 1. In certain embodiments, the solvent is isopropyl ether, cyclohexane, heptanes, dimethyl carbonate, or water. In a particular embodiment, the solvent is dimethyl carbonate. In certain embodiments, the collected solids are dried using a flow of an inert gas, such as nitrogen or argon. In certain embodiments, the collected solids are dried under vacuum at 65° C. In a particular embodiment, the collected solids are dried using a flow of an inert gas, such as nitrogen or argon, under vacuum at 65° C.

Figure 14:
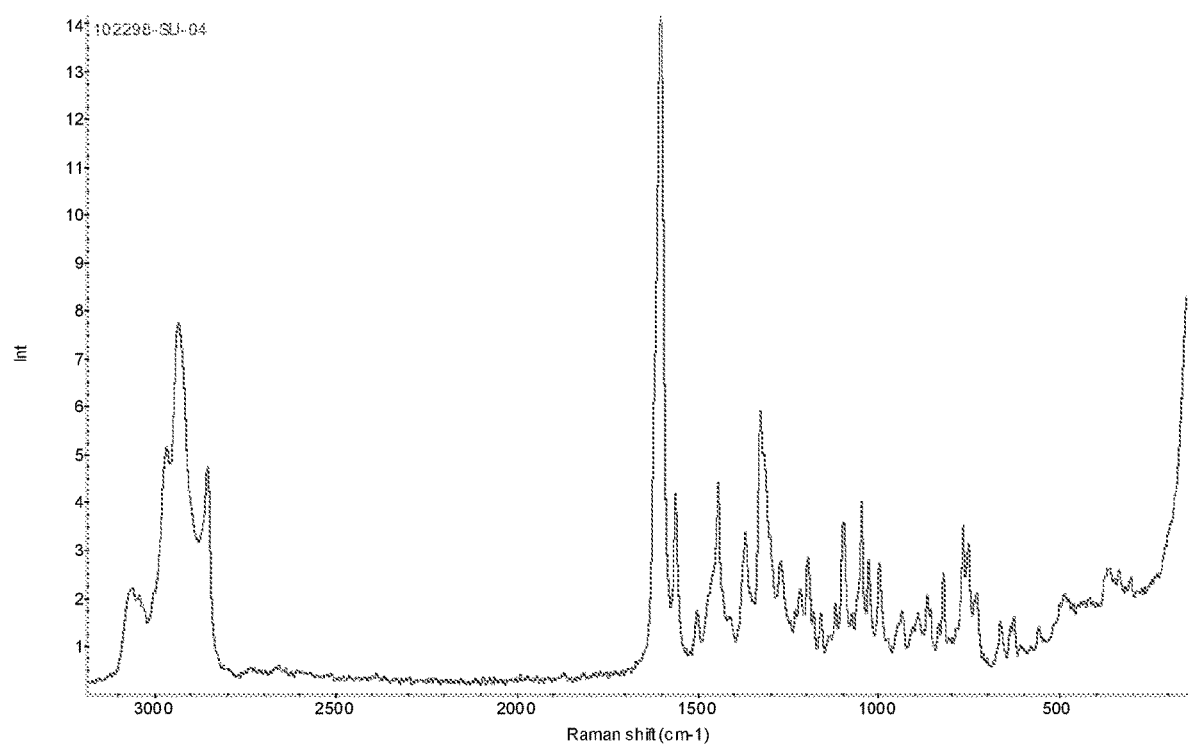
FIG. 14 depicts an FT-Raman spectrum of Form D of Compound 1.

In one embodiment, provided herein is Form D having an FT-Raman Spectrum as depicted in FIG. 14.

Figure 15:
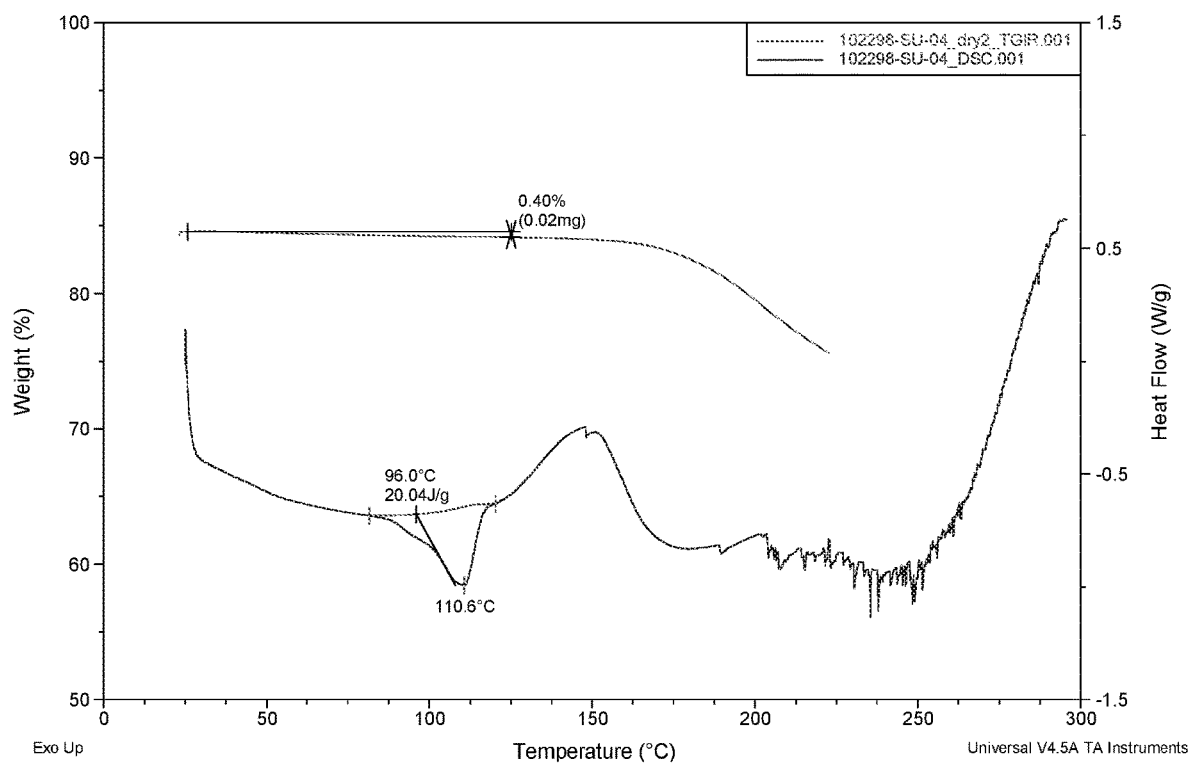
FIG. 15 depicts differential scanning calorimetry/thermal gravimetric analysis of Form D of Compound 1.
Figure 16:
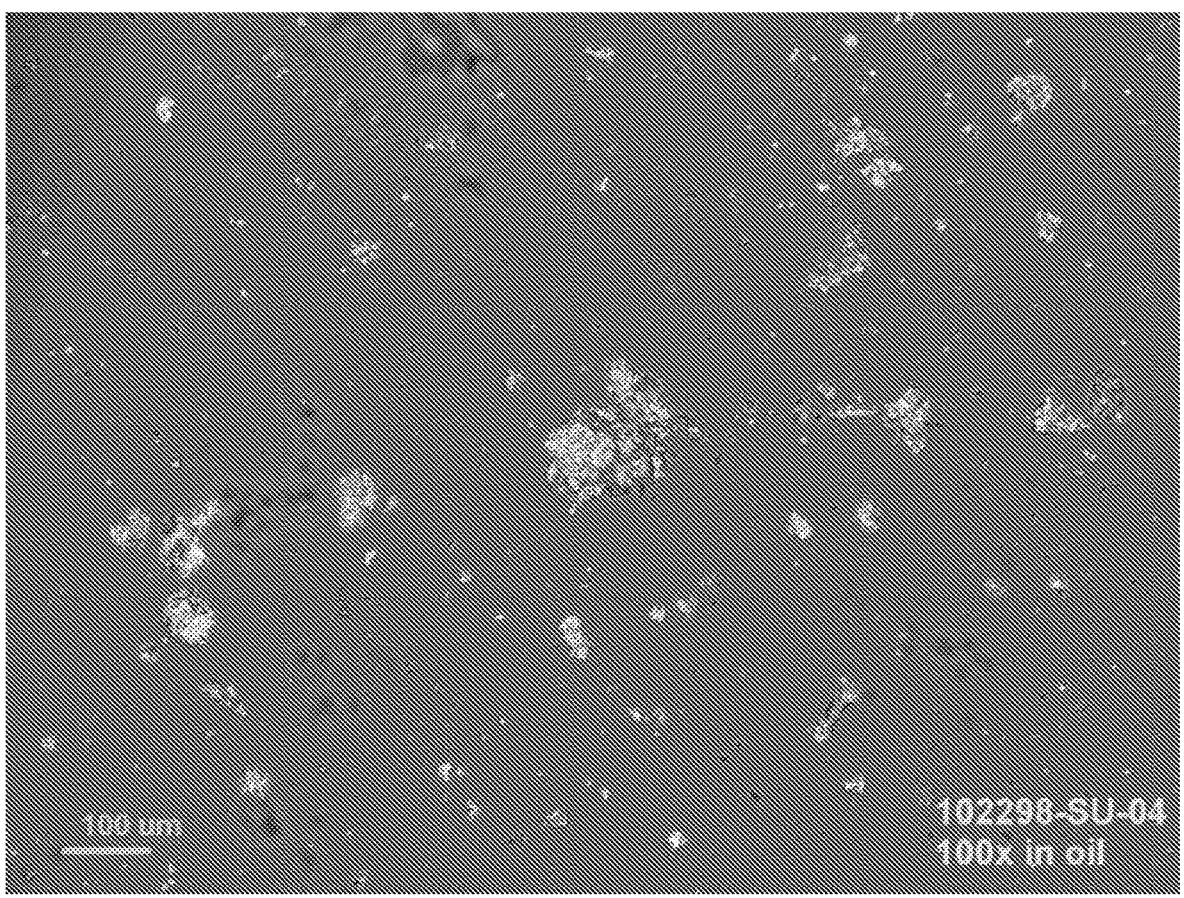
FIG. 16 depicts polarized-light microscopy of Form D of Compound 1.

In one embodiment, provided herein is a solid form, e.g., Form D of Compound 1, having a DSC thermogram substantially as depicted in FIG. 15 comprising an endothermic event with an onset temperature of about 96° C. and a peak maximum temperature of about 111° C.

In one embodiment, provided herein is a solid form, e.g., Form D of Compound 1, having a TGA thermogram corresponding substantially to the representative TGA thermogram as depicted in FIG. 15. In certain embodiments, the crystalline form exhibits a TGA thermogram comprising a total mass loss of approximately 0.4% of the total mass of the sample when heated from approximately 25° C. and 125° C.

Figure 13:
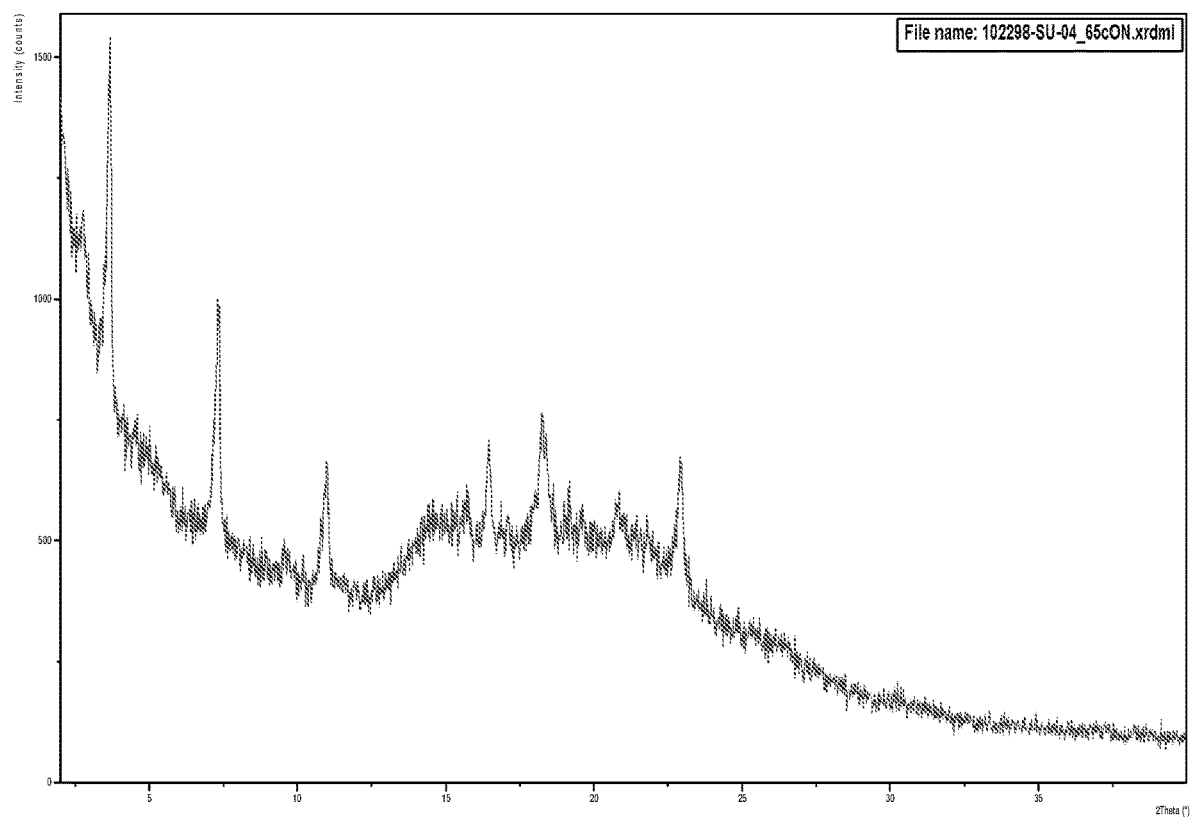
FIG. 13 depicts a PXRD pattern of Form D of Compound 1.

In certain embodiments, a solid form provided herein, e.g., Form D, is substantially crystalline, as indicated by, e.g., X-ray powder diffraction measurements. In one embodiment, provided herein is a solid form having an X-ray powder diffraction pattern (XRPD) substantially as shown in FIG. 13 (e.g., Form D). In one embodiment, a solid form provided herein, e.g., Form D, has one or more characteristic X-ray powder diffraction peaks at approximately 2.8, 3.7, 7.3, 11.0, 14.4, 16.4, 18.3, 20.8, or 22.9° 2θ (±0.2° 2θ) or (±0.1° 2θ) as depicted in FIG. 13. In a specific embodiment, a solid form provided herein has one, two, three, four, or five characteristic X-ray powder diffraction peaks at approximately 3.7, 7.3, 11.0, 18.3, or 22.9° 2θ (±0.2° 2θ). In certain embodiments, the solid form is Form D.

In still another embodiment, Form D is substantially pure. In certain embodiments, the substantially pure Form D is substantially free of other solid forms, including but not limited to amorphous solid. In certain embodiments, the substantially pure Form D is substantially free of Form A, Form B, Form C, Form E, Form F, Form G, Form H, or Form I. In certain embodiments, the purity of the substantially pure Form D is no less than about 95%, no less than about 96%, no less than about 97%, no less than about 98%, no less than about 98.5%, no less than about 99%, no less than about 99.5%, or no less than about 99.8%. In certain embodiments, the substantially pure Form D is substantially free of Form J, Form K, Form L, Form M, or Form N.

In certain embodiments, Form D is mixed with other solid forms, including but not limited to the amorphous solid. In certain embodiments, Form D is mixed with at least one of Form A, Form B, Form C, Form E, Form F, Form G, Form H, or Form I. In certain embodiments, Form D is mixed with at least one of Form A, Form B, Form C, Form E, Form F, Form G, Form H, Form I, Form J, Form K, Form L, Form M, or Form N.

In one embodiment, Form D comprises a free base of Compound 1. In one embodiment, Form D comprises a free acid of Compound 1. In one embodiment, Form D comprises a zwitterion of Compound 1.

(f) Form E

In certain embodiments, provided herein is Form E.

In one embodiment, Form E is a solid form comprising Compound 1. In one embodiment, Form E is non-solvated. In one embodiment, Form E is crystalline.

In certain embodiments, provided herein are methods for making Form E, comprising: 1) obtaining a slurry of Compound 1 in a solvent or solvent system; 2) seeding the slurry with a small amount (e.g., 1 mg) of a solid form described herein (e.g., Form D, or Form I) and stirring the slurry for a period of time (e.g., about 48 h) while cycling the temperature (e.g., between about 5° C. and about 30° C.); and 3) collecting solids from the slurry by filtration to yield Form E of Compound 1. In one embodiment, the solvent system is selected from the group consisting of nitromethane, acetonitrile, octane/ethyl acetate (9:1), acetonitrile/toluene (9:1), isopropyl ether/acetonitrile (1:2), octane/acetone (9:1), acetonitrile/methyl t-butyl ether (9:1), or acetonitrile/methyl isobutyl ketone (9:1).

In certain embodiments, provided herein are methods for making Form E, comprising: 1) obtaining a slurry of Compound 1 in a solvent or solvent system; 2) seeding the slurry with a small amount (e.g., 1 mg) of a solid form described herein (e.g., Form E) and stirring the slurry for a period of time (e.g., overnight, or about 48 h) while cycling the temperature (e.g., between about 5° C. and about 40° C.); and 3) collecting solids from the slurry by filtration to yield Form E of Compound 1. In one embodiment, the method further comprises the step of drying the collected solids under vacuum at 65° C. to yield Form E of Compound 1. In a particular embodiment, the collected solids are dried using a flow of an inert gas, such as nitrogen or argon, under vacuum at 65° C. In one embodiment, the solvent or solvent system is selected from the group consisting of toluene/heptane (1:3), methyl t-butyl ether/hexane (1:9), methyl t-butyl ether/acetonitrile (1:9), and isopropyl ether. In a preferred embodiment, the solvent is isopropyl ether.

In certain other embodiments, provided herein are methods for making Form E, comprising: 1) obtaining a slurry of Compound 1 in a solvent or solvent system; 2) heating the slurry to a certain temperature (e.g., 40° C.); 3) filtering the hot solution to remove impurities; 4) storing the hot filtrate at 4° C. for a period of time (e.g., 7 days); and 5) collecting solids from the cooled solution by filtration to yield Form E of Compound 1. In one embodiment, the solvent system is methyl isobutyl ketone/heptane.

Figure 18:
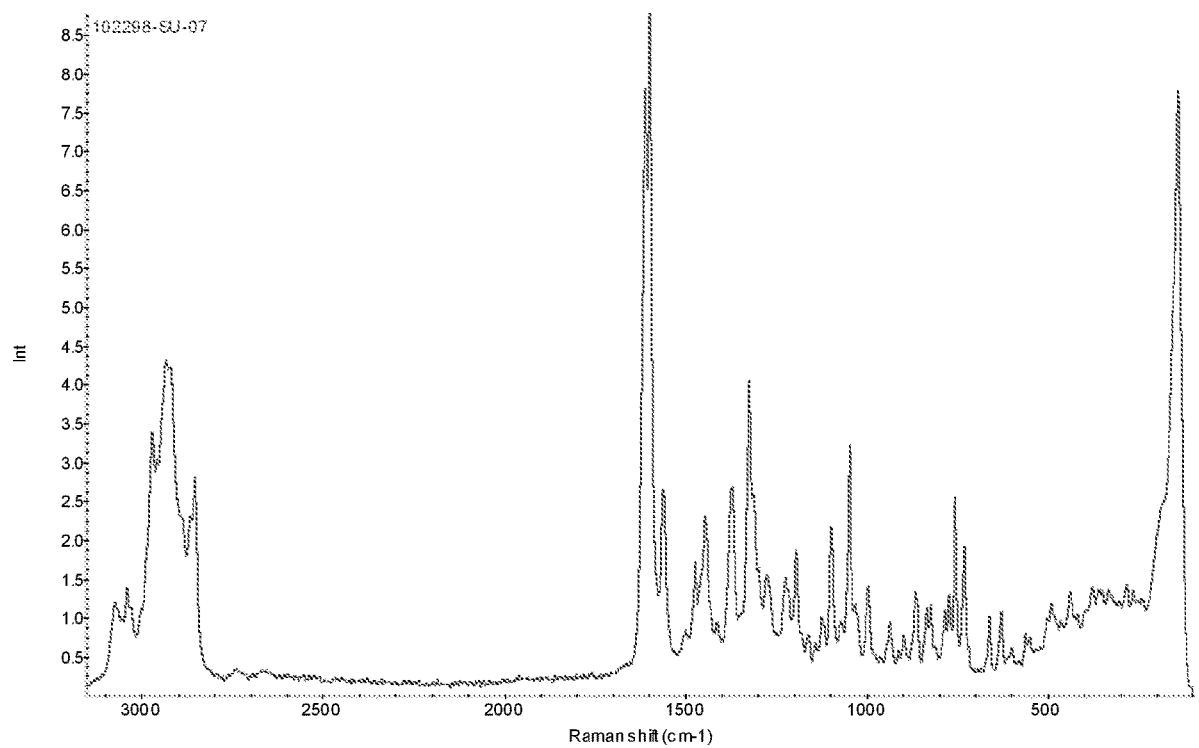
FIG. 18 depicts an FT-Raman spectrum of Form E of Compound 1.

In one embodiment, provided herein is Form E having an FT-Raman Spectrum as depicted in FIG. 18.

Figure 19:
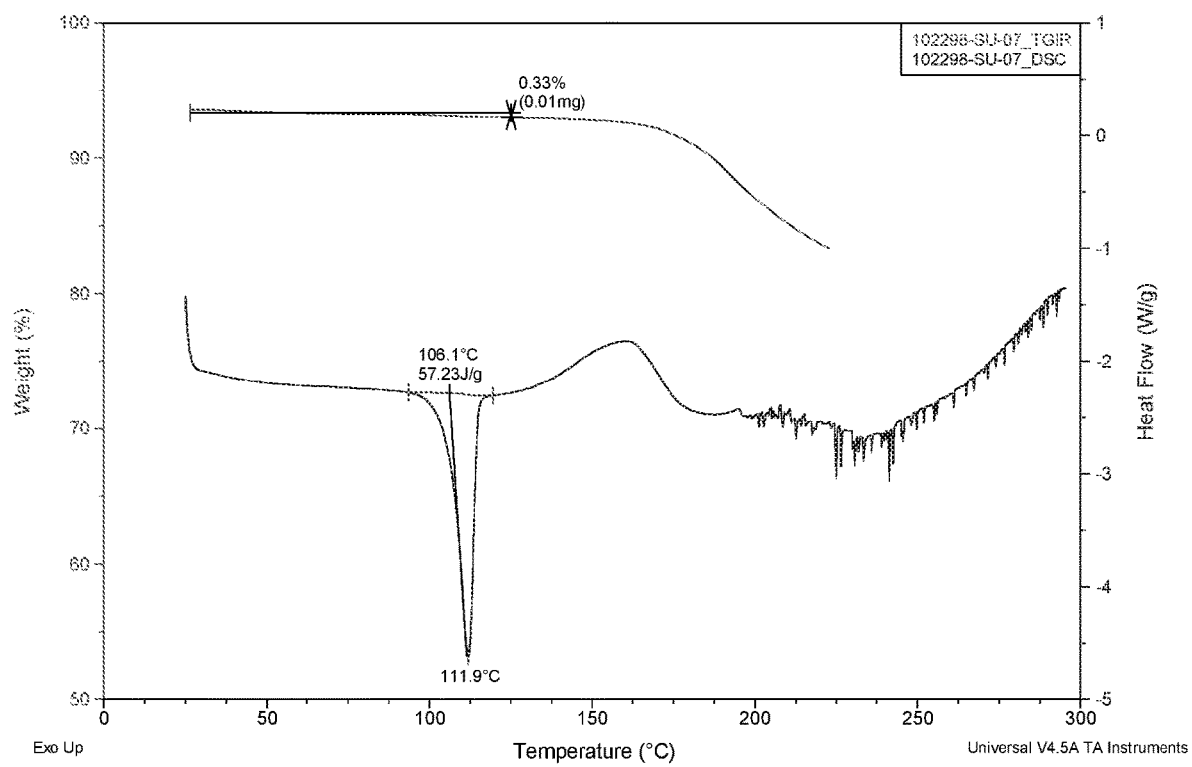
FIG. 19 depicts differential scanning calorimetry/thermal gravimetric analysis of Form E of Compound 1.
Figure 20:
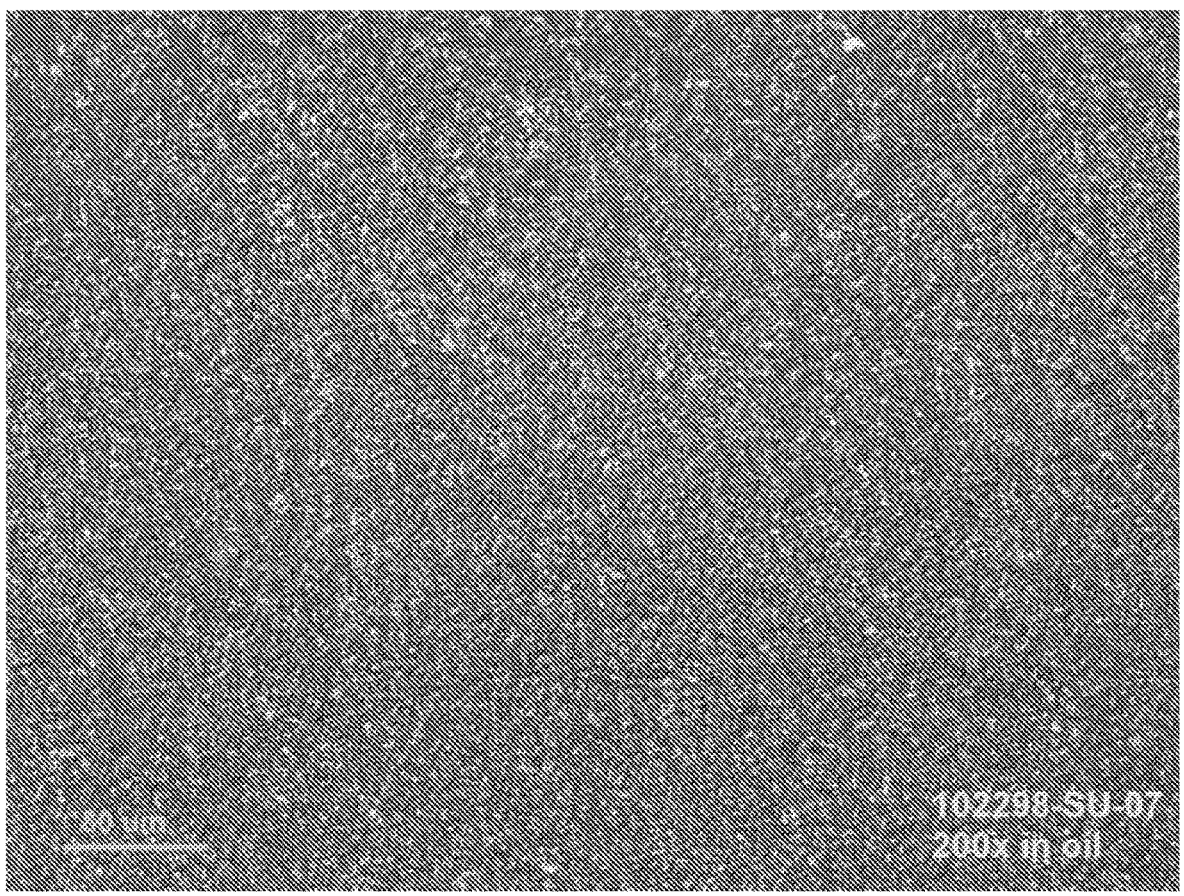
FIG. 20 depicts polarized-light microscopy of Form E of Compound 1.

In one embodiment, provided herein is a solid form, e.g., Form E of Compound 1, having a DSC thermograph substantially as depicted in FIG. 19 comprising an endothermic event with an onset temperature of about 106° C.

In one embodiment, provided herein is a solid form, e.g., Form E of Compound 1, having a TGA thermogram corresponding substantially to the representative TGA thermogram as depicted in FIG. 19. In certain embodiments, the crystalline form exhibits a TGA thermogram comprising a total mass loss of approximately 0.3% of the total mass of the sample when heated from approximately 25° C. to about 125° C.

Figure 17:
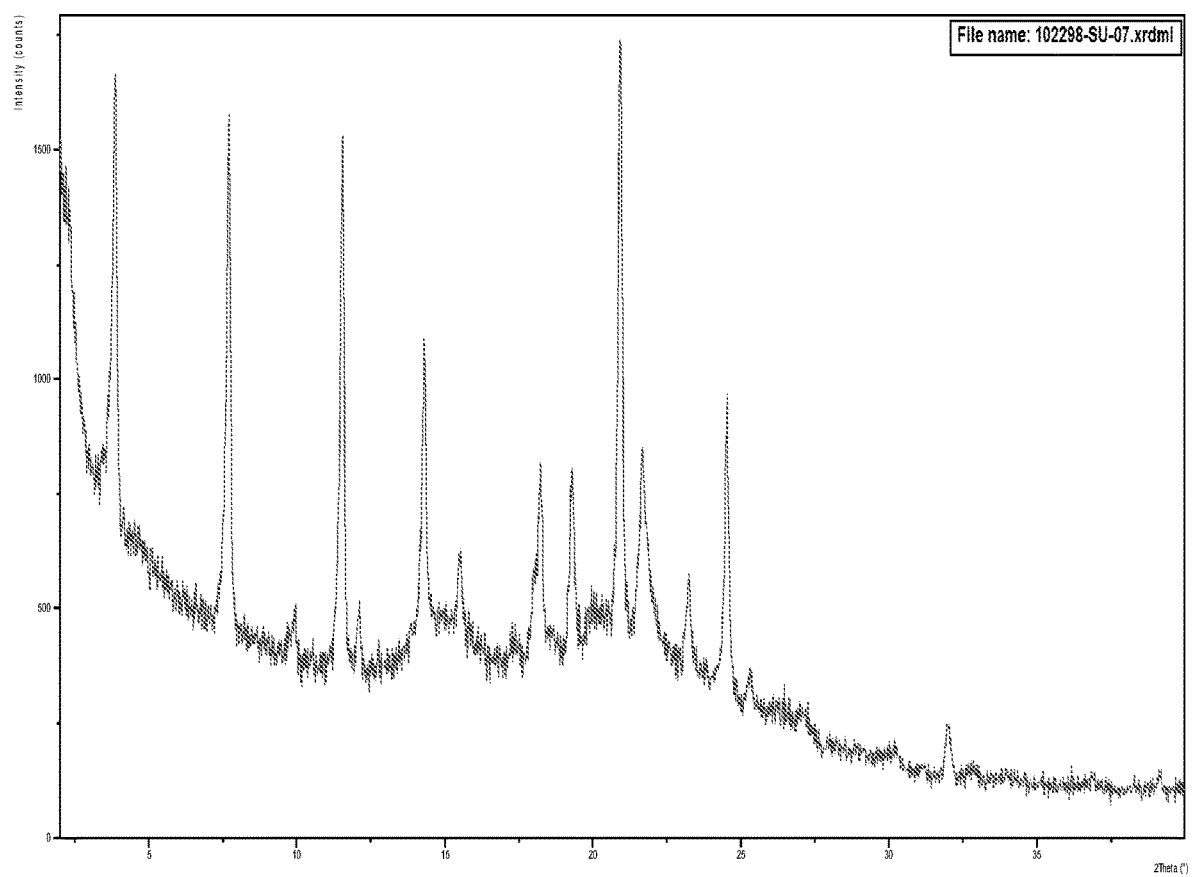
FIG. 17 depicts a PXRD pattern of Form E of Compound 1.

In certain embodiments, a solid form provided herein, e.g., Form E, is substantially crystalline, as indicated by, e.g., X-ray powder diffraction measurements. In one embodiment, provided herein is a solid form having an X-ray powder diffraction pattern (XRPD) substantially as shown in FIG. 17 (e.g., Form E). In one embodiment, a solid form provided herein, e.g., Form E, has one or more characteristic X-ray powder diffraction peaks at approximately 3.9, 7.7, 9.9, 11.6, 12.1, 14.3, 15.5, 17.3, 18.2, 19.3, 20.9, 21.7, 23.3, 24.5, 25.3, 32.0° 2θ (±0.2° 2θ) or (±0.1° 2θ) as depicted in FIG. 17. In a specific embodiment, a solid form provided herein has one, two, three, four, five or six characteristic X-ray powder diffraction peaks at approximately 3.9, 7.7, 11.6, 14.3, 20.9, 24.5° 2θ (±0.2° 2θ). In certain embodiments, the solid form is Form E.

In still another embodiment, Form E is substantially pure. In certain embodiments, the substantially pure Form E is substantially free of other solid forms, including but not limited to amorphous solid. In certain embodiments, the substantially pure Form E is substantially free of Form A, Form B, Form C, Form D, Form F, Form G, Form H, or Form I. In certain embodiments, the purity of the substantially pure Form D is no less than about 95%, no less than about 96%, no less than about 97%, no less than about 98%, no less than about 98.5%, no less than about 99%, no less than about 99.5%, or no less than about 99.8%. In certain embodiments, the substantially pure Form E is substantially free of Form J, Form K, Form L, Form M, or Form N.

In certain embodiments, Form E is mixed with other solid forms, including but not limited to the amorphous solid. In certain embodiments, Form E is mixed with at least one of Form A, Form B, Form C, Form D, Form F, Form G, Form H, or Form I. In certain embodiments, Form E is mixed with at least one of Form A, Form B, Form C, Form D, Form F, Form G, Form H, Form I, Form J, Form K, Form L, Form M, or Form N.

In one embodiment, Form E comprises a free base of Compound 1. In one embodiment, Form E comprises a free acid of Compound 1. In one embodiment, Form E comprises a zwitterion of Compound 1.

(g) Form F

In certain embodiments, provided herein is Form F.

In one embodiment, Form F is a solid form comprising Compound 1. In one embodiment, Form F is solvated by dimethyl carbonate. In one embodiment, Form F is crystalline. In one embodiment, Form F is moderately crystalline.

In certain embodiments, provided herein are methods for making Form F, comprising: 1) obtaining a slurry of Compound 1 in a solvent, and stirring at 20° C. for 1 h; 2) seeding the slurry with a small amount (e.g., 1 mg) of a solid form described herein (e.g., Form D), 3) stirring the slurry for a period of time (e.g., about 12 h) at 20° C.; and 3) collecting solids from the slurry to yield Form F of Compound 1. In one embodiment, the solids are collected by centrifugation followed by decanting, washing, and drying in a centrifuge evaporator overnight. In one embodiment, the solvent is dimethyl carbonate.

Figure 22:
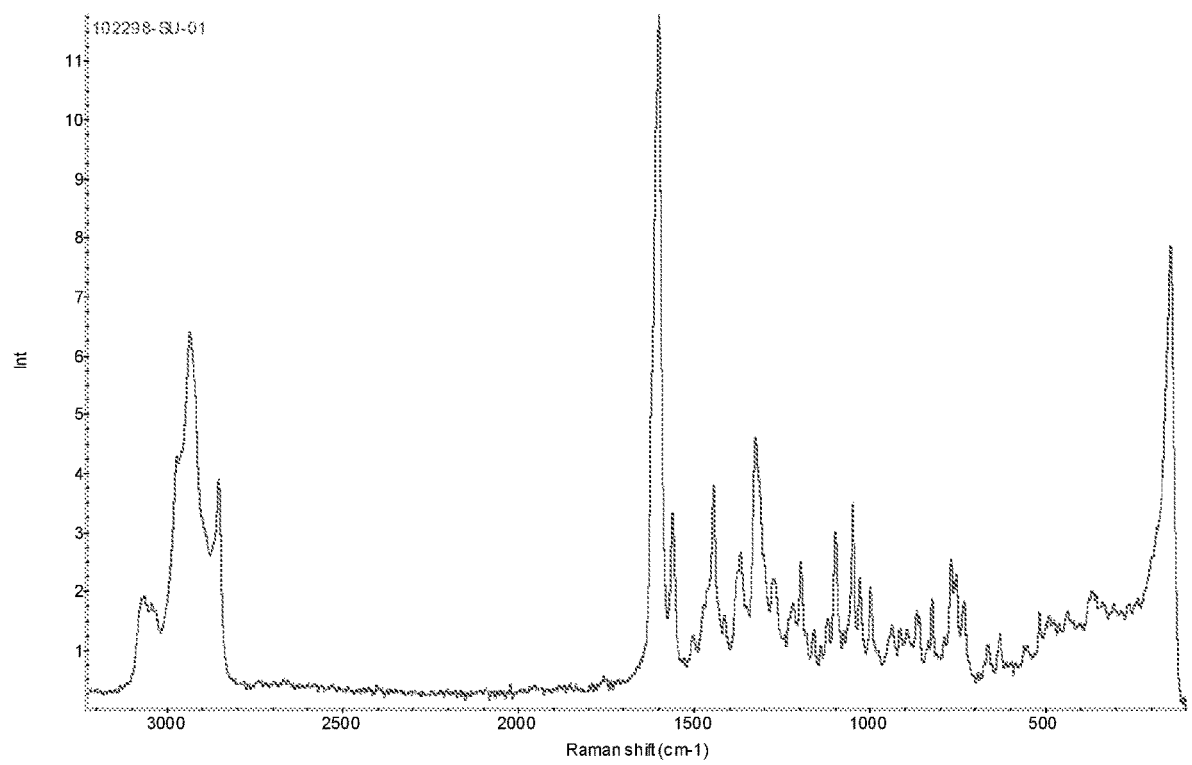
FIG. 22 depicts an FT-Raman spectrum of Form F of Compound 1.

In one embodiment, provided herein is Form F having an FT-Raman Spectrum as depicted in FIG. 22.

Figure 23:
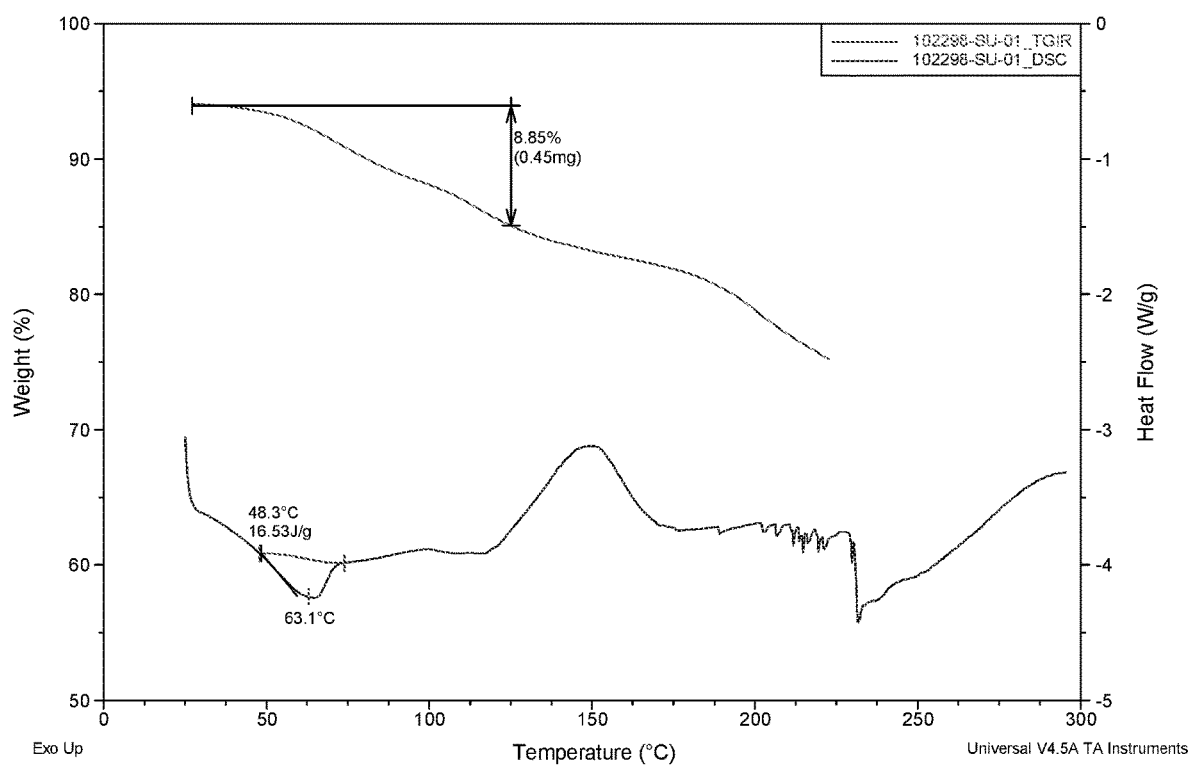
FIG. 23 depicts differential scanning calorimetry/thermal gravimetric analysis of Form F of Compound 1.
Figure 24:
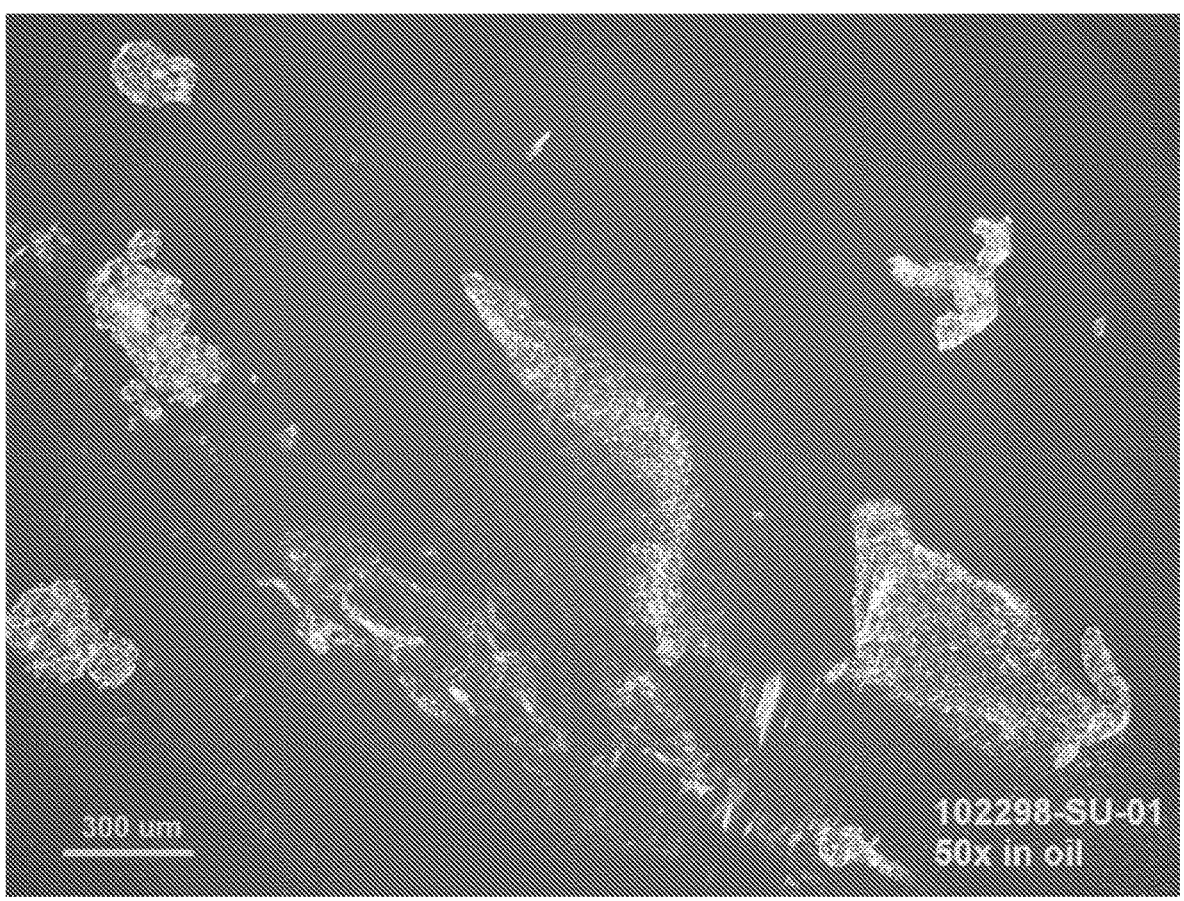
FIG. 24 depicts polarized-light microscopy of Form F of Compound 1.

In one embodiment, provided herein is a solid form, e.g., Form F of Compound 1, having a DSC thermograph substantially as depicted in FIG. 23 comprising an endothermic event with an onset temperature at about 48° C. and a peak maximum temperature at about 63° C.

In one embodiment, provided herein is a solid form, e.g., Form F of Compound 1, having a TGA thermograph corresponding substantially to the representative TGA thermograph as depicted in FIG. 23. In certain embodiments, the crystalline form exhibits a TGA thermograph comprising a total mass loss of approximately 8.9% of the total mass of the sample when heated between approximately 25° C. and approximately 125° C. Thus, in certain embodiments, the crystalline loses about 8.9% its total mass when heated from ambient temperature to about 125° C.

Figure 21:
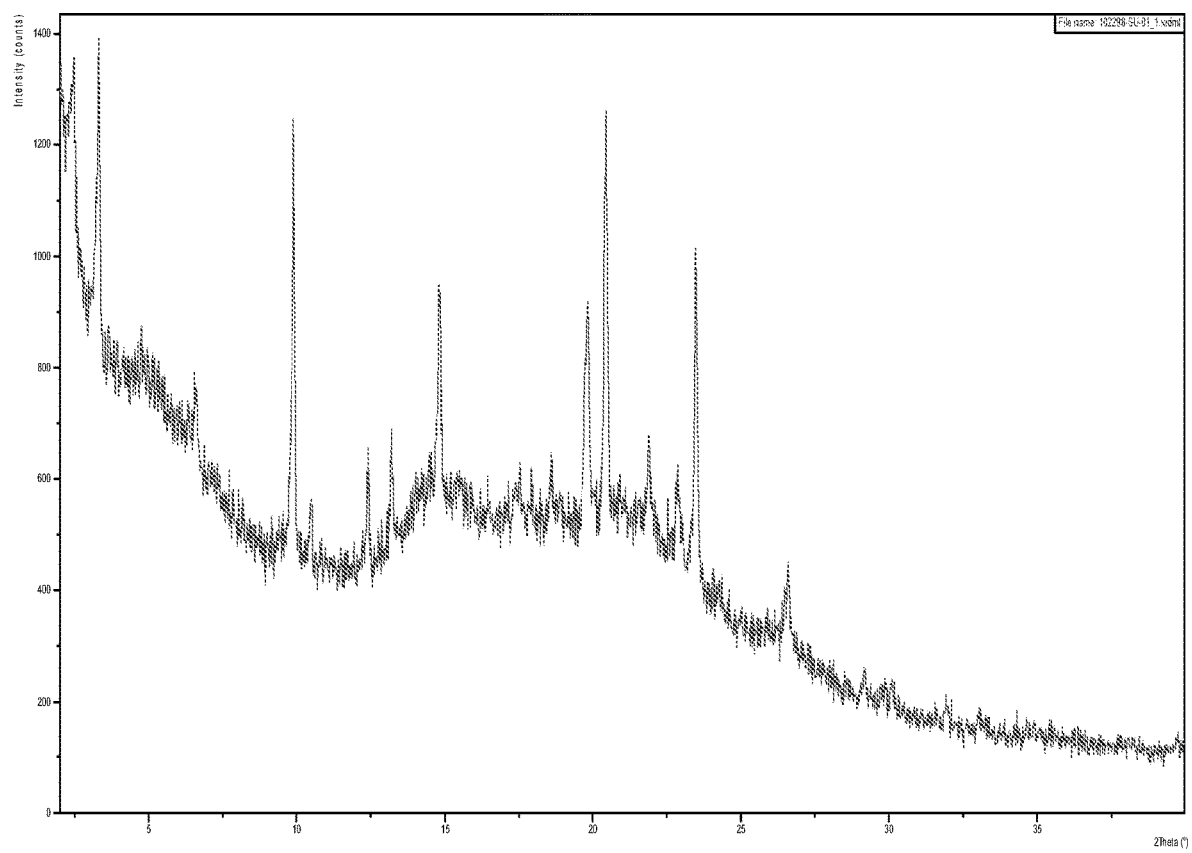
FIG. 21 depicts a PXRD pattern of Form F of Compound 1.

In certain embodiments, a solid form provided herein, e.g., Form F, is substantially crystalline, as indicated by, e.g., X-ray powder diffraction measurements. In one embodiment, provided herein is a solid form having an X-ray powder diffraction pattern (XRPD) substantially as shown in FIG. 21 (e.g., Form F). In one embodiment, a solid form provided herein, e.g., Form F, has one or more characteristic X-ray powder diffraction peaks at approximately 2.5, 3.3, 6.6, 9.9, 10.5, 12.4, 13.2, 14.8, 19.9, 20.4, 21.9, 22.9, 23.5, or 26.6° 2θ (±0.2° 2θ) or (±0.1° 2θ) as depicted in FIG. 21. In a specific embodiment, a solid form provided herein has one, two, three, four, five or six characteristic X-ray powder diffraction peaks at approximately 3.3, 9.9, 14.8, 19.9, 20.4, or 23.5° 2θ (±0.2° 2θ). In certain embodiments, the solid form is Form F.

In still another embodiment, Form F is substantially pure. In certain embodiments, the substantially pure Form F is substantially free of other solid forms, including but not limited to amorphous solid. In certain embodiments, the substantially pure Form F is substantially free of Form A, Form B, Form C, Form D, Form E, Form G, Form H, or Form I. In certain embodiments, the purity of the substantially pure Form F is no less than about 95%, no less than about 96%, no less than about 97%, no less than about 98%, no less than about 98.5%, no less than about 99%, no less than about 99.5%, or no less than about 99.8%. In certain embodiments, the substantially pure Form F is substantially free of Form J, Form K, Form L, Form M, or Form N.

In certain embodiments, Form F is mixed with other solid forms, including but not limited to the amorphous solid. In certain embodiments, Form F is mixed with at least one of Form A, Form B, Form C, Form D, Form E, Form G, Form H, or Form I. In certain embodiments, Form F is mixed with at least one of Form A, Form B, Form C, Form D, Form E, Form G, Form H, Form I, Form J, Form K, Form L, Form M, or Form N.

In one embodiment, Form F comprises a free base of Compound 1. In one embodiment, Form F comprises a free acid of Compound 1. In one embodiment, Form F comprises a zwitterion of Compound 1.

(h) Form G

In certain embodiments, provided herein is Form G.

In one embodiment, Form G is a solid form comprising Compound 1.

In certain embodiments, provided herein are methods for making Form G, comprising: 1) obtaining a slurry of Compound 1 in a solvent or solvent system; 2) stirring the slurry for a period of time (e.g., about 72 h) while cycling the temperature (e.g., between about 5° C. and about 40° C.); and 3) collecting solids from the slurry by filtration to yield a mixture of Form G and Form D. In certain embodiments, the solvent is isopropyl ether, cyclohexane, heptanes, dimethyl carbonate, or water. In a particular embodiment, the solvent is dimethyl carbonate. In certain embodiments, the collected solids are dried using a flow of an inert gas, such as nitrogen or argon.

In certain embodiments, Form G is mixed with other solid forms, including but not limited to the amorphous solid. In certain embodiments, Form G is mixed with at least one of Form A, Form B, Form C, Form D, Form E, Form F, Form H, or Form I. In certain embodiments, the substantially pure Form G is substantially free of Form J, Form K, Form L, Form M, or Form N.

In one embodiment, Form G comprises a free base of Compound 1. In one embodiment, Form G comprises a free acid of Compound 1. In one embodiment, Form G comprises a zwitterion of Compound 1. In certain embodiments, Form G is mixed with at least one of Form A, Form B, Form C, Form D, Form E, Form F, Form H, Form I, Form J, Form K, Form L, Form M, or Form N.

(i) Form H

In certain embodiments, provided herein is Form H.

In one embodiment, Form H is a solid form comprising Compound 1. In one embodiment, Form H is solvated by water. In one embodiment, Form H is a hydrate. In one embodiment, Form H is crystalline.

In certain embodiments, provided herein are methods for making Form H, comprising: 1) obtaining a slurry of Form E in a solvent or solvent system; 2) seeding the slurry with a small amount of a solid form described herein (e.g., Form D or Form I), 3) stirring the slurry for a period of time (e.g., about 48 h) while cycling between two temperatures (e.g., 5° C. and 30° C.); and 3) collecting solids from the slurry and optionally drying to yield Form H of Compound 1. In certain embodiments, the solvent is water. In certain embodiments, the solvent system is a 10% mixture of water in acetonitrile. In certain embodiments, the solvent system is a mixture of 10% 1-propanol in water.

Figure 26:
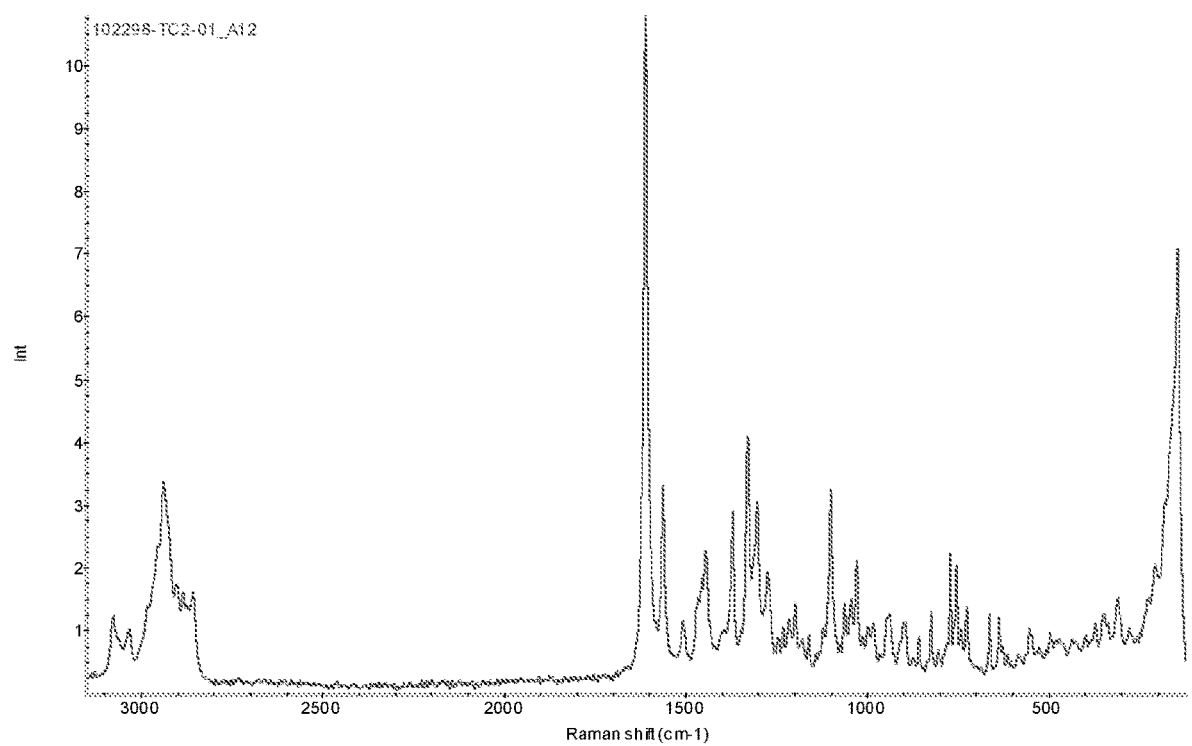
FIG. 26 depicts an FT-Raman spectrum of Form H of Compound 1.

In one embodiment, provided herein is Form H having an FT-Raman Spectrum as depicted in FIG. 26.

Figure 27:
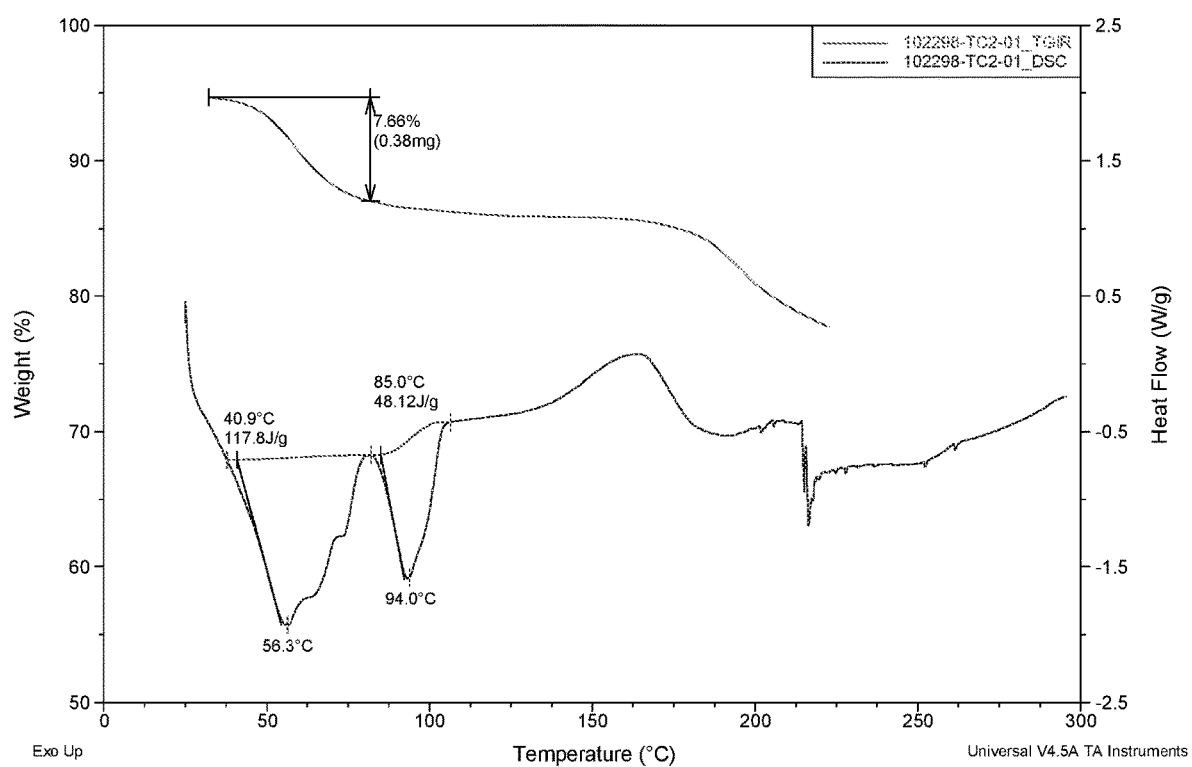
FIG. 27 depicts differential scanning calorimetry/thermal gravimetric analysis of Form H of Compound 1.
Figure 28:
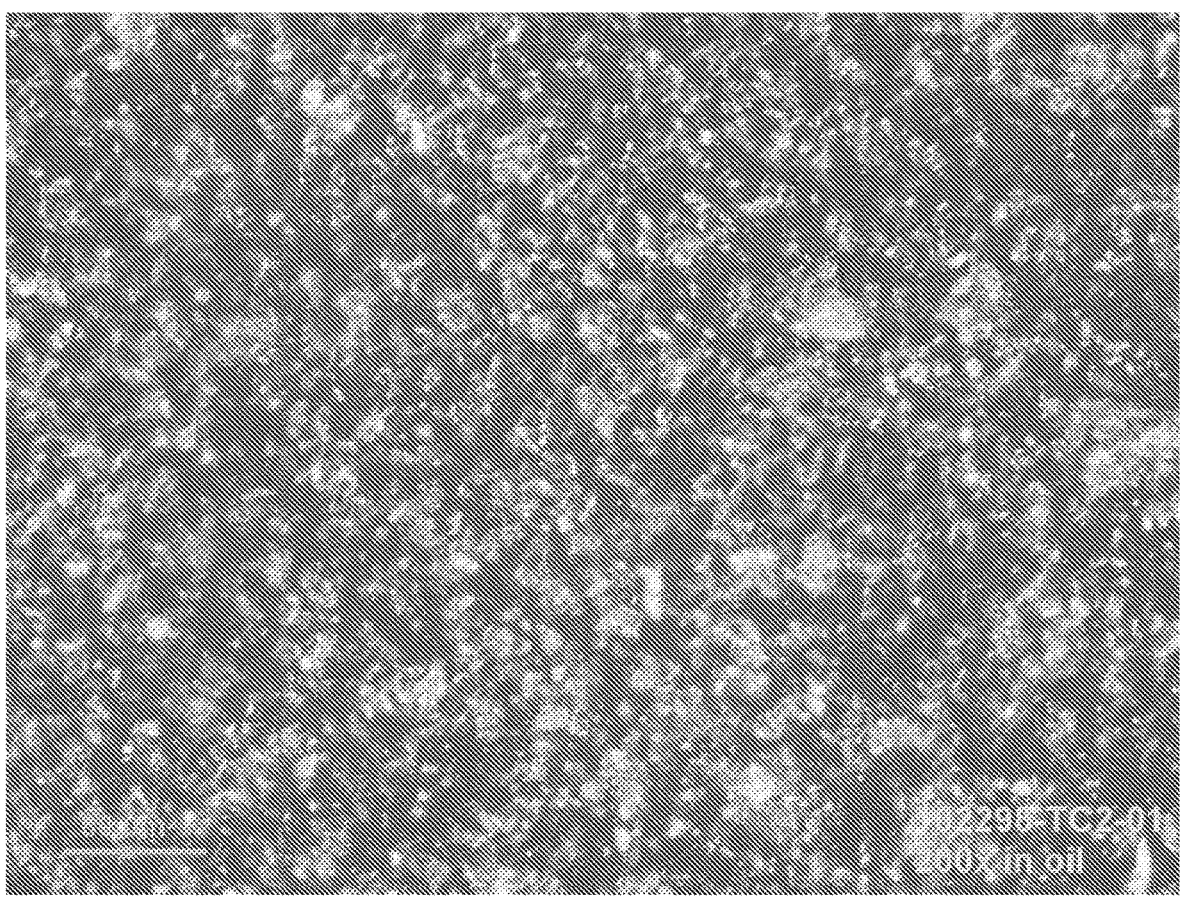
FIG. 28 depicts polarized-light microscopy of Form H of Compound 1.

In one embodiment, provided herein is a solid form, e.g., Form H of Compound 1, having a DSC thermograph substantially as depicted in FIG. 27 comprising an endothermic event with a peak maximum temperature of about 56° C., and another endothermic event with a peak maximum temperature of about 94° C.

In one embodiment, provided herein is a solid form, e.g., Form H of Compound 1, having a TGA thermogram corresponding substantially to the representative TGA thermogram as depicted in FIG. 27. In certain embodiments, the crystalline form exhibits a TGA thermogram comprising a total mass loss of approximately 7.7% of the total mass of the sample when heated between approximately 25° C. and approximately 80° C. Thus, in certain embodiments, the crystalline loses about 7.7% its total mass when heated from ambient temperature to about 80° C.

Figure 25:
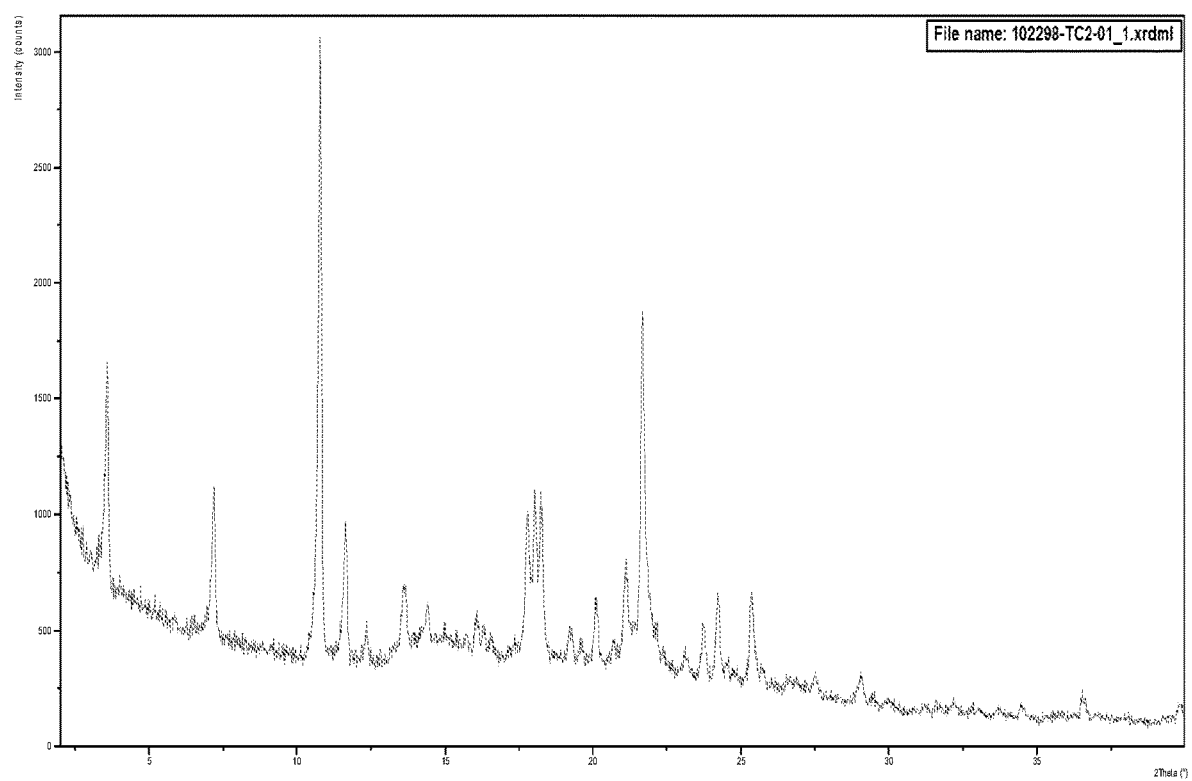
FIG. 25 depicts a PXRD pattern of Form H of Compound 1.

In certain embodiments, a solid form provided herein, e.g., Form H, is substantially crystalline, as indicated by, e.g., X-ray powder diffraction measurements. In one embodiment, provided herein is a solid form having an X-ray powder diffraction pattern (XRPD) substantially as shown in FIG. 25 (e.g., Form H). In one embodiment, a solid form provided herein, e.g., Form H, has one or more characteristic X-ray powder diffraction peaks at approximately 3.6, 7.2, 10.8, 11.7, 12.4, 13.6, 14.4, 16.1, 17.8, 18.0, 18.3, 19.2, 19.6, 20.1, 20.7, 21.2, 21.7, 23.1, 23.7, 24.2, 25.3, 27.5, 29.1, or 36.5° 2θ (±0.2° 2θ) or (±0.1° 2θ) as depicted in FIG. 25. In a specific embodiment, a solid form provided herein has one, two, three, four, five, six, or seven characteristic X-ray powder diffraction peaks at approximately 3.6, 7.2, 10.8, 17.8, 18.0, 18.3, or 21.7° 2θ (±0.2° 2θ). In certain embodiments, the solid form is Form H.

In still another embodiment, Form H is substantially pure. In certain embodiments, the substantially pure Form H is substantially free of other solid forms, including but not limited to amorphous solid. In certain embodiments, the substantially pure Form H is substantially free of Form A, Form B, Form C, Form D, Form E, Form F, Form G, or Form I. In certain embodiments, the purity of the substantially pure Form H is no less than about 95%, no less than about 96%, no less than about 97%, no less than about 98%, no less than about 98.5%, no less than about 99%, no less than about 99.5%, or no less than about 99.8%. In certain embodiments, the substantially pure Form H is substantially free of Form J, Form K, Form L, Form M, or Form N.

In certain embodiments, Form H is mixed with other solid forms, including but not limited to the amorphous solid. In certain embodiments, Form H is mixed with at least one of Form A, Form B, Form C, Form D, Form E, Form F, Form G, or Form I. In certain embodiments, Form H is mixed with at least one of Form A, Form B, Form C, Form D, Form E, Form F, Form G, Form I, Form J, Form K, Form L, Form M, or Form N.

In one embodiment, Form H comprises a free base of Compound 1. In one embodiment, Form H comprises a free acid of Compound 1. In one embodiment, Form H comprises a zwitterion of Compound 1.

(j) Form I

In certain embodiments, provided herein is Form I.

In one embodiment, Form I is a solid form comprising Compound 1. In one embodiment, Form I is solvated by water. In one embodiment, Form I is a hydrate. In one embodiment, Form I is crystalline. In one embodiment, Form I is moderately crystalline.

In certain embodiments, provided herein are methods for making Form I, comprising: 1) obtaining a solution of Compound 1 in a solvent or a solvent system at a first temperature (e.g., ambient temperature); 2) adding an anti-solvent into the saturated solution at the first temperature; 3) stirring the solution for a period of time (e.g., about 4 days) while cycling the temperature (e.g., between about 20° C. and about 50° C.); and 4) evaporating the solution under a flow of nitrogen gas at a certain temperature (e.g., ambient temperature) over a period of time (e.g., 14 days) to yield Form I of Compound 1. In certain embodiments, the solvent is dimethylformamide and the anti-solvent is water.

In certain embodiments, a method of making Form I comprises drying Form H with nitrogen gas bleed for a period of time (e.g., 14 days).

Figure 30:
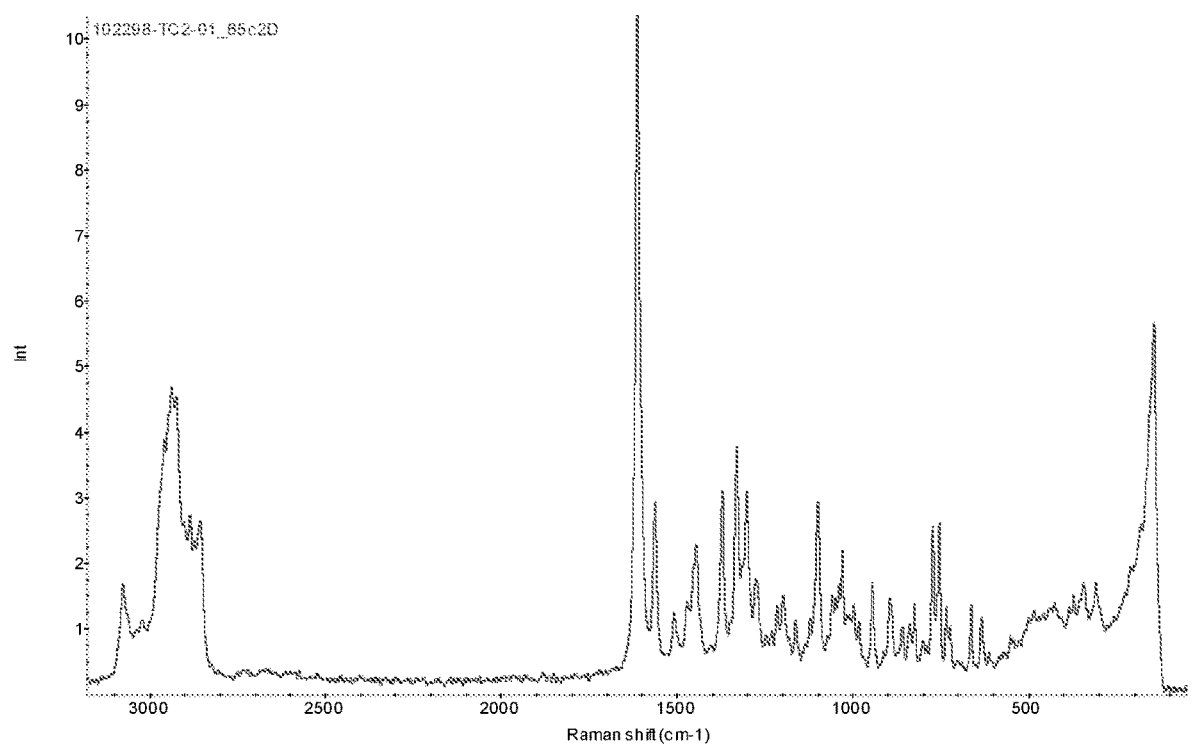
FIG. 30 depicts an FT-Raman spectrum of Form I of Compound 1.

In one embodiment, provided herein is Form I having an FT-Raman Spectrum as depicted in FIG. 30.

Figure 31:
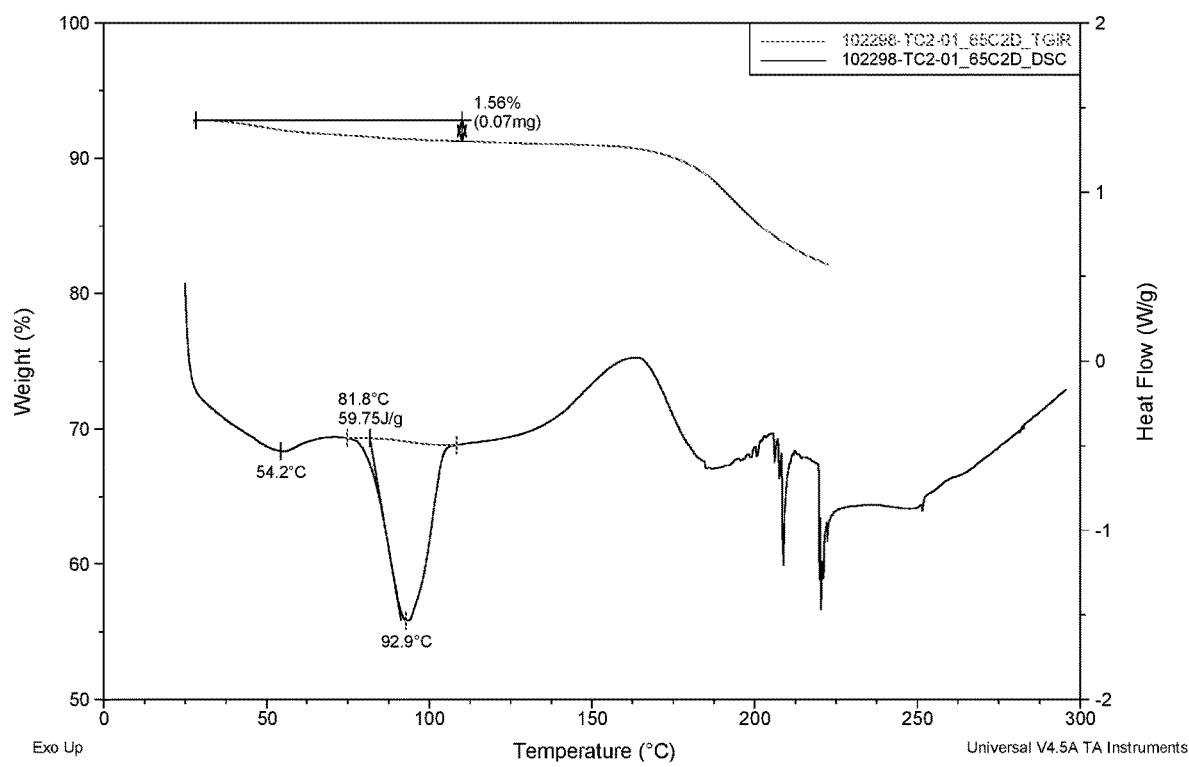
FIG. 31 depicts differential scanning calorimetry/thermal gravimetric analysis of Form I of Compound 1.
Figure 32:
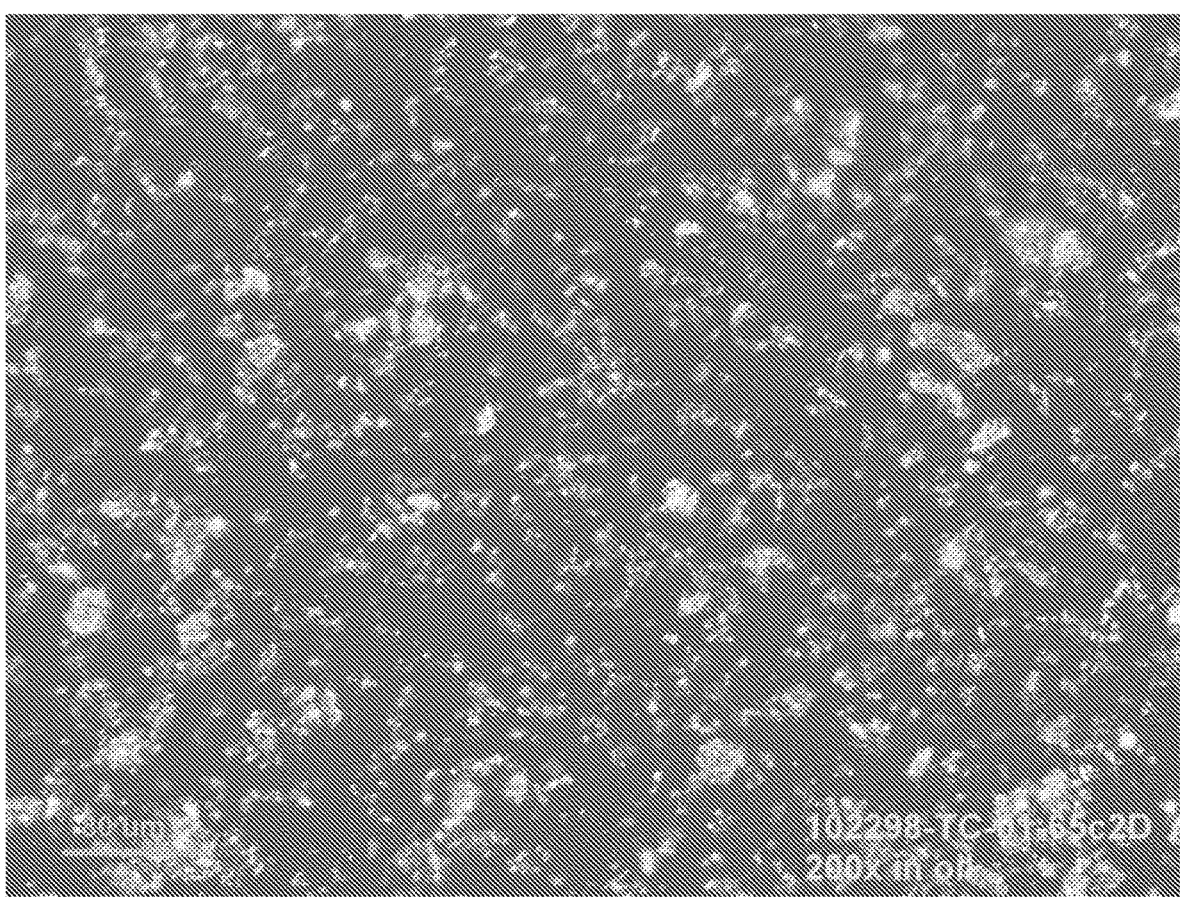
FIG. 32 depicts polarized-light microscopy of Form I of Compound 1.

In one embodiment, provided herein is a solid form, e.g., Form I of Compound 1, having a DSC thermograph substantially as depicted in FIG. 31 comprising an endothermic event with a peak maximum temperature at about 54° C. In one embodiment, provided herein is a solid form, e.g., Form I of Compound 1, having a DSC endothermic event with an onset temperature at about 82° C. and a peak maximum temperature at about 93° C.

In one embodiment, provided herein is a solid form, e.g., Form I of Compound 1, having a TGA thermogram corresponding substantially to the representative TGA thermogram as depicted in FIG. 31. In certain embodiments, the crystalline form exhibits a TGA thermogram comprising a total mass loss of approximately 1.6% of the total mass of the sample when heated between approximately 25° C. and approximately 110° C. Thus, in certain embodiments, the crystalline loses about 1.6% its total mass when heated from ambient temperature to about 110° C.

Figure 29:
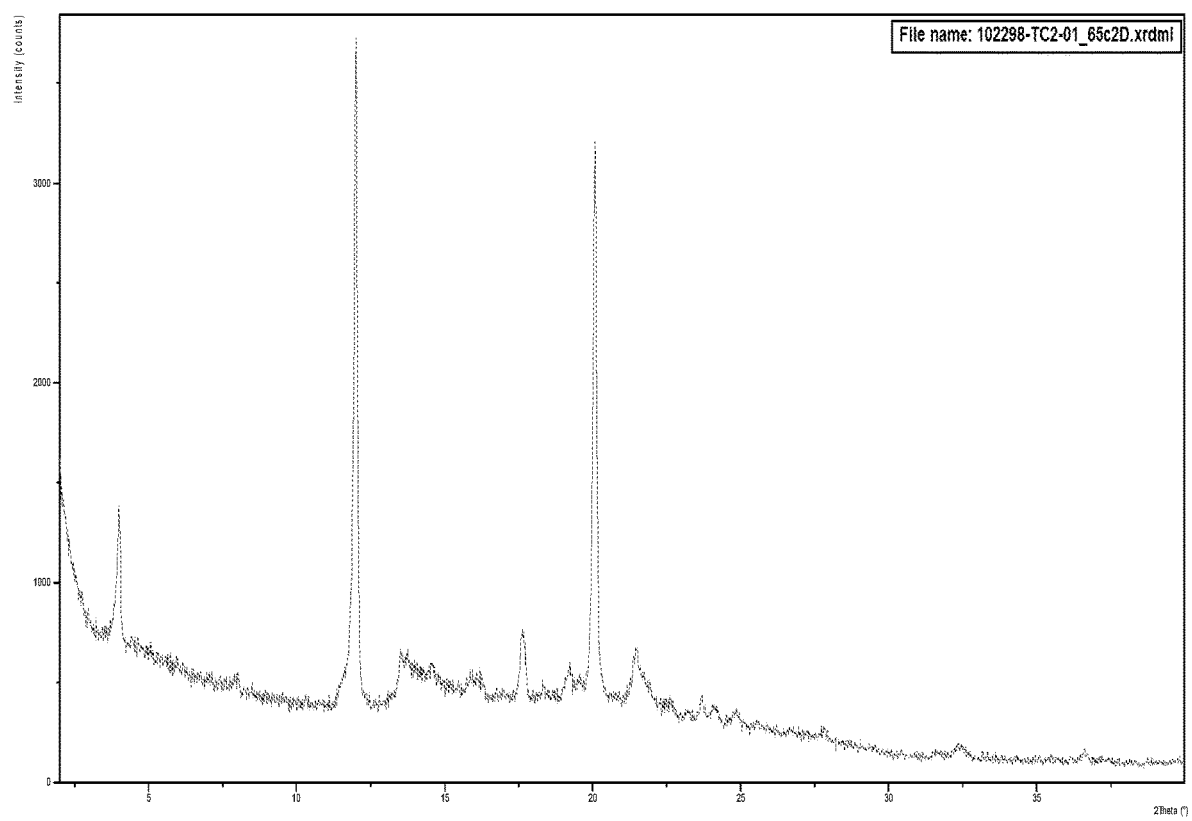
FIG. 29 depicts a PXRD pattern of Form I of Compound 1.

In certain embodiments, a solid form provided herein, e.g., Form I, is substantially crystalline, as indicated by, e.g., X-ray powder diffraction measurements. In one embodiment, provided herein is a solid form having an X-ray powder diffraction pattern (XRPD) substantially as shown in FIG. 29 (e.g. Form I). In one embodiment, a solid form provided herein, e.g., Form I, has one or more characteristic X-ray powder diffraction peaks at approximately 4.0, 8.0, 12.0, 13.5, 17.6, 19.2, 20.1, 21.5, or 32.4° 2θ (±0.2° 2θ) or (±0.1° 2θ) as depicted in FIG. 29. In a specific embodiment, a solid form provided herein has one, two, three, four, or five characteristic X-ray powder diffraction peaks at approximately 4.0, 12.0, 17.6, 20.1, or 21.5° 2θ (±0.2° 2θ). In certain embodiments, the solid form is Form I.

In still another embodiment, Form I is substantially pure. In certain embodiments, the substantially pure Form I is substantially free of other solid forms, including but not limited to amorphous solid. In certain embodiments, the substantially pure Form I is substantially free of Form A, Form B, Form C, Form D, Form E, Form F, Form G, or Form H. In certain embodiments, the purity of the substantially pure Form I is no less than about 95%, no less than about 96%, no less than about 97%, no less than about 98%, no less than about 98.5%, no less than about 99%, no less than about 99.5%, or no less than about 99.8%. In certain embodiments, the substantially pure Form I is substantially free of Form J, Form K, Form L, Form M, or Form N.

In certain embodiments, Form I is mixed with other solid forms, including but not limited to the amorphous solid. In certain embodiments, Form I is mixed with at least one of Form A, Form B, Form C, Form D, Form E, Form F, Form G, or Form H. In certain embodiments, Form I is mixed with at least one of Form A, Form B, Form C, Form D, Form E, Form F, Form G, Form H, Form J, Form K, Form L, Form M, or Form N.

In one embodiment, Form I comprises a free base of Compound 1. In one embodiment, Form I comprises a free acid of Compound 1. In one embodiment, Form I comprises a zwitterion of Compound 1.

(k) Form J

In certain embodiments, provided herein is Form J.

In one embodiment, Form J is a solid form of Compound 1. In one embodiment, Form J is crystalline.

In certain embodiments, provided herein are methods for making Form J, comprising 1) mixing Compound 1 with a solvent or solvent system; 2) sonicating the mixture; 3) filtering the mixture; 4) evaporating the filtrate to dryness; 5) adding solvent to the dried sample to obtain a solution; 6) stirring the solution at a certain temperature for a certain time; 7) filtering the mixture; and 8) drying the resulting solid in a vacuum oven to yield Form J of Compound 1. In certain embodiments, the solvent is ethyl methyl ketone. In certain embodiments, the certain temperature is ambient temperature and the certain time is about one day.

In certain embodiments, provided herein are methods for making Form J, comprising: 1) mixing an amount of Compound 1 (e.g., about 80 mg) with an amount of ethyl methyl ketone (e.g., 11 mL); 2) sonicating for period of time (e.g., 5 minutes); 3) filtering via 0.2 um PTFE-membraned syringe filter; 4) evaporating the filtrate to dryness under nitrogen purge; 5) adding an amount of ethyl methyl ketone (e.g., 0.6 mL) to the sample; 6) capping the sample and stirring at a speed (e.g., 500 rotations per minute) at a temperature (e.g., ambient temperature) for a period of time (e.g., about a day); 7) collecting solids from the sample by filtration (e.g., via a 0.2 μm Nylon-membraned centrifuge tube filter) and drying the collected solids in a vacuum oven at a temperature (e.g., 35° C.) for a period of time (e.g., about a day) to yield Form J of Compound 1.

Figure 34:
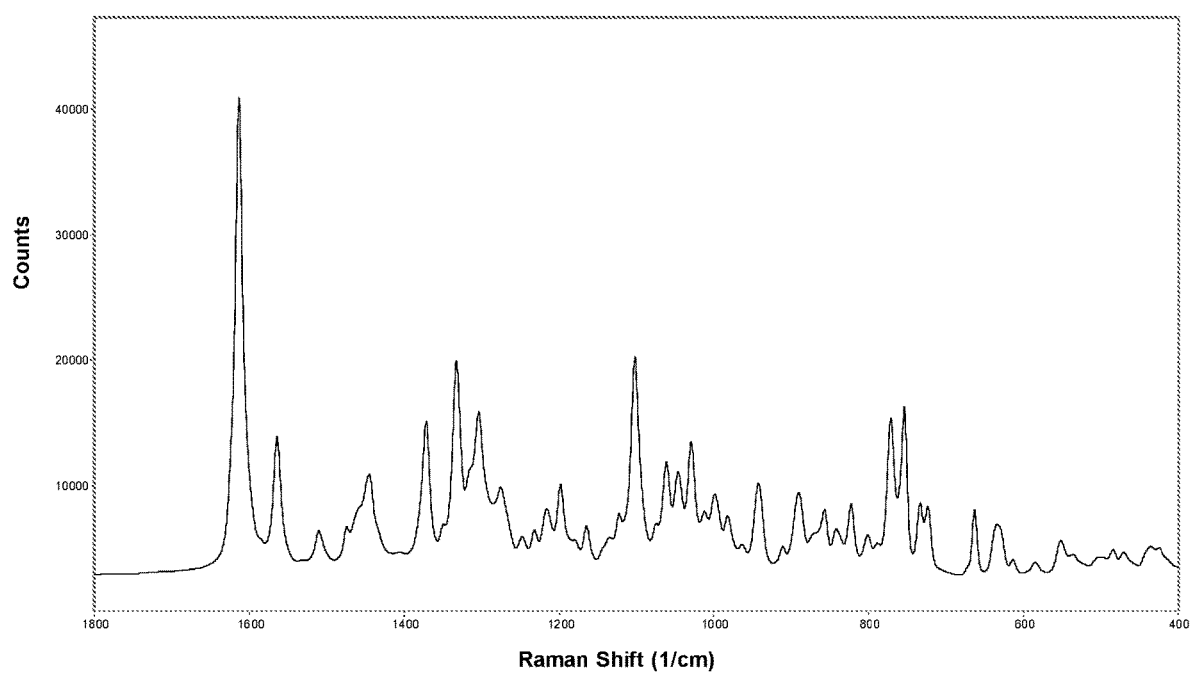
FIG. 34 depicts a Raman spectrum of Form J of Compound 1.

In one embodiment, provided herein is Form J having a Raman Spectrum as depicted in FIG. 34.

Figure 35:
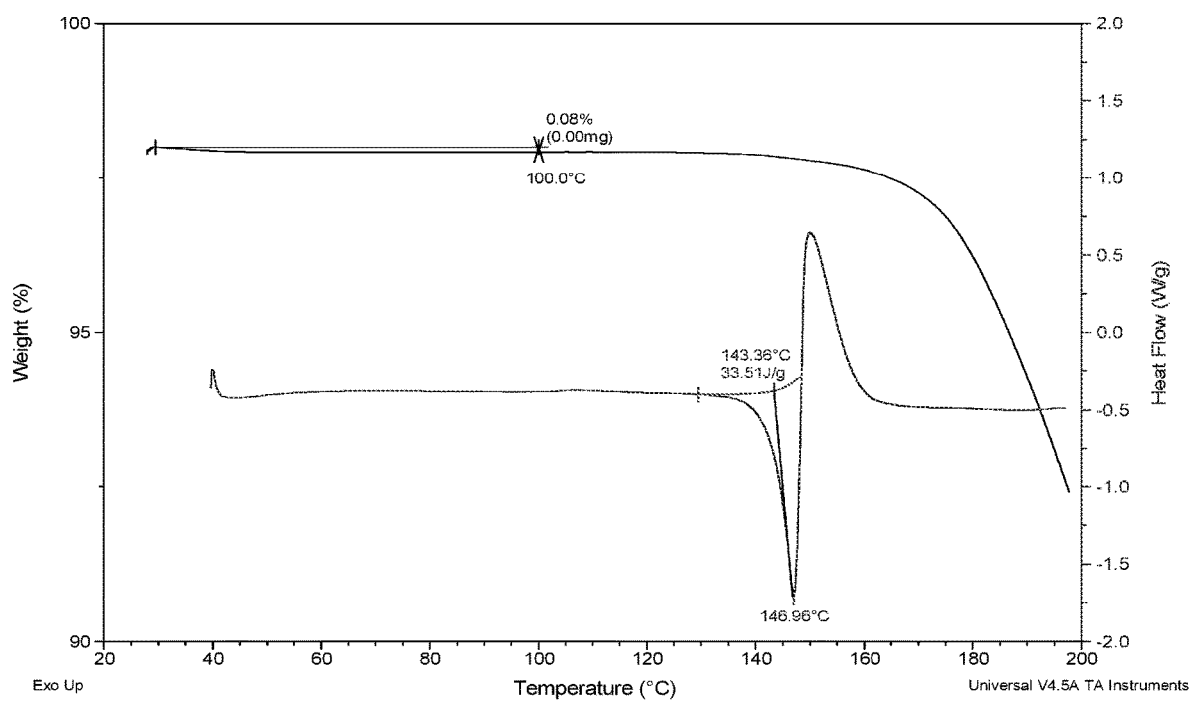
FIG. 35 depicts differential scanning calorimetry/thermal gravimetric analysis of Form J of Compound 1.

In one embodiment, provided herein is a solid form, e.g., Form J of Compound 1, having a DSC thermograph substantially as depicted in FIG. 35 comprising an endothermic event with an onset temperature of 143.4° C.

In one embodiment, provided herein is a solid form, e.g., Form J of Compound 1, having a TGA thermogram corresponding substantially to the representative TGA thermogram as depicted in FIG. 35. In certain embodiments, the crystalline form exhibits a TGA thermogram comprising a total mass loss of approximately 0.1% of the total mass of the sample when heated to 100° C. Thus, in certain embodiments, the crystalline form loses about 0.1% its total mass when heated from about ambient temperature to about 100° C.

Figure 33:
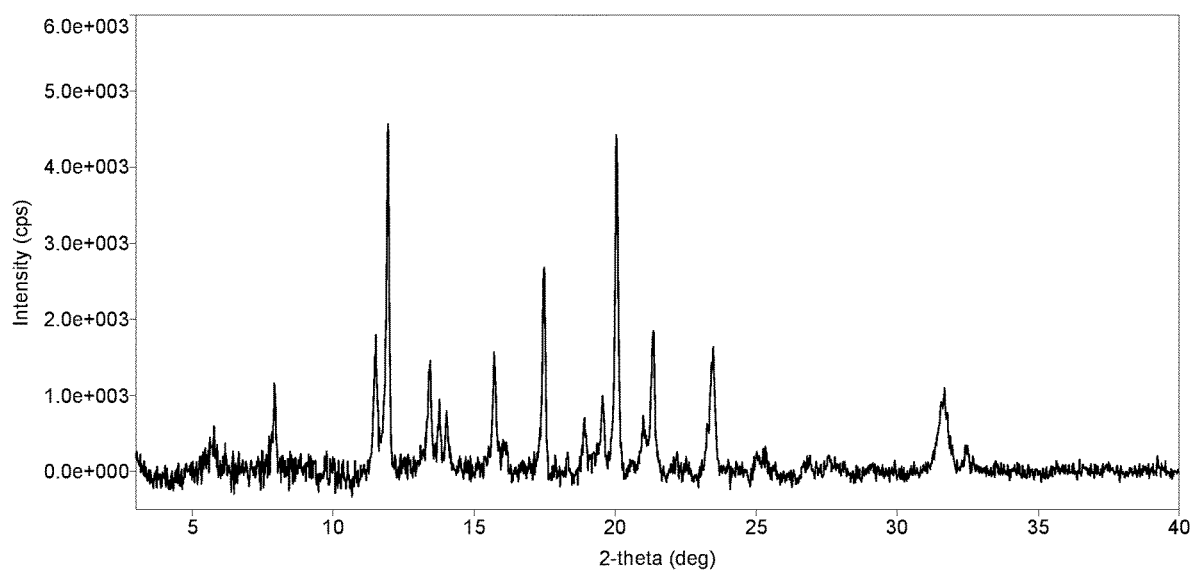
FIG. 33 depicts a PXRD pattern of Form J of Compound 1.

In certain embodiments, a solid form provided herein, e.g., Form J, is substantially crystalline, as indicated by, e.g., X-ray powder diffraction measurements. In one embodiment, provided herein is a solid form having an X-ray powder diffraction pattern (XRPD) substantially as shown in FIG. 33 (e.g., Form J). In one embodiment, a solid form provided herein, e.g., Form J, has one or more characteristic X-ray powder diffraction peaks at approximately 7.9, 11.5, 11.9, 13.4, 13.8, 14.0, 15.7, 17.4, 18.9, 19.6, 20.0, 21.0, 21.4, or 23.5° 2θ (±0.2° 2θ) or (±0.1° 2θ) as depicted in FIG. 33. In a specific embodiment, a solid form provided herein, e.g., Form J, has one, two, three, four, five, or six characteristic X-ray powder diffraction peaks at approximately 7.9, 11.9, 13.4, 15.7, 17.4, or 20.0° 2θ (±0.2° 2θ). In certain embodiments, the solid form is Form J.

In still another embodiment, Form J is substantially pure. In certain embodiments, the substantially pure Form J is substantially free of other solid forms, including but not limited to amorphous solid. In certain embodiments, the substantially pure Form J is substantially free of Form A, Form B, Form C, Form D, Form E, Form F, Form G, Form H, Form I, Form K, Form L, Form M, or Form N. In certain embodiments, the purity of the substantially pure Form J is no less than about 95%, no less than about 96%, no less than about 97%, no less than about 98%, no less than about 98.5%, no less than about 99%, no less than about 99.5%, or no less than about 99.8%.

In certain embodiments, Form J is mixed with other solid forms, including but not limited to the amorphous solid. In certain embodiments, Form J is mixed with at least one of Form A, Form B, Form C, Form D, Form E, Form F, Form G, Form H, Form I, Form K, Form L, Form M, or Form N.

In one embodiment, Form J comprises a free base of Compound 1. In one embodiment, Form J comprises a free acid of Compound 1. In one embodiment, Form J comprises a zwitterion of Compound 1.

(l) Form K

In certain embodiments, provided herein is Form K.

In one embodiment, Form K is a solid form of Compound 1. In one embodiment, Form K is crystalline.

In certain embodiments, provided herein are methods for making Form K, comprising 1) drying Compound 1 in a vacuum oven; 2) mixing the dried Compound 1 with a solvent or solvent system; 3) filtering the mixture; 4) evaporating the filtrate until precipitates are visually observed; 5) stirring the resulting mixture at a certain temperature for a certain time; 6) filtering the mixture; and 7) drying the resulting solid in a vacuum oven to yield Form K of Compound 1. In certain embodiments, the solvent is ethyl methyl ketone. In certain embodiments, the certain temperature is ambient temperature and the certain time is about one day.

In certain embodiments, provided herein are methods for making Form K, comprising: 1) drying an amount of Compound 1 (e.g., about 130 mg) in a vacuum oven at a temperature (e.g., 35° C.) for a period of time (e.g., about 3 hours); 2) adding an amount of ethyl methyl ketone (e.g., 3.5 mL) to the sample; 3) filtering via 0.2 μm PTFE-membraned syringe filter; 4) evaporating the filtrate under nitrogen purge until precipitates were observed; 5) capping the sample and stirring at a speed (e.g., 500 rotations per minute) at a temperature (e.g., ambient temperature) for a period of time (e.g., about a day); 6) collecting solids from the sample by filtration (e.g., via a 0.2 μm Nylon-membraned centrifuge tube filter) and drying the collected solids in a vacuum oven at a temperature (e.g., 35° C.) for a period of time (e.g., about a day). to yield Form K of Compound 1.

Figure 37:
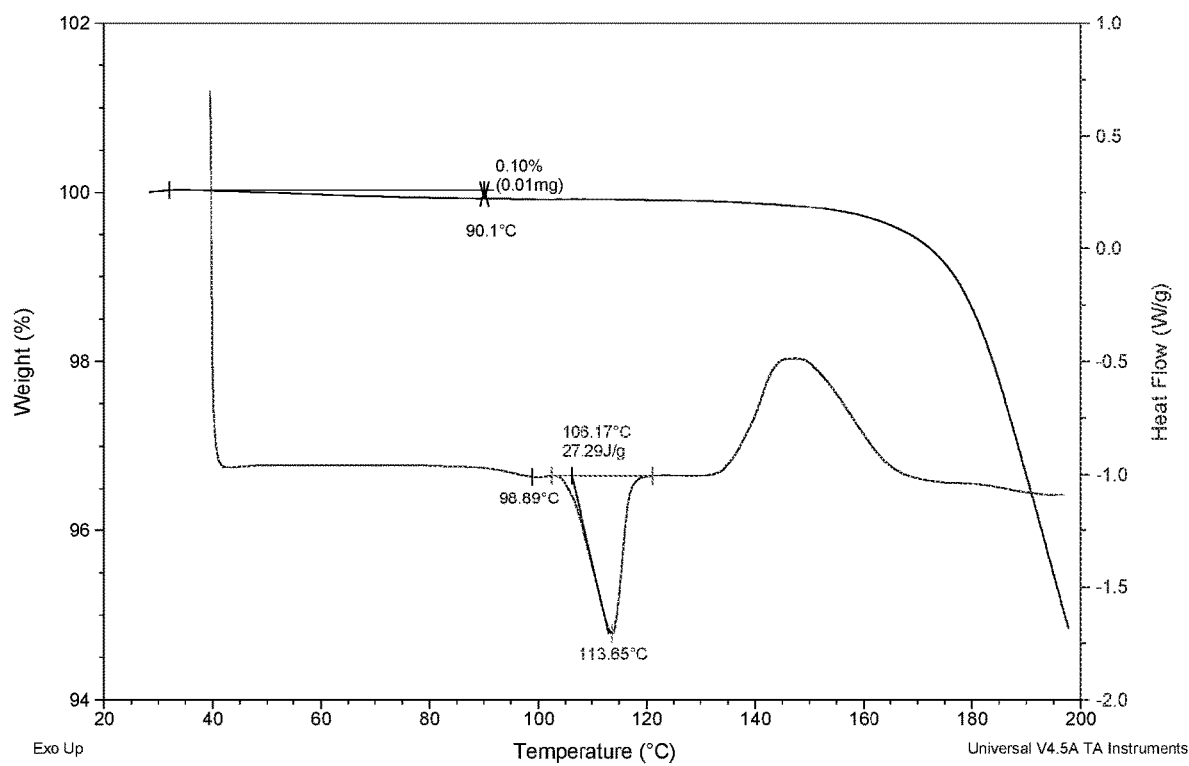
FIG. 37 depicts differential scanning calorimetry/thermal gravimetric analysis of Form K of Compound 1.

In one embodiment, provided herein is a solid form, e.g., Form K of Compound 1, having a DSC thermograph substantially as depicted in FIG. 37 comprising endothermic events with peak maximum temperatures of approximately 98.9° C. and 113.7° C., respectively.

In one embodiment, provided herein is a solid form, e.g., Form K of Compound 1, having a TGA thermogram corresponding substantially to the representative TGA thermogram as depicted in FIG. 37. In certain embodiments, the crystalline form exhibits a TGA thermogram comprising a total mass loss of approximately 0.1% of the total mass of the sample when heated to 90° C. Thus, in certain embodiments, the crystalline form loses about 0.1% its total mass when heated from about ambient temperature to about 90° C.

Figure 36:
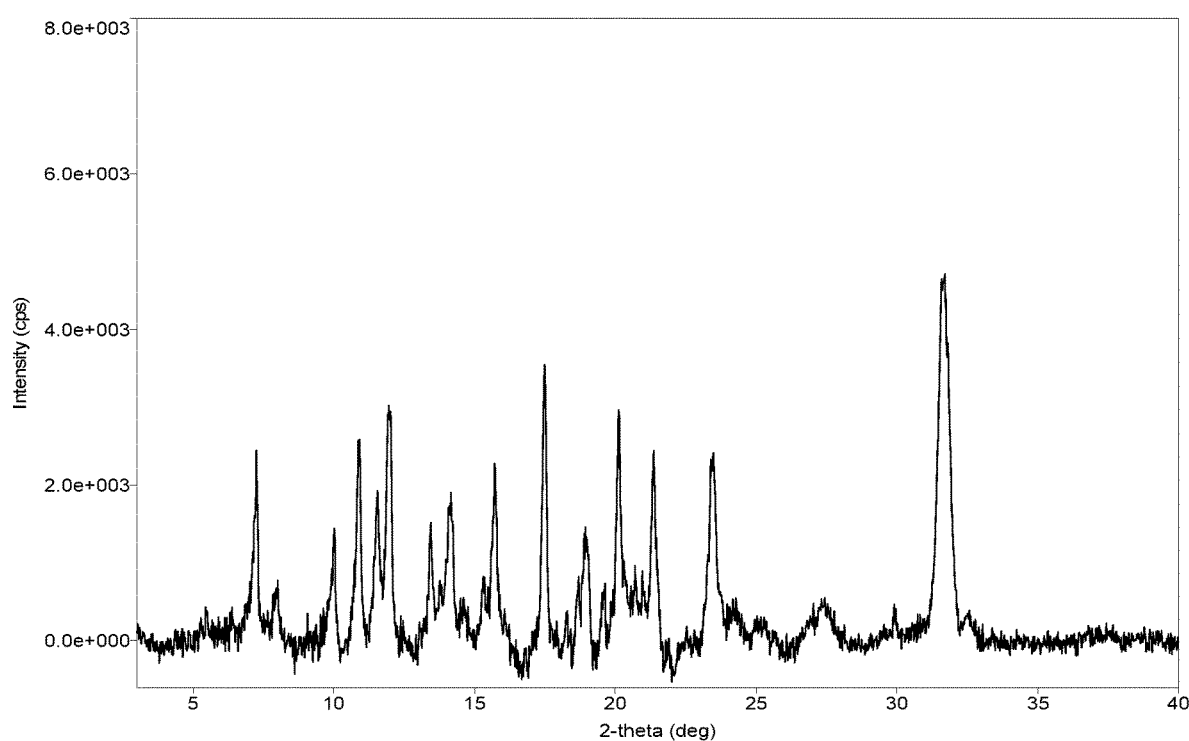
FIG. 36 depicts a PXRD pattern of Form K of Compound 1.

In certain embodiments, a solid form provided herein, e.g., Form K, is substantially crystalline, as indicated by, e.g., X-ray powder diffraction measurements. In one embodiment, provided herein is a solid form having an X-ray powder diffraction pattern (XRPD) substantially as shown in FIG. 36 (e.g., Form K). In one embodiment, a solid form provided herein, e.g., Form K, has one or more characteristic X-ray powder diffraction peaks at approximately 7.3, 8.0, 10.0, 10.9, 11.5, 12.0, 13.4, 14.1, 15.7, 17.5, 19.0, 20.1, 21.3, or 23.5° 2θ (±0.2° 2θ) or (±0.1° 2θ) as depicted in FIG. 36. In a specific embodiment, a solid form provided herein, e.g., Form K, has one, two, three, four, five, six, or seven characteristic X-ray powder diffraction peaks at approximately 7.3, 8.0, 10.0, 10.9, 12.0, 17.5, or 20.1° 2θ (±0.2° 2θ). In certain embodiments, the solid form is Form K.

In still another embodiment, Form K is substantially pure. In certain embodiments, the substantially pure Form K is substantially free of other solid forms, including but not limited to amorphous solid. In certain embodiments, the substantially pure Form K is substantially free of Form A, Form B, Form C, Form D, Form E, Form F, Form G, Form H, Form I, Form J, Form L, Form M, or Form N. In certain embodiments, the purity of the substantially pure Form K is no less than about 95%, no less than about 96%, no less than about 97%, no less than about 98%, no less than about 98.5%, no less than about 99%, no less than about 99.5%, or no less than about 99.8%.

In certain embodiments, Form K is mixed with other solid forms, including but not limited to the amorphous solid. In certain embodiments, Form K is mixed with at least one of Form A, Form B, Form C, Form D, Form E, Form F, Form G, Form H, Form I, Form J, Form L, Form M, or Form N.

In one embodiment, Form K comprises a free base of Compound 1. In one embodiment, Form K comprises a free acid of Compound 1. In one embodiment, Form K comprises a zwitterion of Compound 1.

(m) Form L

In certain embodiments, provided herein is Form L.

In one embodiment, Form L is a solid form of Compound 1. In one embodiment, Form L is crystalline.

In certain embodiments, provided herein are methods for making Form L, comprising 1) drying a solid form of Compound 1 described herein (e.g., Form K) in a vacuum oven at a certain temperature for a certain time; 2) heating a portion of the dried solid at a certain rate on DSC in a vessel to yield Form L of Compound 1. In certain embodiments, the certain temperature is 35° C. and the certain time is two days. In certain embodiments, the portion of the dried solid is heated to 121° C. at a rate of 10° C./min. In certain embodiments, the vessel is a crimped aluminum pan with a pin hole on its lid.

In certain embodiments, provided herein are methods for making Form L, comprising: 1) drying Form K of Compound 1 in a vacuum oven at a temperature (e.g., 35° C.) for a period of time (e.g., about 2 days); 2) heating the sample to a temperature (e.g., 121° C.) at a rate (e.g., 10° C. per minute) in a crimped aluminum pan with a pin hole on its lid; and 3) collecting the solid residue to yield Form L of Compound 1.

Figure 39:
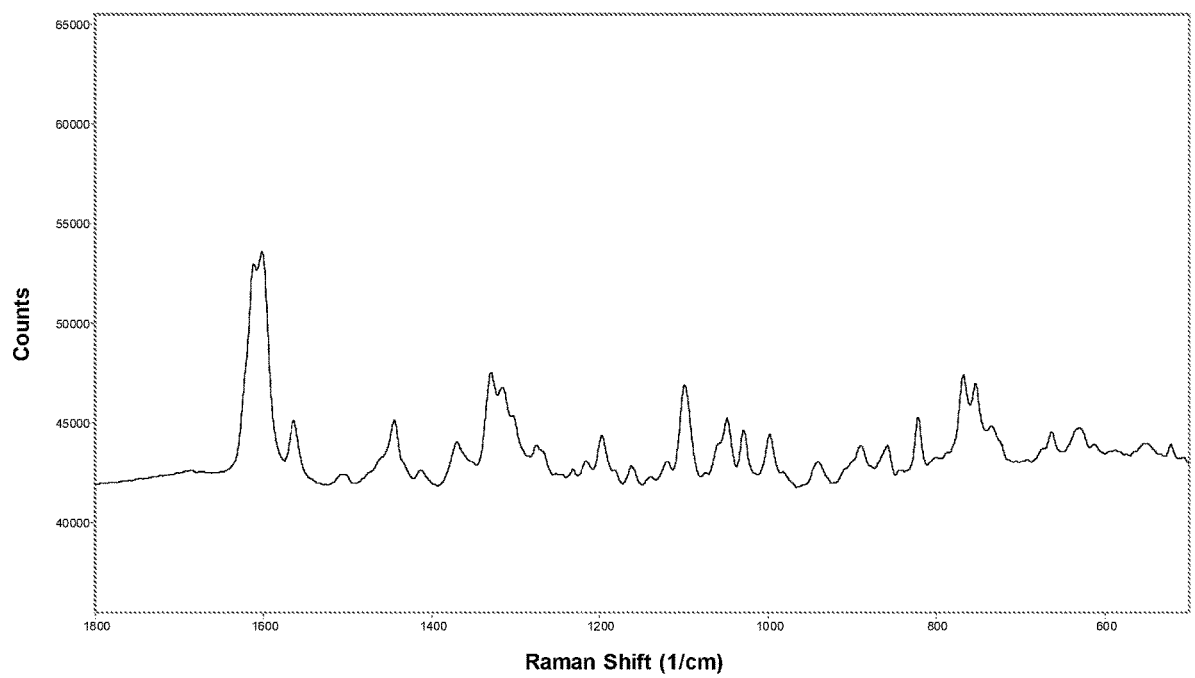
FIG. 39 depicts a Raman spectrum of Form L of Compound 1.

In one embodiment, provided herein is Form L having a Raman Spectrum as depicted in FIG. 39.

Figure 38:
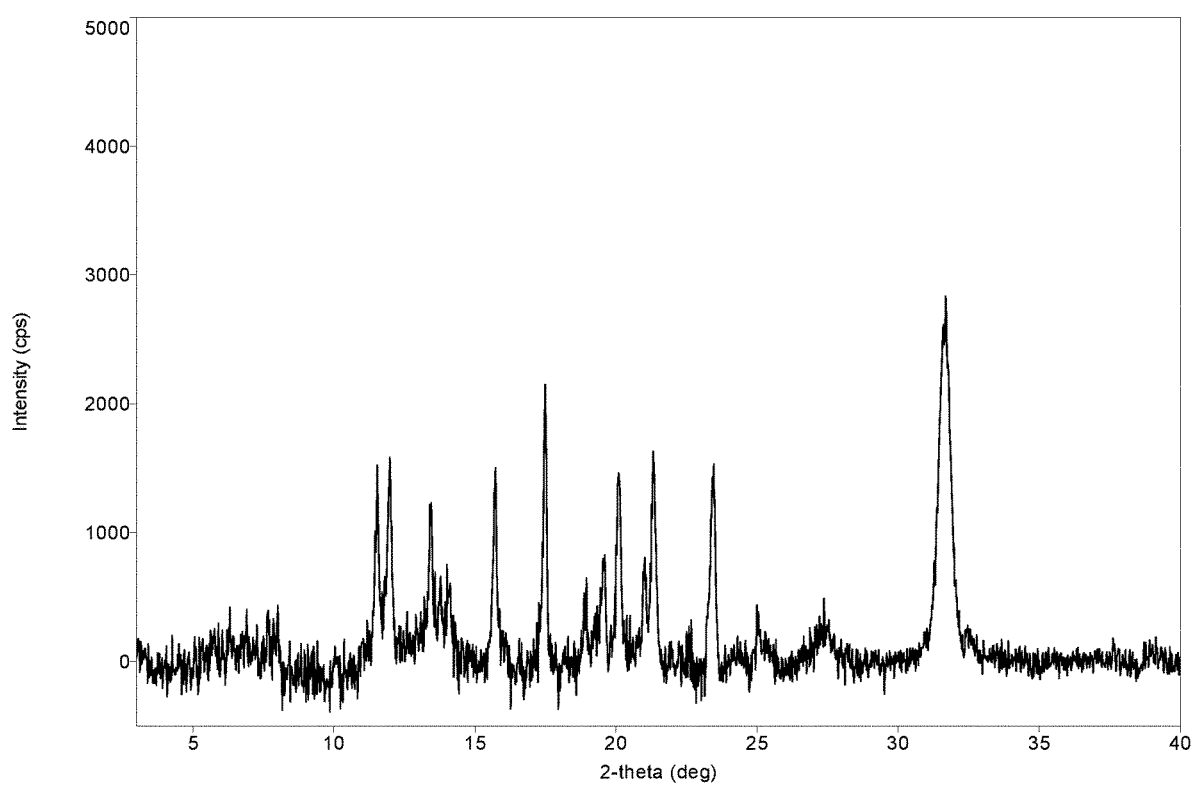
FIG. 38 depicts a PXRD pattern of Form L of Compound 1.

In certain embodiments, a solid form provided herein, e.g., Form L, is substantially crystalline, as indicated by, e.g., X-ray powder diffraction measurements. In one embodiment, provided herein is a solid form having an X-ray powder diffraction pattern (XRPD) substantially as shown in FIG. 38 (e.g., Form L). In one embodiment, a solid form provided herein, e.g., Form L, has one or more characteristic X-ray powder diffraction peaks at approximately 11.5, 12.0, 13.4, 15.7, 17.5, 19.0, 19.6, 20.1, 21.0, 21.3, or 23.5° 2θ (±0.2° 2θ) or (±0.1° 2θ) as depicted in FIG. 38. In a specific embodiment, a solid form provided herein, e.g., Form L, has one, two, three, four, five, or six characteristic X-ray powder diffraction peaks at approximately 11.5, 12.0, 13.4, 17.5, 20.1, or 21.3° 2θ (±0.2° 2θ). In certain embodiments, the solid form is Form L.

In still another embodiment, Form L is substantially pure. In certain embodiments, the substantially pure Form L is substantially free of other solid forms, including but not limited to amorphous solid. In certain embodiments, the substantially pure Form L is substantially free of Form A, Form B, Form C, Form D, Form E, Form F, Form G, Form H, Form I, Form J, Form K, Form M, or Form N. In certain embodiments, the purity of the substantially pure Form L is no less than about 95%, no less than about 96%, no less than about 97%, no less than about 98%, no less than about 98.5%, no less than about 99%, no less than about 99.5%, or no less than about 99.8%.

In certain embodiments, Form L is mixed with other solid forms, including but not limited to the amorphous solid. In certain embodiments, Form L is mixed with at least one of Form A, Form B, Form C, Form D, Form E, Form F, Form G, Form H, Form I, Form J, Form K, Form M, or Form N.

In one embodiment, Form L comprises a free base of Compound 1. In one embodiment, Form L comprises a free acid of Compound 1. In one embodiment, Form L comprises a zwitterion of Compound 1.

(n) Form M

In certain embodiments, provided herein is Form M.

In one embodiment, Form M is a solid form of Compound 1. In one embodiment, Form M is crystalline.

In certain embodiments, provided herein are methods for making Form M, comprising 1) drying a solid form of Compound 1 described herein (e.g., Form K) in a vacuum oven at a certain temperature for a certain time; 2) heating a portion of the dried solid at a certain rate on DSC in a vessel to yield Form M of Compound 1. In certain embodiments, the certain temperature is 35° C. and the certain time is two days. In certain embodiments, the portion of the dried solid is heated to 102° C. at a rate of 10° C./min. In certain embodiments, the vessel is a crimped aluminum pan with a pin hole on its lid.

In certain embodiments, provided herein are methods for making Form M, comprising: 1) drying Form K of Compound 1 in a vacuum oven at a temperature (e.g., 35° C.) for a period of time (e.g., about 2 days); 2) heating the sample to a temperature (e.g., 102° C.) at a rate (e.g., 10° C. per minute) in a crimped aluminum pan with a pin hole on its lid; and 3) collecting the solid residue to yield Form M of Compound 1.

Figure 41:
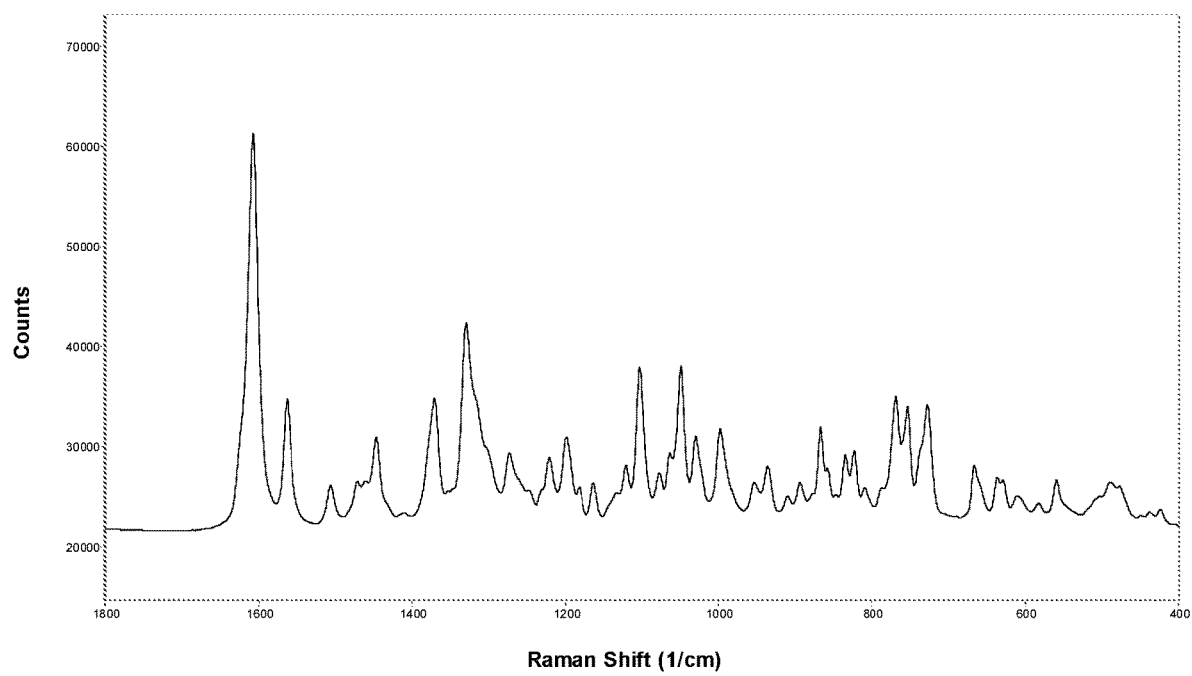
FIG. 41 depicts a Raman spectrum of Form M of Compound 1.

In one embodiment, provided herein is Form M having a Raman Spectrum as depicted in FIG. 41.

Figure 40:
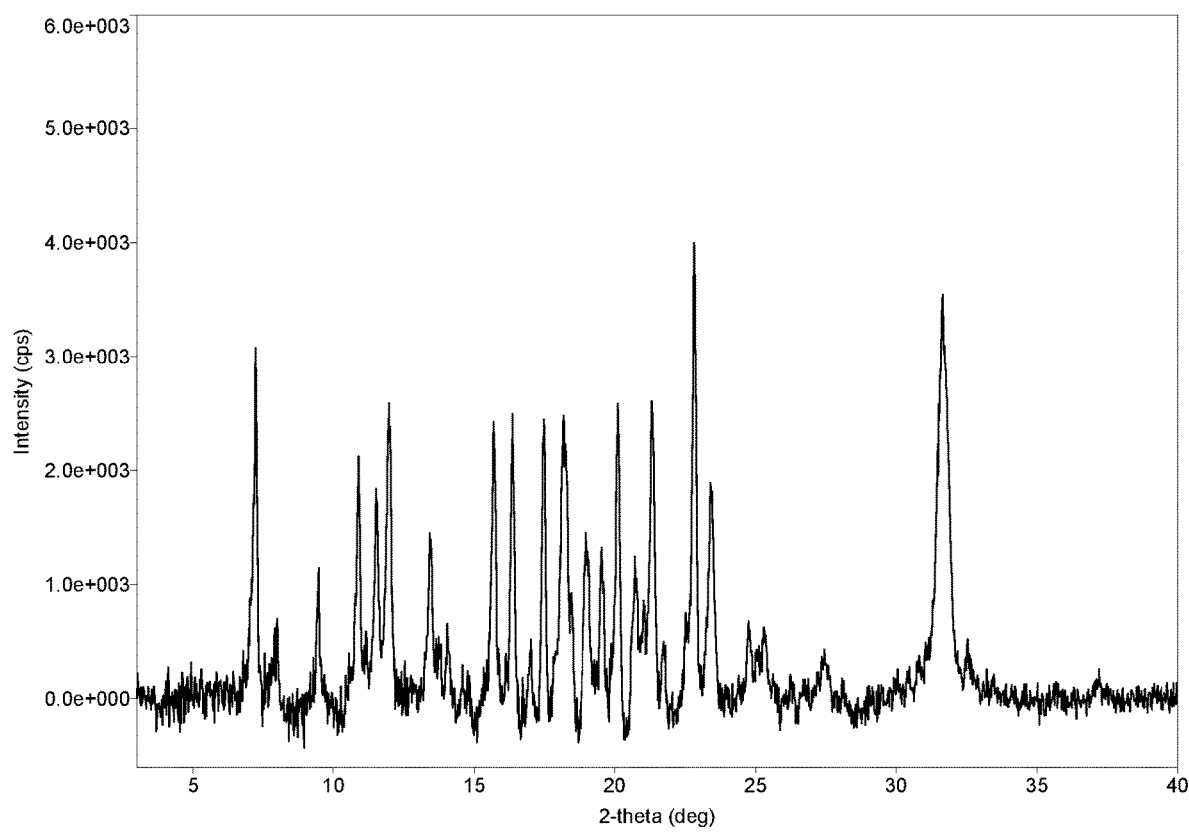
FIG. 40 depicts a PXRD pattern of Form M of Compound 1.

In certain embodiments, a solid form provided herein, e.g., Form M, is substantially crystalline, as indicated by, e.g., X-ray powder diffraction measurements. In one embodiment, provided herein is a solid form having an X-ray powder diffraction pattern (XRPD) substantially as shown in FIG. 40 (e.g., Form M). In one embodiment, a solid form provided herein, e.g., Form M, has one or more characteristic X-ray powder diffraction peaks at approximately 7.2, 8.0, 9.5, 10.9, 11.5, 12.0, 13.4, 15.7, 16.4, 17.5, 18.2, 19.0, 19.5, 20.1, 20.7, 21.3, 22.8, or 23.4° 2θ (±0.2° 2θ) or (±0.1° 2θ) as depicted in FIG. 40. In a specific embodiment, a solid form provided herein, e.g., Form M, has one, two, three, four, five, or six characteristic X-ray powder diffraction peaks at approximately 7.2, 9.5, 12.0, 16.4, 18.2, or 22.8° 2θ (±0.2° 2θ). In certain embodiments, the solid form is Form M.

In still another embodiment, Form M is substantially pure. In certain embodiments, the substantially pure Form L is substantially free of other solid forms, including but not limited to amorphous solid. In certain embodiments, the substantially pure Form M is substantially free of Form A, Form B, Form C, Form D, Form E, Form F, Form G, Form H, Form I, Form J, Form K, Form L, or Form N. In certain embodiments, the purity of the substantially pure Form M is no less than about 95%, no less than about 96%, no less than about 97%, no less than about 98%, no less than about 98.5%, no less than about 99%, no less than about 99.5%, or no less than about 99.8%.

In certain embodiments, Form M is mixed with other solid forms, including but not limited to the amorphous solid. In certain embodiments, Form M is mixed with at least one of Form A, Form B, Form C, Form D, Form E, Form F, Form G, Form H, Form I, Form J, Form K, Form L, or Form N.

In one embodiment, Form M comprises a free base of Compound 1. In one embodiment, Form M comprises a free acid of Compound 1. In one embodiment, Form M comprises a zwitterion of Compound 1.

(o) Form N

In certain embodiments, provided herein is Form N.

In one embodiment, Form N is a solid form of Compound 1. In one embodiment, Form N is crystalline.

In certain embodiments, provided herein are methods for making Form N, comprising 1) mixing a solid form of Compound 1 described herein (e.g., Form E) with a solvent or solvent system; 2) stirring the resulting mixture at a certain temperature for a certain time; 3) filtering the mixture; and 4) drying the resulting solid in a vacuum oven to yield Form N of Compound 1. In certain embodiments, the solvent is water. In some embodiments, the water is Milli-Q water. In certain embodiments, the certain temperature is ambient temperature and the certain time is five days.

In certain embodiments, provided herein are methods for making Form N, comprising: 1) mixing an amount of Form E of Compound 1 (e.g., about 8.6 mg) with an amount of water (e.g., 0.12 mL of Milli-Q water); 2) capping the sample and stirring at a speed (e.g., 400 rotations per minute) at a temperature (e.g., ambient temperature) for a period of time (e.g., about 5 days); 3) collecting solids from the sample by filtration (e.g., via a 0.2 μm Nylon-membraned centrifuge tube filter) and drying the collected solids in a vacuum oven at a temperature (e.g., 35° C.) for a period of time (e.g., about a day) to yield Form N of Compound 1.

Figure 43:
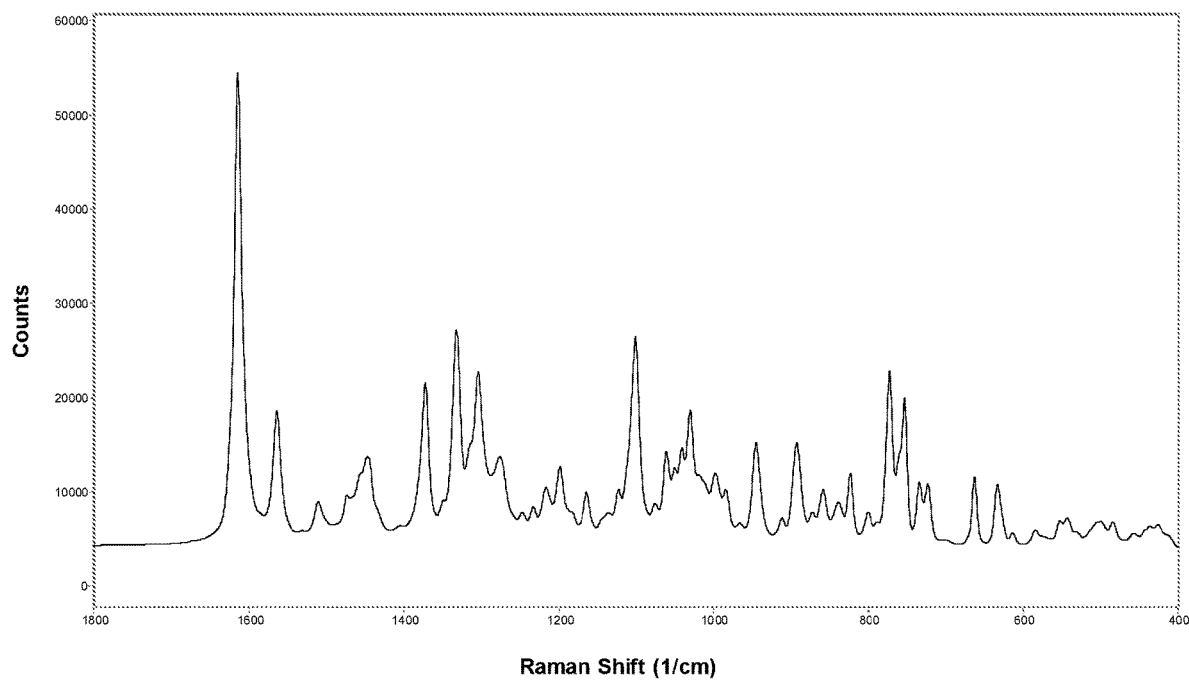
FIG. 43 depicts a Raman spectrum of Form N of Compound 1.

In one embodiment, provided herein is Form N having a Raman Spectrum as depicted in FIG. 43.

Figure 44:
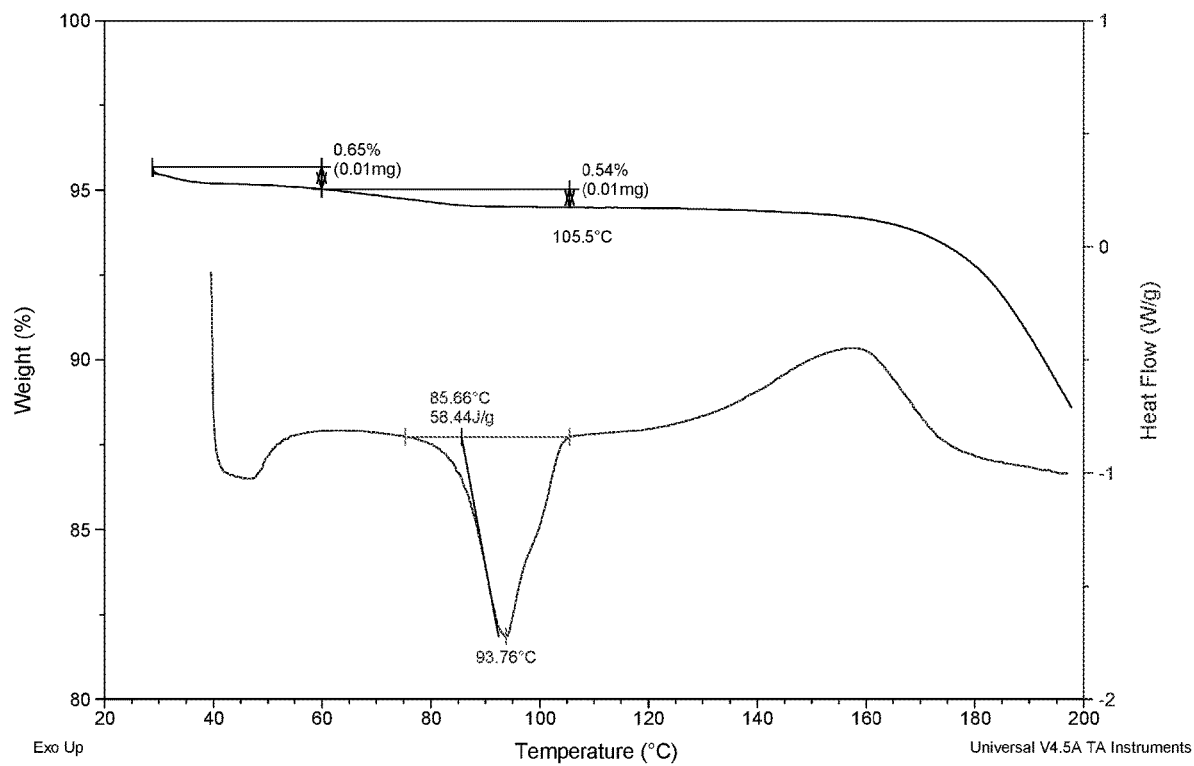
FIG. 44 depicts differential scanning calorimetry/thermal gravimetric analysis of Form N of Compound 1.

In one embodiment, provided herein is a solid form, e.g., Form N of Compound 1, having a DSC thermograph substantially as depicted in FIG. 44 comprising an endothermic event with an onset temperature of approximately 85.7° C.

In one embodiment, provided herein is a solid form, e.g., Form N of Compound 1, having a TGA thermogram corresponding substantially to the representative TGA thermogram as depicted in FIG. 44. In certain embodiments, the crystalline form exhibits a TGA thermogram comprising a total mass loss of approximately 1.2% of the total mass of the sample when heated to 105.5° C. Thus, in certain embodiments, the crystalline form loses about 1.2% of its total mass when heated from about ambient temperature to about 105.5° C.

Figure 42:
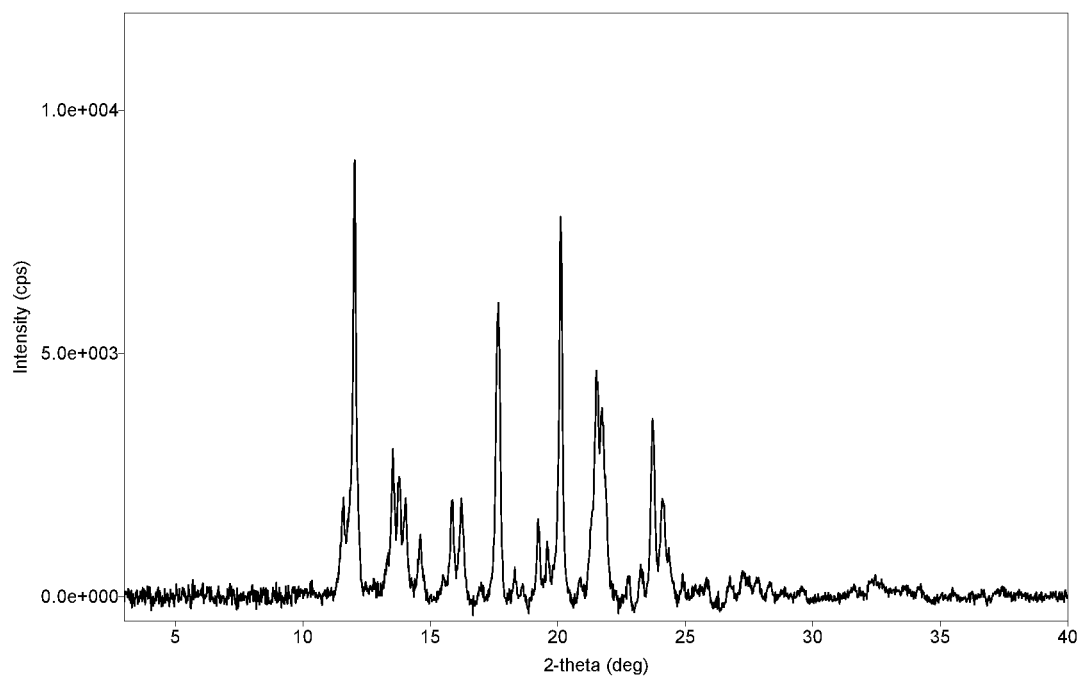
FIG. 42 depicts a PXRD pattern of Form N of Compound 1.

In certain embodiments, a solid form provided herein, e.g., Form N is substantially crystalline, as indicated by, e.g., X-ray powder diffraction measurements. In one embodiment, provided herein is a solid form having an X-ray powder diffraction pattern (XRPD) substantially as shown in FIG. 42 (e.g., Form N). In one embodiment, a solid form provided herein, e.g., Form N, has one or more characteristic X-ray powder diffraction peaks at approximately 11.6, 12.0, 13.5, 13.8, 14.0, 14.6, 15.8, 16.2, 17.7, 19.2, 19.6, 20.1, 21.6, 21.7, 23.2, 23.7, or 24.1° 2θ (±0.2° 2θ) or (±0.1° 2θ) as depicted in FIG. 42. In a specific embodiment, a solid form provided herein, e.g., Form N, has one, two, three, four, five, or six characteristic X-ray powder diffraction peaks at approximately 12.0, 13.5, 17.7, 20.1, 21.6, or 23.7° 2θ (±0.2° 2θ). In certain embodiments, the solid form is Form N.

In still another embodiment, Form N is substantially pure. In certain embodiments, the substantially pure Form N is substantially free of other solid forms, including but not limited to amorphous solid. In certain embodiments, the substantially pure Form N is substantially free of Form A, Form B, Form C, Form D, Form E, Form F, Form G, Form H, Form I, Form J, Form K, Form L, or Form M. In certain embodiments, the purity of the substantially pure Form N is no less than about 95%, no less than about 96%, no less than about 97%, no less than about 98%, no less than about 98.5%, no less than about 99%, no less than about 99.5%, or no less than about 99.8%.

In certain embodiments, Form N is mixed with other solid forms, including but not limited to the amorphous solid. In certain embodiments, Form N is mixed with at least one of Form A, Form B, Form C, Form D, Form E, Form F, Form G, Form H, Form I, Form J, Form K, Form L, or Form M.

In one embodiment, Form N comprises a free base of Compound 1. In one embodiment, Form N comprises a free acid of Compound 1. In one embodiment, Form N comprises a zwitterion of Compound 1.

5.4 Methods of Use

The solid forms and the pharmaceutical compositions comprising Compound 1, or a tautomer thereof, provided herein can be used in all the methods provided herein. The solid forms and the pharmaceutical compositions comprising Compound 1, or a tautomer thereof, provided herein can be used in the treatment of all diseases, disorders or conditions provided herein.

Provided herein are methods for treating a subject suffering from or at risk for having an autoimmune disease or chronic inflammatory disorder, wherein the method comprises administering to said subject a solid form comprising Compound 1, or a tautomer thereof, provided herein or a pharmaceutical composition thereof. In certain embodiments, the autoimmune or chronic inflammatory disorder is polymyositis, dermatomyositis, lupus nephritis, rheumatoid arthritis, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease, or multiple sclerosis. In a preferred embodiment, the multiple sclerosis is relapsing-remitting multiple sclerosis, primary progressive multiple sclerosis, secondary progressive multiple sclerosis, or relapsing secondary progressive multiple sclerosis. In one embodiment, the solid form is selected from the group consisting of Form A, Form B, Form C, Form D, Form E, Form F, Form G, Form H, or Form I. In one embodiment, the solid form is selected from the group consisting of Form J, Form K, Form L, Form M, or Form N.

In another embodiment, provided herein are methods for treating a subject suffering from or at risk for having a neurological disorder, wherein the method comprises administering to said subject a solid form comprising Compound 1, or a tautomer thereof, provided herein or a pharmaceutical composition thereof. In one embodiment, the neurological disorder is Rett Syndrome. In one embodiment, the solid form is selected from the group consisting of Form A, Form B, Form C, Form D, Form E, Form F, Form G, Form H, or Form I. In one embodiment, the solid form is selected from the group consisting of Form J, Form K, Form L, Form M, or Form N.

In another embodiment, provided herein are methods for treating a subject suffering from or at risk for renal or hepatic impairment, wherein the method comprises administering to said subject a solid form comprising Compound 1, or a tautomer thereof, provided herein or a pharmaceutical composition thereof. In one embodiment, the solid form is selected from the group consisting of Form A, Form B, Form C, Form D, Form E, Form F, Form G, Form H, or Form I. In one embodiment, the solid form is selected from the group consisting of Form J, Form K, Form L, Form M, or Form N.

In another embodiment, provided herein are methods for treating a subject suffering from or at risk for a disease or disorder mediated by lymphocyte interactions, wherein the method comprises administering to said subject a solid form comprising Compound 1, or a tautomer thereof, provided herein or a pharmaceutical composition thereof. In certain embodiments, the disease or disorder mediated by lymphocyte interactions is, for example, in transplantation, acute or chronic rejection of cell, tissue or organ allo- or xenografts or delayed graft function, graft versus host disease; autoimmune diseases, e.g., rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g., allergic asthma, atopic dermatitis, allergic rhinitis/conjunctivitis, allergic contact dermatitis; inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g., myocardial infarction, stroke, gut ischemia, renal failure or hemorrhage shock, traumatic shock; T cell lymphomas or T cell leukemias; infectious diseases, e.g., toxic shock (e.g., superantigen induced), septic shock, adult respiratory distress syndrome or viral infections, e.g., AIDS, viral hepatitis, chronic bacterial infection; muscle diseases, e.g., polymyositis; or senile dementia. Examples of cell, tissue or solid organ transplants include, e.g., pancreatic islets, stem cells, bone marrow, corneal tissue, neuronal tissue, heart, lung, combined heart-lung, kidney, liver, bowel, pancreas, trachea or oesophagus. In one embodiment, the solid form is selected from the group consisting of Form A, Form B, Form C, Form D, Form E, Form F, Form G, Form H, or Form I. In one embodiment, the solid form is selected from the group consisting of Form J, Form K, Form L, Form M, or Form N.

In another embodiment, provided herein are methods for the treatment of a disease or disorder associated with sphingosine 1-phosphate, wherein the method comprises administering to said subject a solid form comprising Compound 1, or a tautomer thereof, provided herein or a pharmaceutical composition thereof. In certain embodiments, the disease or disorder associated with sphingosine 1-phosphate is multiple sclerosis, relapse-remitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, or Graves' disease. In one embodiment, the solid form is selected from the group consisting of Form A, Form B, Form C, Form D, Form E, Form F, Form G, Form H, or Form I. In one embodiment, the solid form is selected from the group consisting of Form J, Form K, Form L, Form M, or Form N.

In another embodiment, provided herein are methods for the treatment of a disease or disorder associated with the interferon alpha receptor 1, wherein the method comprises administering to said subject a solid form comprising Compound 1, or a tautomer thereof, or a pharmaceutical composition thereof. In certain embodiments, the disease or disorder associated with the interferon alpha receptor is psoriasis, ulcerative colitis, systemic lupus, multiple sclerosis, or rheumatoid arthritis. In one embodiment, the solid form is selected from the group consisting of Form A, Form B, Form C, Form D, Form E, Form F, Form G, Form H, or Form I. In one embodiment, the solid form is selected from the group consisting of Form J, Form K, Form L, Form M, or Form N.

The compounds, compositions, methods, and uses disclosed herein are not to be limited in scope by the specific embodiments described herein. Indeed, various modifications of the compounds, compositions, methods, and uses in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entities.

5.5 Pharmaceutical Compositions

Solid forms comprising Compound 1, or a tautomer thereof, provided herein are useful for the preparation of pharmaceutical compositions, comprising an effective amount of a solid form comprising Compound 1, or a tautomer thereof, and a pharmaceutically acceptable vehicle, carrier, diluent, or excipient, or a mixture thereof. In certain embodiments, the pharmaceutically acceptable carrier is hydroxypropyl methylcellulose. In some embodiments, the pharmaceutical compositions described herein are suitable for oral, parenteral, mucosal, transdermal or topical administration.

5.6 Oral Administration

The pharmaceutical compositions provided herein may be administered orally, for example in solid, semisolid, or liquid dosage forms. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

In one embodiment, the pharmaceutically acceptable carrier or excipient is selected from the group consisting of lactose (e.g., as lactose monohydrate); microcrystalline cellulose; non-basic polymers (e.g., homopolymers of cross-linked N-vinyl-2-pyrrolidone (crospovidone), hypromellose (hydroxypropylmethyl cellulose), and ethyl cellulose);

waxes; colloidal silicon dioxide; stearic acid; hydrogenated vegetable oil; mineral oil; polyethylene glycol (e.g., polyethylene glycol 4000-6000); glyceryl palmitostearate; and glyceryl behenate. In another embodiment, the pharmaceutically acceptable carrier or excipient is microcrystalline cellulose.

Binders or granulators impart cohesiveness to a tablet to ensure the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5% to about 15% or from about 1% to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1% to about 5% by weight of a lubricant.

Suitable glidants include, but are not limited to, colloidal silicon dioxide, CAB-O-STh® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic acid, sodium benzoate, and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The solid forms and the pharmaceutical compositions comprising Compound 1, or a tautomer thereof, provided herein can be formulated as an oral dosage form. In certain embodiments the oral dosage form comprises one or more of Form A, Form B, Form C, Form D, Form E, Form F, Form G, Form H, Form I, Form J, Form K, Form L, Form M, or Form N. In certain embodiments the oral dosage form comprises at least 0.001 mg, at least 0.005 mg, at least 0.01 mg, at least 0.05 mg, at least 0.1 mg. at least 0.5 mg, at least 1.0 mg or at least 2.0 mg of Form A, Form B, Form C, Form D, Form E, Form F, Form G, Form H, Form I, Form J, Form K, Form L, Form M, or Form N.

5.7 Parenteral Administration

The pharmaceutical compositions provided herein can be administered parenterally, for example, by injection, infusion, or implantation techniques, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

6. EXAMPLES

The following Examples are presented by way of illustration, not limitation.

6.1 Analytical Methods

Powder X-ray diffraction (PXRD) patterns were obtained using a PANalytical X'Pert Pro diffractometer using Ni-filtered Cu Ka (45 kV/40 mA) radiation and a step size of 0.02° 2θ and X'celerator Real Time Multi-Strip (RTMS) detector. Configuration on the incidental beam side is a fixed divergence slit (0.25°), 0.04 radian Soller slits, anti-scatter slit (0.25°), and 10 mm beam mask. Configuration on the diffracted beam side is a fixed divergence slit (0.25°) and 0.04 radian Soller slit. Samples were mounted flat on zero-background Si wafers and covered with Kapton film to comply with safety policies.

FT-Raman spectra were collected with a Nicolet NXR9650 or NXR 960 spectrometer (Thermo Electron) equipped with 1064 nm Nd:YVO$_4$ excitation laser, InGaAs and liquid-N$_2$ cooled Ge detectors, and a MicroStage. Spectra were acquired at 4 cm$^{-1}$ resolution, 64 scans, using Happ-Genzel apodization function and 2-level zero-filling.

Differential Scanning calorimetry (DSC) was conducted with a TA Instruments Q100 differential scanning calorimeter equipped with an autosampler and a refrigerated cooling system under 40 mL/min N$_2$ purge. DSC thermograms were obtained at 15° C./min in crimped Al pans.

Polarized-light microscopy (PLM) photomicrographs were collected using an Olympus BX60 polarized-light microscope equipped with an Olympus DP70 camera.

Thermogravimetric Analysis (TGA) thermograms were obtained with a TA Instruments Q500 thermogravimetric analyzer under 40 mL/min N2 purge at 15° C./min in Al pans.

Thermogravimetric Analysis with IR Off-Gas Detection (TGA-IR) was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min N$_2$ flow and heating rate of 15° C./min in Al pans. IR spectra were collected at 4 cm$^{-1}$ resolution and 32 scans at each time point.

Proton Nuclear Magnetic Resonance CH NMR) spectra were collected using an Agilent DD2 500 MHz spectrometer with tetramethylsilane reference. Samples were dissolved in deuterated dimethyl sulfoxide.

Powder X-ray diffraction (PXRD) patterns were obtained on a Rigaku SmartLab Guidance diffractometer with Cu-Kα radiation and D/teX Ultra detector. The powder samples were deposited on a zero-background polished silicon sample holder and were spun during measurement. Measurements were performed as follows: 40 kV/44 mA tube power, 0.02° 2θ step size, 5° 2θ/min scan rate, and 3-40° 2θ scan range. Data were processed using Rigaku PDXL2 software.

Raman spectra were collected using a Raman Work Station (Kaiser Optical Systems, Inc, Ann Arbor, Mich.) with Holograms software. Data was acquired using 785 nm excitation laser with 300 mW in a reflection mode, 4 cm$^{-1}$ resolution through a 10× objective with 10 accumulations. Data were processed using Grams/AI software (Thermo Fisher Scientific Inc). Data may also be acquired using 785 nm excitation laser with 300 mW in a reflection mode, 4 cm$^{-1}$ resolution through a 10× objective.

Differential Scanning calorimetry (DSC) was conducted with a TA Instruments Q2000 differential scanning calorimeter equipped with an autosampler and a refrigerated cooling system under 40 mL/min nitrogen (N$_2$) purge. DSC thermograms were obtained at 10° C./min in crimped aluminum (Al) pans with pin holes on lids.

Thermogravimetric Analysis (TGA) thermograms were obtained with a TA Instruments Q5000 thermogravimetric analyzer under 40 mL/min N$_2$ purge at 10° C./min in Al pans.

For Examples 6.2(a) through 6.2(h) below, the analytical methods regarding PXRD, FT-Raman spectra, DSC and TGA as described in paragraphs [00291], [00292], [00293] and [00295], respectively, were employed. For Examples 6.2(i) through 6.2(m) below, the analytical methods regarding PXRD, Raman spectra, DSC and TGA as described in paragraphs [00298], [00299], [00300] and [00301], respectively, were employed.

6.2 Preparation and Analysis of Crystal Forms (a) Form A

Compound 1 (59.5 mg) was suspended in isopropyl ether (0.75 mL) and the temperature of the slurry was cycled between 5° C. and 40° C. for 72 h. The slurry was filtered to yield Form A of Compound 1.

Form A has an FT-Raman Spectrum as depicted in FIG. 2. Form A has a DSC thermograph substantially as depicted in FIG. 3, comprising an endothermic event with a peak maximum temperature of about 54° C., and a second endotherm with an onset temperature of about 102° C. Form A has a TGA thermograph as depicted in FIG. 3, comprising a total mass loss of approximately 6.2% of the total mass of the sample when heated to 150° C.

A list of X-Ray diffraction peaks for Form A is provided below in Table 1.

TABLE 1

X-Ray Diffraction Peaks for Form A.

| Two-theta angle (°) | d Space (Å) | Height (counts) |
|---|---|---|
| 2.3 | 37.813 | 4109.4 |
| 3.9 | 22.913 | 594.2 |
| 6.9 | 12.738 | 317.3 |
| 7.7 | 11.488 | 673.0 |
| 9.2 | 9.562 | 71.0 |
| 9.9 | 8.896 | 112.6 |
| 11.5 | 7.667 | 661.7 |
| 12.1 | 7.338 | 37.4 |
| 14.3 | 6.192 | 322.0 |
| 15.5 | 5.705 | 150.9 |
| 18.2 | 4.868 | 162.4 |
| 19.3 | 4.599 | 255.6 |
| 20.9 | 4.246 | 462.4 |
| 21.7 | 4.102 | 136.2 |
| 23.2 | 3.831 | 121.5 |
| 24.5 | 3.636 | 189.3 |
| 32.0 | 2.796 | 45.2 |

(b) Form B

Compound 1 (60.8 mg) was suspended in cyclohexane (0.75 mL) and the temperature of the slurry was cycled between 5° C. and 40° C. for 72 h. The slurry was filtered to yield Form B of Compound 1.

Form B has an FT-Raman Spectrum as depicted in FIG. 6. Form B has a DSC thermograph substantially as depicted in FIG. 7, comprising a first endothermic event with an onset temperature of about 40.2° C. and a peak maximum temperature of about 47.7° C. Form B has a TGA thermograph as depicted in FIG. 7, comprising a total mass loss of approximately 8.5% of the total mass of the sample when heated from approximately 25° C. and 150° C.

A list of X-Ray diffraction peaks for Form B is provided below in Table 2.

TABLE 2

X-Ray Diffraction Peaks for Form B.

| Two-theta angle (°) | d Space (Å) | Height (counts) |
|---|---|---|
| 2.3 | 37.850 | 3551.4 |
| 2.8 | 31.403 | 743.4 |
| 3.8 | 22.993 | 413.8 |
| 5.6 | 15.757 | 238.2 |
| 7.0 | 12.649 | 327.0 |
| 7.7 | 11.506 | 502.4 |
| 8.4 | 10.506 | 1254.6 |
| 9.3 | 9.495 | 75.9 |
| 11.5 | 7.669 | 464.9 |
| 14.0 | 6.305 | 259.2 |
| 14.3 | 6.188 | 190.1 |
| 15.5 | 5.712 | 103.1 |
| 18.2 | 4.867 | 95.6 |
| 19.3 | 4.605 | 165.6 |
| 20.9 | 4.246 | 281.8 |
| 21.7 | 4.095 | 93.8 |
| 22.5 | 3.946 | 90.9 |
| 23.2 | 3.842 | 142.3 |
| 24.6 | 3.625 | 107.0 |
| 32.0 | 2.793 | 24.1 |

(c) Form C

Compound 1 (61 mg) was suspended in heptane (0.75 mL) and the temperature of the slurry was cycled between 5° C. and 40° C. for 72 h. The slurry was filtered to yield Form C.

Form C has an FT-Raman Spectrum as depicted in FIG. 10. Form C has a DSC thermograph substantially as depicted in FIG. 11, comprising an endothermic event with an onset temperature of about 101.7° C. Form B has a TGA thermograph as depicted in FIG. 11, comprising a total mass loss of approximately 14.3% of the total mass of the sample when heated to about 150° C.

A list of X-Ray diffraction peaks for Form C is provided below in Table 3.

TABLE 3

X-Ray Diffraction Peaks for Form C.

| Two-theta angle (°) | d Space (Å) | Height (counts) |
|---|---|---|
| 2.2 | 40.419 | 4109.4 |
| 3.9 | 22.928 | 594.2 |
| 6.5 | 13.589 | 317.3 |
| 7.7 | 11.498 | 673.0 |
| 8.7 | 10.113 | 71.0 |
| 9.9 | 8.923 | 112.6 |
| 11.5 | 7.669 | 661.7 |
| 14.3 | 6.186 | 37.4 |
| 15.6 | 5.680 | 322.0 |
| 18.3 | 4.859 | 9004.5 |
| 19.3 | 4.606 | 368.4 |
| 20.9 | 4.242 | 404.2 |
| 21.8 | 4.084 | 466.5 |
| 23.2 | 3.831 | 60.2 |

TABLE 3-continued

X-Ray Diffraction Peaks for Form C.

| Two-theta angle (°) | d Space (Å) | Height (counts) |
|---|---|---|
| 24.5 | 3.631 | 43.7 |
| 32.0 | 2.798 | 532.5 |

(d) Form D

Compound 1 (120 mg) was suspended in dimethyl carbonate (0.5 mL) and the temperature of the slurry was cycled between 5° C. and 40° C. overnight. The slurry was filtered and dried under a blanket of nitrogen gas for 1 h. Drying under vacuum with nitrogen gas bleed at 65° C. overnight yielded Form D (50 mg) of Compound 1 as a free-flowing powder.

Form D has an FT-Raman Spectrum as depicted in FIG. 14. Form D has a DSC thermograph substantially as depicted in FIG. 15, comprising an endothermic event with an onset temperature of about 96° C. and a peak maximum temperature of about 111° C. Form D has a TGA thermograph as depicted in FIG. 15, comprising a total mass loss of approximately 0.4% of the total mass of the sample when heated from approximately 25° C. to 125° C.

A list of X-Ray diffraction peaks for Form D is provided below in Table 4.

TABLE 4

X-Ray Diffraction Peaks for Form D.

| Two-theta angle (°) | d Space (Å) | Height (counts) |
|---|---|---|
| 2.8 | 31.747 | 129.7 |
| 3.7 | 23.981 | 641.7 |
| 7.3 | 12.049 | 469.1 |
| 11.0 | 8.047 | 242.6 |
| 14.4 | 6.139 | 75.1 |
| 16.4 | 5.391 | 204.4 |
| 18.3 | 4.859 | 259.9 |
| 20.8 | 4.274 | 91.9 |
| 22.9 | 3.878 | 270.0 |

(e) Form E

Compound 1 (1.3 g) was suspended in isopropyl ether (6 mL). The slurry became a solution at 40° C., was seeded with Form E (1 mg), and temperature-cycled between 5° C. and 40° C. overnight. The slurry was filtered, washed with isopropyl ether (3×1 mL) and dried under vacuum at 65° C. with nitrogen gas bleed for 1 h to provide Form E (470 mg) of Compound 1 as a free-flowing solid.

Form E has an FT-Raman Spectrum as depicted in FIG. 18. Form E has a DSC thermograph substantially as depicted in FIG. 19, comprising a possible melting endotherm with an onset temperature of about 106° C. Form E has a TGA thermograph as depicted in FIG. 19, comprising a total mass loss of approximately 0.3% of the total mass of the sample when heated from approximately 25° C. to about 125° C.

A list of X-Ray diffraction peaks for Form E is provided below in Table 5.

TABLE 5

X-Ray Diffraction Peaks for Form E.

| Two-theta angle (°) | d Space (Å) | Height (counts) |
|---|---|---|
| 3.9 | 22.793 | 934.1 |
| 7.7 | 11.461 | 1086.7 |
| 9.9 | 8.903 | 109.1 |

TABLE 5-continued

X-Ray Diffraction Peaks for Form E.

| Two-theta angle (°) | d Space (Å) | Height (counts) |
|---|---|---|
| 11.6 | 7.653 | 1152.7 |
| 12.1 | 7.310 | 134.6 |
| 14.3 | 6.183 | 651.5 |
| 15.5 | 5.715 | 207.6 |
| 17.3 | 5.114 | 27.6 |
| 18.2 | 4.871 | 384.5 |
| 19.3 | 4.607 | 349.2 |
| 20.9 | 4.244 | 1307.1 |
| 21.7 | 4.102 | 434.1 |
| 23.3 | 3.825 | 199.5 |
| 24.5 | 3.631 | 574.0 |
| 25.3 | 3.517 | 72.1 |
| 32.0 | 2.799 | 116.1 |

(f) Form F

Compound 1 (120 mg) was suspended in dimethyl carbonate (0.5 mL) and stirred at 20° C. for 1 h. The slurry was seeded with Form D (1 mg) and stirred at 20° C. overnight. The slurry was collected by centrifugation, followed by decanting, and dried in a centrifuge evaporator overnight to yield Form F (45 mg) of Compound 1 as a crystalline solid.

Form F has an FT-Raman Spectrum as depicted in FIG. 22. Form F has a DSC thermograph substantially as depicted in FIG. 23, comprising an endothermic event with an onset temperature of about 48° C. and a peak maximum temperature of about 63° C. Form F has a TGA thermograph as depicted in FIG. 23, comprising a total mass loss of approximately 8.9% of the total mass of the sample when heated from approximately 25° C. to about 125° C.

A list of X-Ray diffraction peaks for Form F is provided below in Table 6.

TABLE 6

X-Ray Diffraction Peaks for Form F.

| Two-theta angle (°) | d Space (Å) | Height (counts) |
|---|---|---|
| 2.5 | 35.603 | 301.3 |
| 3.3 | 26.604 | 496.8 |
| 6.6 | 13.355 | 129.9 |
| 9.9 | 8.934 | 783.2 |
| 10.5 | 8.410 | 108.8 |
| 12.4 | 7.126 | 164.3 |
| 13.2 | 6.708 | 199.4 |
| 14.8 | 5.977 | 404.5 |
| 19.9 | 4.472 | 365.2 |
| 20.4 | 4.344 | 748.9 |
| 21.9 | 4.057 | 184.3 |
| 22.9 | 3.890 | 159.2 |
| 23.5 | 3.790 | 607.4 |
| 26.6 | 3.351 | 150.9 |

(g) Form H

Form E was suspended in a 10% mixture of water in acetonitrile and seeded with a small amount of Form D (1 mg) or Form I (1 mg) and the suspension was allowed to stir at ambient temperature overnight. The resulting mixture was then stirred while cycling the temperature between 5° C. and 30° C. over a period of 48 h. The resulting mixture was filtered to yield Form H of Compound 1.

Form E was suspended in a 10% mixture of water in 1-propanol and seeded with a small amount of Form D (1 mg) or Form I (1 mg) and the suspension was allowed to stir at ambient temperature overnight. The resulting mixture was then stirred while cycling the temperature between 5° C. and 30° C. over a period of 48 h. The resulting mixture was filtered to yield Form H of Compound 1.

Form H has an FT-Raman Spectrum as depicted in FIG. 26. Form H has a DSC thermograph substantially as depicted in FIG. 27, comprising an endothermic event with a peak maximum temperature of about 56° C. and a second endothermic event with a peak maximum temperature of about 94° C. Form H has a TGA thermograph as depicted in FIG. 27, comprising a total mass loss of approximately 7.7% of the total mass of the sample when heated from approximately 25° C. and 80° C.

A list of X-Ray diffraction peaks for Form H is provided below in Table 7.

TABLE 7

X-Ray Diffraction Peaks for Form H.

| Two-theta angle (°) | d Space (Å) | Height (counts) |
|---|---|---|
| 3.6 | 24.580 | 881.7 |
| 7.2 | 12.279 | 629.4 |
| 10.8 | 8.194 | 2646.7 |
| 11.7 | 7.589 | 520.9 |
| 12.4 | 7.164 | 135.3 |
| 13.6 | 6.494 | 274.5 |
| 14.4 | 6.148 | 173.8 |
| 16.1 | 5.512 | 141.2 |
| 17.8 | 4.987 | 626.5 |
| 18.0 | 4.922 | 707.3 |
| 18.3 | 4.861 | 618.1 |
| 19.2 | 4.615 | 117.0 |
| 19.6 | 4.526 | 87.0 |
| 20.1 | 4.415 | 235.3 |
| 20.7 | 4.293 | 76.9 |
| 21.2 | 4.200 | 383.0 |
| 21.7 | 4.100 | 1506.8 |
| 23.1 | 3.843 | 72.8 |
| 23.7 | 3.751 | 223.7 |
| 24.2 | 3.672 | 318.1 |
| 25.3 | 3.518 | 327.1 |
| 27.5 | 3.242 | 103.3 |
| 29.1 | 3.073 | 114.5 |
| 36.5 | 2.459 | 86.6 |

(h) Form I

Compound 1 is dissolved in dimethylformamide at ambient temperature and stirred overnight, and followed by addition of water. The resulting mixture is stirred for about 4 days while cycling the temperature between about 20° C. and about 50° C. The resulting mixture is evaporated under a blanket of nitrogen gas over 14 days to yield Form I of Compound 1.

Alternatively, Form H of Compound 1 is dried under vacuum with nitrogen gas bleed at 65° C. overnight or two days to yield Form I of Compound 1.

Form I has an FT-Raman Spectrum as depicted in FIG. 30. Form I has a DSC thermograph substantially as depicted in FIG. 31, comprising an endothermic event with an onset temperature of about 82° C. and a peak maximum temperature of about 93° C. In addition, DSC analysis showed a possible dehydration endotherm between 25° C. and 80° C. Form I has a TGA thermograph as depicted in FIG. 31, comprising a total mass loss of approximately 1.6% of the total mass of the sample when heated from approximately 25° C. to about 110° C.

A list of X-Ray diffraction peaks for Form I is provided below in Table 8.

TABLE 8

X-Ray Diffraction Peaks for Form I.

| Two-theta angle (°) | d Space (Å) | Height (counts) |
|---|---|---|
| 4.0 | 22.036 | 626.0 |
| 8.0 | 11.045 | 87.4 |
| 12.0 | 7.363 | 3274.5 |
| 13.5 | 6.563 | 195.8 |
| 17.6 | 5.040 | 300.6 |
| 19.2 | 4.621 | 139.1 |
| 20.1 | 4.419 | 2712.7 |
| 21.5 | 4.141 | 244.6 |
| 32.4 | 2.764 | 53.1 |

(i) Form J

Compound 1 (80.3 mg) was mixed with ethyl methyl ketone (11 mL), sonicated for 5 min, and filtered via 0.2 μm PTFE-membraned syringe filter. The filtrate was evaporated to dryness in fume hood under nitrogen purge. Ethyl methyl ketone (0.6 mL) was added to the sample. The sample was capped and stirred at 500 rotations per minute at ambient temperature for about a day. The solids were isolated via 0.2 μm Nylon-membraned centrifuge tube filter and further dried in vacuum oven at 35° C. for about a day to yield Form J of Compound 1.

Form J has a Raman Spectrum as depicted in FIG. 34. Form J has a DSC thermograph substantially as depicted in FIG. 35, comprising an endothermic peak with onset temperature of 143.4° C. Form J has a TGA thermograph as depicted in FIG. 35, comprising a total mass loss of approximately 0.1% of the total mass of the sample when heated to 100° C.

A list of X-Ray diffraction peaks for Form J is provided below in Table 9.

TABLE 9

X-Ray Diffraction Peaks for Form J.

| Two-theta angle (°) | d Space (Å) | Height (counts) |
|---|---|---|
| 7.9 | 11.177 | 699 |
| 11.5 | 7.706 | 1109 |
| 11.9 | 7.407 | 3267 |
| 13.4 | 6.606 | 937 |
| 13.8 | 6.432 | 676 |
| 14.0 | 6.325 | 436 |
| 15.7 | 5.642 | 1033 |
| 17.4 | 5.081 | 1973 |
| 18.9 | 4.689 | 495 |
| 19.6 | 4.537 | 664 |
| 20.0 | 4.429 | 3353 |
| 21.0 | 4.227 | 375 |
| 21.4 | 4.157 | 1325 |
| 23.5 | 3.785 | 1010 |

(j) Form K

Compound 1 (130 mg) was dried in a vacuum oven at 35° C. for 3 hours, then mixed with ethyl methyl ketone (3.5 mL). The sample was filtered via 0.2 μm PTFE-membraned syringe filter. The filtrate was evaporated in fume hood under nitrogen purge until precipitates were visually observed. The sample was capped and stirred at 500 rotations per minute at ambient temperature for about a day. The solids were isolated via 0.2 μm Nylon-membraned centrifuge tube filter and further dried in vacuum oven at 35° C. for about a day to yield Form J of Compound 1.

Form K has a DSC thermograph substantially as depicted in FIG. 37, comprising endothermic peaks with peak maximum temperatures of approximately 98.9° C. and 113.7° C., respectively. Form K has a TGA thermograph as depicted in FIG. 37, comprising a total mass loss of approximately 0.1% of the total mass of the sample when heated to 90° C.

A list of X-Ray diffraction peaks for Form K is provided below in Table 10.

TABLE 10

X-Ray Diffraction Peaks for Form K.

| Two-theta angle (°) | d Space (Å) | Height (counts) |
|---|---|---|
| 7.3 | 12.160 | 1412 |
| 8.0 | 11.053 | 427 |
| 10.0 | 8.832 | 847 |
| 10.9 | 8.096 | 1585 |
| 11.5 | 7.667 | 1069 |
| 12.0 | 7.392 | 2072 |
| 13.4 | 6.600 | 937 |
| 14.1 | 6.265 | 1205 |
| 15.7 | 5.638 | 1317 |
| 17.5 | 5.073 | 2312 |
| 19.0 | 4.665 | 688 |
| 20.1 | 4.413 | 1774 |
| 21.3 | 4.160 | 1309 |
| 23.5 | 3.790 | 1521 |

(k) Form L

Form K of Compound 1 was dried in vacuum oven at 35° C. for two days. A portion of the sample was heated to 121° C. at 10° C./min on DSC in a crimped pan with a pin hole on its lid. The solid residue was recovered as Form L of Compound 1.

Form L has a Raman Spectrum as depicted in FIG. 39. A list of X-Ray diffraction peaks for Form L is provided below in Table 11.

TABLE 11

X-Ray Diffraction Peaks for Form L.

| Two-theta angle (°) | d Space (Å) | Height (counts) |
|---|---|---|
| 11.5 | 7.658 | 903 |
| 12.0 | 7.370 | 1001 |
| 13.4 | 6.605 | 637 |
| 15.7 | 5.634 | 856 |
| 17.5 | 5.070 | 1378 |
| 19.0 | 4.676 | 489 |
| 19.6 | 4.529 | 516 |
| 20.1 | 4.415 | 1127 |
| 21.0 | 4.233 | 481 |
| 21.3 | 4.167 | 1018 |
| 23.5 | 3.790 | 977 |

(l) Form M

Form K of Compound 1 was dried in vacuum oven at 35° C. for two days. A portion of the sample was heated to 102° C. at 10° C./min on DSC in a crimped pan with a pin hole on its lid. The solid residue was recovered as Form M of Compound 1.

Form M has a Raman Spectrum as depicted in FIG. 41. A list of X-Ray diffraction peaks for Form M is provided below in Table 12.

TABLE 12

X-Ray Diffraction Peaks for Form M.

| Two-theta angle (°) | d Space (Å) | Height (counts) |
| --- | --- | --- |
| 7.2 | 12.230 | 2115 |
| 8.0 | 11.100 | 676 |
| 9.5 | 9.325 | 660 |
| 10.9 | 8.108 | 1173 |
| 11.5 | 7.674 | 1098 |
| 12.0 | 7.387 | 1702 |
| 13.4 | 6.594 | 860 |
| 15.7 | 5.639 | 1533 |
| 16.4 | 5.415 | 1555 |
| 17.5 | 5.075 | 1748 |
| 18.2 | 4.878 | 1455 |
| 19.0 | 4.674 | 905 |
| 19.5 | 4.540 | 860 |
| 20.1 | 4.413 | 1729 |
| 20.7 | 4.294 | 555 |
| 21.3 | 4.162 | 1650 |
| 22.8 | 3.895 | 2910 |
| 23.4 | 3.794 | 1134 |

(m) Form N

Form E of Compound 1 (8.6 mg) was mixed with Milli-Q water (0.12 mL) in a clear glass vial. The sample was capped and stirred at 400 rotations per minute at ambient temperature for 5 days. The solids were isolated via 0.2 um Nylon-membraned centrifuge tube filter, and dried in vacuum oven at 35° C. for one day to obtain Form N of Compound 1.

Form N has a Raman Spectrum as depicted in FIG. 43. Form N has a DSC thermograph substantially as depicted in FIG. 44, comprising an endothermic peak with onset temperature of approximately 85.7° C. Form N has a TGA thermograph as depicted in FIG. 44, comprising a total mass loss of approximately 1.2% of the total mass of the sample when heated to 105.5° C.

A list of X-Ray diffraction peaks for Form N is provided below in Table 13.

TABLE 13

X-Ray Diffraction Peaks for Form N.

| Two-theta angle (°) | d Space (Å) | Height (counts) |
| --- | --- | --- |
| 11.6 | 7.651 | 1067 |
| 12.0 | 7.346 | 6347 |
| 13.5 | 6.541 | 1684 |
| 13.8 | 6.427 | 1502 |
| 14.0 | 6.313 | 1238 |
| 14.6 | 6.070 | 724 |
| 15.8 | 5.591 | 1268 |
| 16.2 | 5.461 | 1232 |
| 17.7 | 5.021 | 4116 |
| 19.2 | 4.610 | 1089 |
| 19.6 | 4.532 | 789 |
| 20.1 | 4.415 | 5822 |
| 21.6 | 4.117 | 2900 |
| 21.7 | 4.096 | 2489 |
| 23.2 | 3.825 | 430 |
| 23.7 | 3.748 | 2498 |
| 24.1 | 3.694 | 1196 |

6.3 Evaluation of Solid Forms (a) Solubility Measurements

A weighed sample of each of Form A, Form B, Form C, Form D, Form E, Form F, Form H, and Form I is treated with aliquots of the test solvent at ambient temperature or elevated temperature. Complete dissolution of the test material is determined by visual inspection. Solubility is estimated based on the total solvent used to provide complete dissolution of the sample. The actual solubility may be greater than the value calculated because of the use of solvent aliquots that were too large or due to a slow rate of dissolution.

In addition, a weighed sample of each of Form J, Form K, Form L, Form M, or Form N is treated with aliquots of the test solvent at ambient temperature or elevated temperature. Complete dissolution of the test material is determined by visual inspection. Solubility is estimated based on the total solvent used to provide complete dissolution of the sample. The actual solubility may be greater than the value calculated because of the use of solvent aliquots that were too large or due to a slow rate of dissolution.

(b) Stability Measurements

Stability of each of Form A, Form B, Form C, Form D, Form E, Form F, Form H, and Form I is determined by exposing the sample to a 40° C./75% relative humidity (RH) environment for four weeks or 11% RH at ambient temperature for four days.

In addition, stability of each of Form J, Form K, Form L, Form M, or Form N is determined by exposing the sample to a 40° C./75% relative humidity (RH) environment for four weeks or 11% RH at ambient temperature for four days.

6.4 Biological Evaluation (a) S1P1 Assays

The compounds are useful in the treatment of a variety of S1P1 receptor-mediated clinical conditions, including autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas. Therefore, the compounds of the invention may be assayed for their ability to modulate the S1P1 receptor activity. See Colandrea, *Biorg. Med. Chem. Lett.* 2006, 16(11):2905-2908.

(i) In Vitro Binding Assay

The solid forms described herein (e.g., Form A, Form B, Form C, Form D, Form E, Form F, Form H, and Form I) are evaluated using a [$^{35}$S]-GTPgammaS binding assay to monitor dose-dependent selectivity against S1P1 receptors. The assay is completed with sample solid forms subjected to an eight-point, four-fold dose response curve with starting concentration of 10 μM. Selectivity is determined upon initial addition of solid forms followed by an incubation period. Following compound incubation, bounded [$^{35}$S]-GTPgammaS is determined by filtration and scintillation counting. Percentage activation and inhibition values are determined relative to the reference agonist at S1P1.

In addition, the solid forms described herein (e.g., Form J, Form K, Form L, Form M, and Form N) are evaluated using a [$^{35}$S]-GTPgammaS binding assay to monitor dose-dependent selectivity against S1P1 receptors. The assay is completed with sample solid forms subjected to an eight-point, four-fold dose response curve with starting concentration of 10 μM. Selectivity is determined upon initial addition of solid forms followed by an incubation period. Following compound incubation, bounded [$^{35}$S]-GTPgammaS is determined by filtration and scintillation counting. Percentage activation and inhibition values are determined relative to the reference agonist at S1P1.

(ii) In Vivo Blood Lymphocyte Depletion Assay

In addition to their S1P1 binding properties, modulators of the S1P1 receptor also have accelerating lymphocyte homing properties. These properties may be measured using a blood lymphocyte depletion assay. The solid forms described herein (e.g., Form A, Form B, Form C, Form D, Form E, Form F, Form H, and Form I) are administered orally by gavage to rats. Tail blood for hematological monitoring is obtained on day 1 to give the baseline individual values, and at 2, 6, 24, 48 and 72 hours after application. The change in peripheral blood lymphocytes is measured across different doses of the solid forms.

In addition, the solid forms described herein (e.g., Form J, Form K, Form L, Form M, and Form N) are administered orally by gavage to rats. Tail blood for hematological monitoring is obtained on day 1 to give the baseline individual values, and at 2, 6, 24, 48 and 72 hours after application. The change in peripheral blood lymphocytes is measured across different doses of the solid forms.

(b) In Vitro Metabolic Disposition in Liver Microsomal Fractions

The stability of each of Form A, Form B, Form C, Form D, Form E, Form F, Form H, and Form I is determined according to standard procedures known in the art. For example, stability of each of Form A, Form B, Form C, Form D, Form E, Form F, Form H, and Form I is established by an in vitro assay. An in vitro hepatic microsome stability assay measures the stability of one or more subject compounds when reacting with mouse, rat or human microsomes.

In addition, the stability of each of Form J, Form K, Form L, Form M, and Form N is determined according to standard procedures known in the art. For example, stability of each of Form J, Form K, Form L, Form M, and Form N is established by an in vitro assay. An in vitro hepatic microsome stability assay measures the stability of one or more subject compounds when reacting with mouse, rat or human microsomes.

Incubations with liver microsomes are conducted in a final volume of 0.1 mL per incubation time point. 10 µM of the subject compound from a stock solution in DMSO (final DMSO concentration of 0.1%) is incubated at 37° C. from 0-60 min with pooled microsomal protein (1.0 mg/mL), suspended in incubation buffer (0.1 M potassium phosphate, pH 7.4, 5 mM $MgCl_2$, and 0.1 mM EDTA). The microsomal reaction is initiated by the addition of NADPH (3 mM final concentration). Incubations with (a) no protein or (b) no NADPH serve as controls. Reactions are terminated by the addition of 0.2 mL of stop solution (acetonitrile). The samples are vortex-mixed for 30 sec and then centrifuged at 10,000×g for 10 min. The supernatant is dried using a Labconco CentriVap concentrator and the dry residue reconstituted in water, transferred to an HPLC glass vial and analyzed by HPLC-UV. The disappearance of the subject compound is used to evaluate the in vitro metabolism thereof.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A solid form of (E)-1-(4-(1-(((4-cyclohexyl-3-(trifluoromethyl)benzyl)oxy)imino)ethyl)-2-ethylbenzyl)azetidine-3-carboxylic acid selected from the group consisting of Form A, Form B, Form C, Form H, Form I, Form F and mixtures of any of the foregoing.

2. The solid form of claim 1, wherein the solid form is Form A and has an X-ray powder diffraction pattern comprising three or more peaks at 2.3, 3.9, 7.7, 11.5, or 20.9° 2θ (±0.2° 2θ).

3. The solid form of claim 1, wherein the solid form is Form C and has an X-ray powder diffraction pattern comprising three or more peaks at 2.2, 3.9, 6.5, 7.7, 11.5, or 20.9° 2θ (±0.2° 2θ).

4. The solid form of claim 1, wherein the solid form is Form B and has an X-ray powder diffraction pattern comprising three or more peaks at 2.3, 2.8, 7.7, 8.4, 11.5, or 20.9° 2θ (±0.2° 2θ).

5. The solid form of claim 1, wherein Form F has an X-ray powder diffraction pattern comprising three or more peaks at 3.3, 9.9, 14.8, 19.9, 20.4, or 23.5° 2θ (±0.2° 2θ).

6. The solid form of claim 1, wherein Form H has an X-ray powder diffraction pattern comprising three or more peaks at 3.6, 7.2, 10.8, 17.8, 18.0, 18.3, or 21.7° 2θ (±0.2° 2θ).

7. The solid form of claim 1, wherein Form I has an X-ray powder diffraction pattern comprising three or more peaks at 4.0, 12.0, 17.6, 20.1, or 21.5° 2θ (±0.2° 2θ).

8. A pharmaceutical composition comprising the solid form of claim 1 and pharmaceutically acceptable carrier or excipient.

9. The pharmaceutical composition of claim 8, which is a single unit dosage form.

10. The pharmaceutical composition of claim 8, which is selected from a tablet and a capsule.

* * * * *